US008187207B2

(12) United States Patent
Machold et al.

(10) Patent No.: US 8,187,207 B2

(45) Date of Patent: May 29, 2012

(54) DEVICES, SYSTEMS, AND METHODS FOR RESHAPING A HEART VALVE ANNULUS, INCLUDING THE USE OF MAGNETIC TOOLS

(75) Inventors: Timothy R Machold, Moss Beach, CA (US); Robert T Chang, Belmont, CA (US); David A Rahdert, San Francisco, CA (US); David Scott, Redwood City, CA (US); David Rainoue Tholfsen, San Leandro, CA (US)

(73) Assignee: MVRx, Inc., Moss Beach, CA (US)

( * ) Notice: Subject to any disclaimer, the term of this patent is extended or adjusted under 35 U.S.C. 154(b) by 0 days.

(21) Appl. No.: 12/657,527

(22) Filed: Jan. 22, 2010

(65) Prior Publication Data

US 2010/0130992 A1 May 27, 2010

Related U.S. Application Data

(63) Continuation of application No. 11/903,472, filed on Sep. 21, 2007, now abandoned, which is a continuation-in-part of application No. 11/089,939, filed on Mar. 25, 2005, now abandoned, which is a continuation-in-part of application No. 10/894,433, filed on Jul. 19, 2004, which is a continuation-in-part of application No. 10/677,104, filed on Oct. 1, 2003, now abandoned.

(51) Int. Cl.

| | |
|---|---|
| *A61M 25/00* | (2006.01) |
| *A61M 29/00* | (2006.01) |
| *A61F 2/24* | (2006.01) |

(52) U.S. Cl. ........................ 600/585; 604/96.01; 623/2.1

(58) Field of Classification Search .................. 600/585; 623/2.1; 604/96.01

See application file for complete search history.

(56) References Cited

U.S. PATENT DOCUMENTS

| | | | | |
|---|---|---|---|---|
| 5,269,759 | A | 12/1993 | Hernandez et al. | |
| 5,492,538 | A | 2/1996 | Johlin, Jr. | |
| 5,507,731 | A | 4/1996 | Hernandez et al. | |
| 5,624,430 | A | 4/1997 | Eton et al. | |
| 5,851,185 | A | 12/1998 | Berns | |
| 5,895,404 | A | 4/1999 | Ruiz | |
| 5,916,194 | A * | 6/1999 | Jacobsen et al. | 604/96.01 |
| 6,385,472 | B1 | 5/2002 | Hall et al. | |
| 6,652,540 | B1 | 11/2003 | Cole et al. | |
| 6,669,679 | B1 | 12/2003 | Savage et al. | |
| 2002/0010481 | A1 | 1/2002 | Jayaraman | |

* cited by examiner

*Primary Examiner* — Max Hindenburg
*Assistant Examiner* — Adam Eiseman
(74) *Attorney, Agent, or Firm* — Ryan Kromholz & Manion, S.C.

(57) ABSTRACT

Implants or systems of implants and methods apply a selected force vector or a selected combination of force vectors within or across the left atrium, which allow mitral valve leaflets to better coapt. The implants or systems of implants and methods make possible rapid deployment, facile endovascular delivery, and full intra-atrial retrievability. The implants or systems of implants and methods also make use of strong fluoroscopic landmarks. The implants or systems of implants and methods make use of an adjustable implant and a fixed length implant. The implants or systems of implants and methods may also utilize a bridge stop to secure the implant, and the methods of implantation employ various tools.

5 Claims, 37 Drawing Sheets

1060
1026
1062
1064
1030
1068
1020
1010
1008
1188
1182
1032
1012
1080
1048
1046
1042
1184
1016
1044
1186
1140

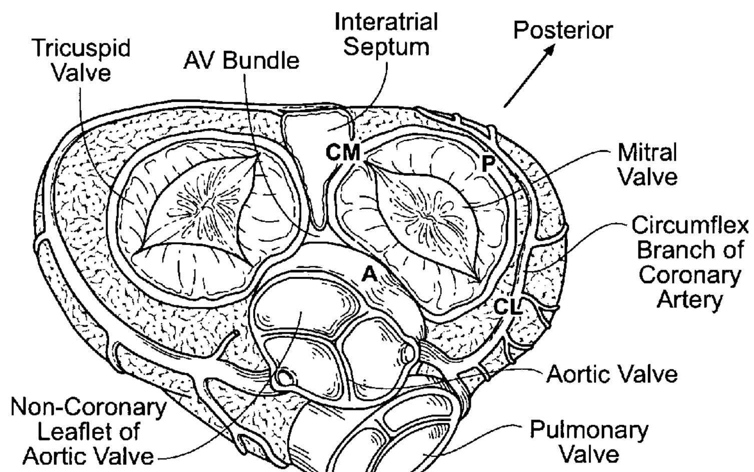
*Fig. 2*
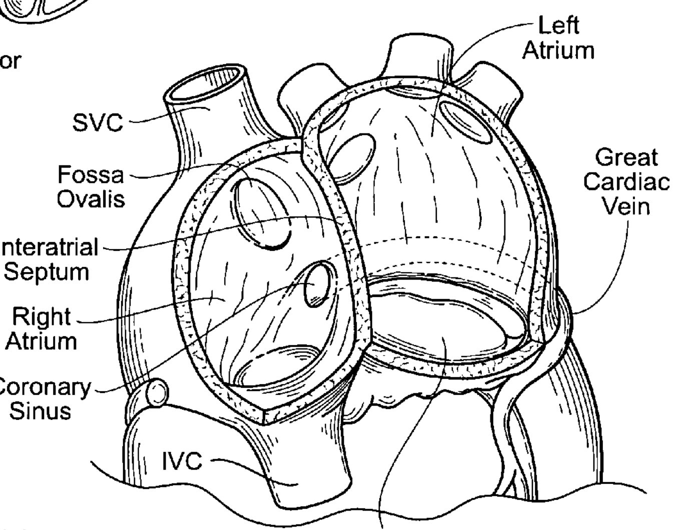
*Fig. 3*
*Fig. 4*
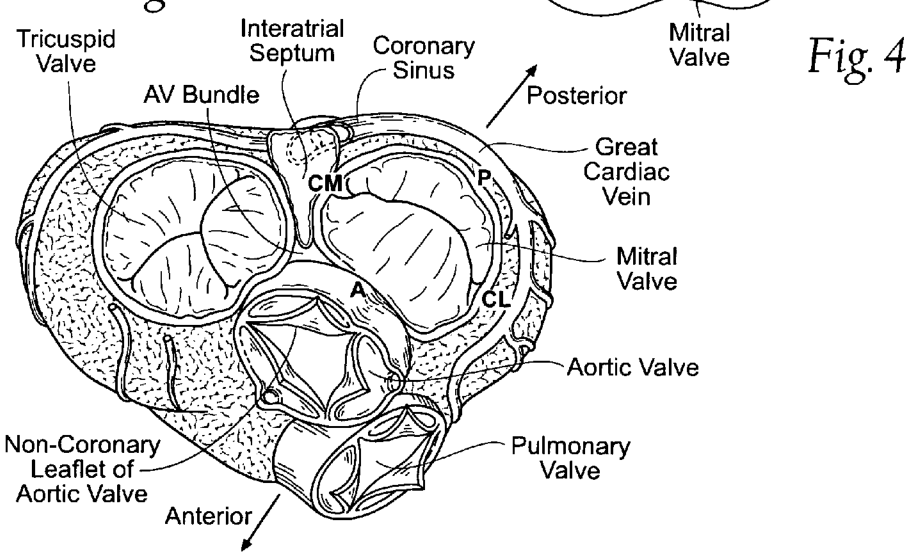

Interatrial
Septum
16
12
Fossa
Ovalis
Left Atrium
Right
Atrium
18
14

20
30
10
Coronary
Sinus
Mitral
Valve

Interatrial
Septum
16
Fossa
Ovalis
Left Atrium
Right
Atrium
12
18
14

20
30
Mitral
Valve
10
Coronary
Sinus

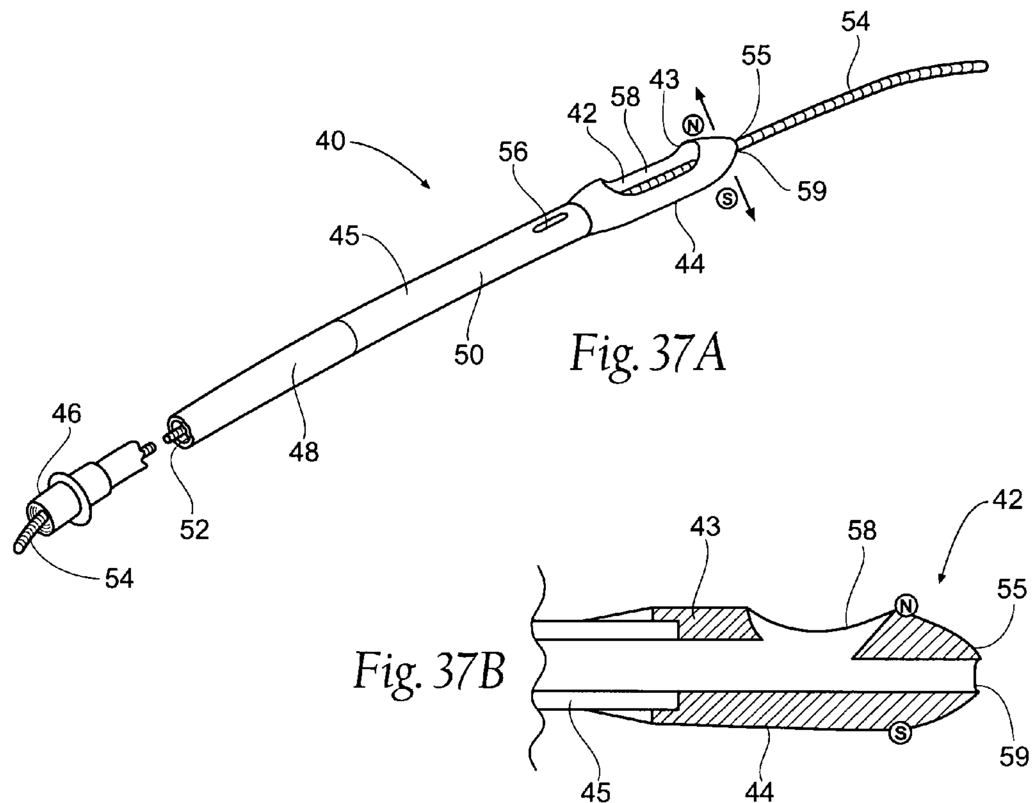
Fig. 37A
Fig. 37B
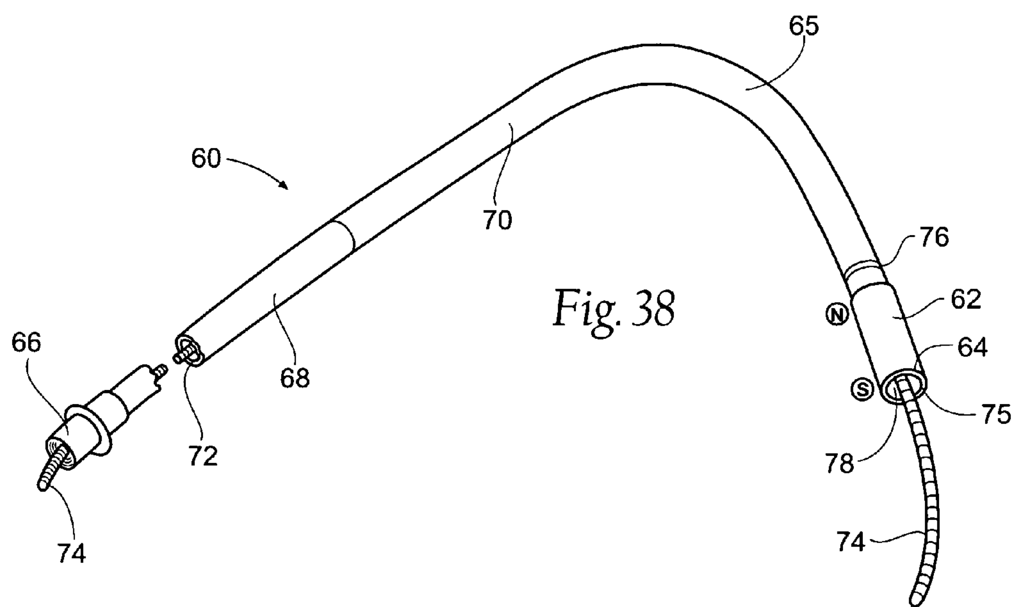
Fig. 38

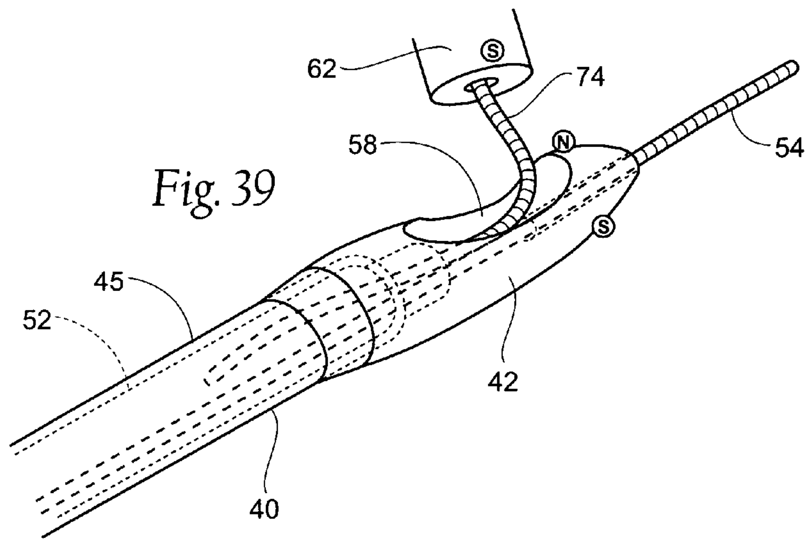
Fig. 39
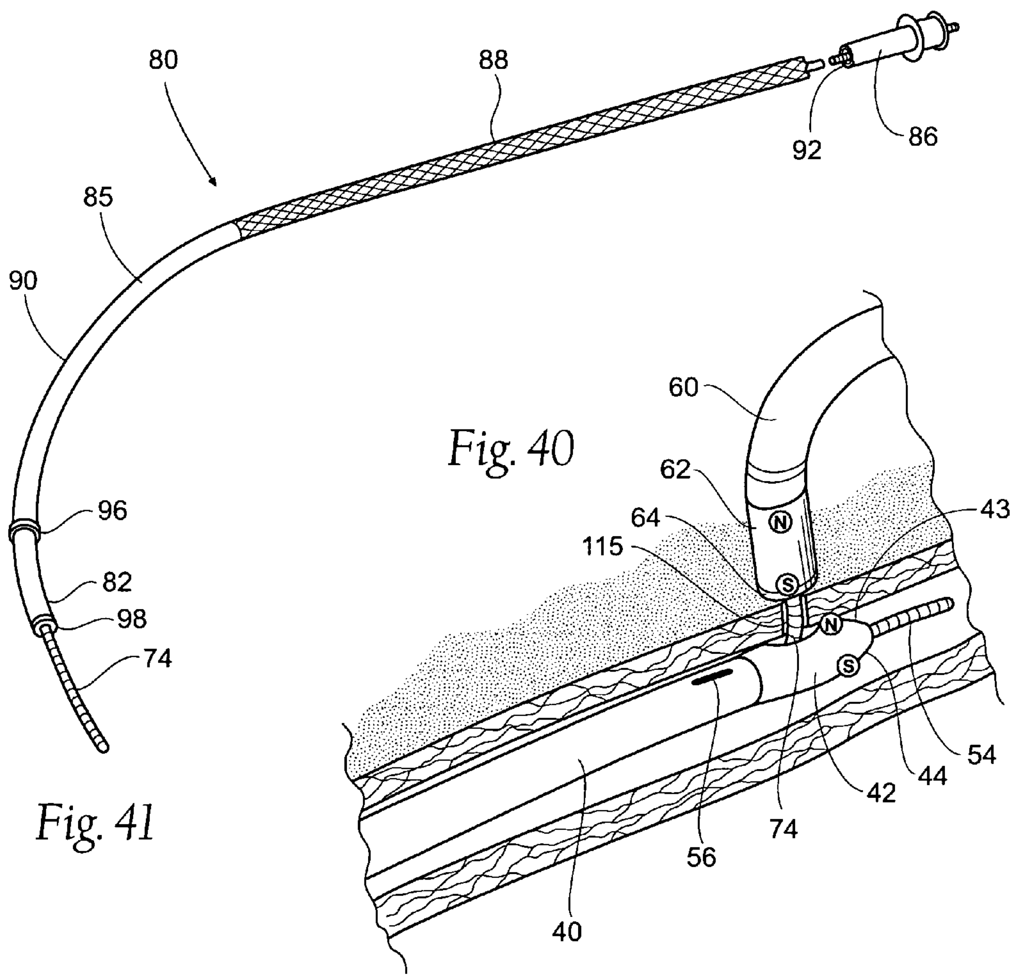
Fig. 40
Fig. 41

DEVICES, SYSTEMS, AND METHODS FOR RESHAPING A HEART VALVE ANNULUS, INCLUDING THE USE OF MAGNETIC TOOLS

RELATED APPLICATIONS

This application is a continuation of U.S. patent application Ser. No. 11/903,472, Filed Sep. 21, 2007, now abandoned which is a continuation-in-part of U.S. patent application Ser. No. 11/089,939, Filed Mar. 25, 2005, now abandoned and entitled "Devices, Systems, and Methods for Reshaping a Heart Valve Annulus, Including the Use of Magnetic Tools," which is a continuation-in-part of co-pending U.S. patent application Ser. No. 10/894,433, filed Jul. 19, 2004, and entitled "Devices, Systems, and Methods for Reshaping a Heart Valve Annulus," which is a continuation-in-part of U.S. patent application Ser. No. 10/677,104, filed Oct. 1, 2003, now abandoned and entitled "Devices, Systems, and Methods for Reshaping a Heart Valve Annulus," which claims the benefit of U.S. patent application Ser. No. 09/666,617, filed Sep. 20, 2000 and entitled "Heart Valve Annulus Device and Methods of Using Same," which is incorporated herein by reference. This application also claims the benefit of Patent Cooperation Treaty Application Serial No. PCT/US02/31376, filed Oct. 1, 2002 and entitled "Systems and Devices for Heart Valve Treatments," which claimed the benefit of U.S. Provisional Patent Application Ser. No. 60/326,590, filed Oct. 1, 2001, which are incorporated herein by reference. This application also claims the benefit of U.S. Provisional Application Ser. No. 60/429,444, filed Nov. 26, 2002, and entitled "Heart Valve Remodeling Devices;" U.S. Provisional Patent Application Ser. No. 60/429,709, filed Nov. 26, 2002, and entitled "Neo-Leaflet Medical Devices;" and U.S. Provisional Patent Application Ser. No. 60/429,462, filed Nov. 26, 2002, and entitled "Heart Valve Leaflet Retaining Devices," which are each incorporated herein by reference.

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atriums are the blood-receiving chambers, which pump blood into the ventricles. The ventricles are the blood-discharging chambers. A wall composed of fibrous and muscular parts, called the interatrial septum separates the right and left atriums (see FIGS. 2 to 4). The fibrous interatrial septum is, compared to the more friable muscle tissue of the heart, a more materially strong tissue structure in its own extent in the heart. An anatomic landmark on the interatrial septum is an oval, thumbprint sized depression called the oval fossa, or fossa ovalis (shown in FIGS. 4 and 6), which is a remnant of the oval foramen and its valve in the fetus. It is free of any vital structures such as valve structure, blood vessels and conduction pathways. Together with its inherent fibrous structure and surrounding fibrous ridge which makes it identifiable by angiographic techniques, the fossa ovalis is the favored site for trans-septal diagnostic and therapeutic procedures from the right into the left heart. Before birth, oxygenated blood from the placenta was directed through the oval foramen into the left atrium, and after birth the oval foramen closes.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atriums into the corresponding ventricles. Shortly after ventricular systole (i.e., ventricular emptying) begins, the tricuspid and mitral valves close (see FIG. 3)—to prevent back flow from the ventricles into the corresponding atriums—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

The mitral and tricuspid valves are defined by fibrous rings of collagen, each called an annulus, which forms a part of the fibrous skeleton of the heart. The annulus provides attachments for the two cusps or leaflets of the mitral valve (called the anterior and posterior cusps) and the three cusps or leaflets of the tricuspid valve. The leaflets receive chordae tendineae from more than one papillary muscle. In a healthy heart, these muscles and their tendinous chords support the mitral and tricuspid valves, allowing the leaflets to resist the high pressure developed during contractions (pumping) of the left and right ventricles. FIGS. 5 and 6 show the chordae tendineae and papillary muscles in the left ventricle that support the mitral valve.

As FIGS. 2 and 3 show, the anterior (A) portion of the mitral valve annulus is intimate with the non-coronary leaflet of the aortic valve. As FIGS. 2 and 3 also show, the mitral valve annulus is also near other critical heart structures, such as the circumflex branch of the left coronary artery (which supplies the left atrium, a variable amount of the left ventricle, and in many people the SA node) and the AV node (which, with the SA node, coordinates the cardiac cycle).

Also in the vicinity of the posterior (P) mitral valve annulus is the coronary sinus and its tributaries. These vessels drain the areas of the heart supplied by the left coronary artery. The coronary sinus and its tributaries receive approximately 85% of coronary venous blood. The coronary sinus empties into the posterior of the right atrium, anterior and inferior to the fossa ovalis (see FIG. 4). A tributary of the coronary sinus is called the great cardiac vein, which courses parallel to the majority of the posterior mitral valve annulus, and is superior to the posterior mitral valve annulus by an average distance of about 9.64±3.15 millimeters (Yamanouchi, Y, *Pacing and Clinical Electophysiology* 21(11):2522-6; 1998).

II. Characteristics and Causes of Mitral Valve Dysfunction

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (see FIGS. 7 and 8), the dimensions of the mitral valve annulus create an anatomic shape and tension such that the leaflets coapt, forming a tight junction, at peak contraction pressures. Where the leaflets coapt at the opposing medial (CM) and lateral (CL) sides of the annulus are called the leaflet commissures.

Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease.

Regardless of the cause (see FIG. 9), mitral valve dysfunction can occur when the leaflets do not coapt at peak contraction pressures. As FIG. 9 shows, the coaptation line of the two leaflets is not tight at ventricular systole. As a result, an undesired back flow of blood from the left ventricle into the left atrium can occur.

Mitral regurgitation is a condition where, during contraction of the left ventricle, the mitral valve allows blood to flow backwards from the left ventricle into the left atrium. This has two important consequences.

First, blood flowing back into the atrium may cause high atrial pressure and reduce the flow of blood into the left atrium from the lungs. As blood backs up into the pulmonary system, fluid leaks into the lungs and causes pulmonary edema.

Second, the blood volume going to the atrium reduces volume of blood going forward into the aorta causing low cardiac output. Excess blood in the atrium over-fills the ventricle during each cardiac cycle and causes volume overload in the left ventricle.

Mitral regurgitation is measured on a numeric Grade scale of 1+ to 4+ by either contrast ventriculography or by echocardiographic Doppler assessment. Grade 1+ is trivial regurgitation and has little clinical significance. Grade 2+ shows a jet of reversed flow going halfway back into the left atrium. Grade 3 regurgitation shows filling of the left atrium with reversed flow up to the pulmonary veins and a contrast injection that clears in three heart beats or less. Grade 4 regurgitation has flow reversal into the pulmonary veins and a contrast injection that does not clear from the atrium in three or fewer heart beats.

Mitral regurgitation is categorized into two main types, (i) organic or structural and (ii) functional. Organic mitral regurgitation results from a structurally abnormal valve component that causes a valve leaflet to leak during systole. Functional mitral regurgitation results from annulus dilation due to primary congestive heart failure, which is itself generally surgically untreatable, and not due to a cause like severe irreversible ischemia or primary valvular heart disease.

Organic mitral regurgitation is seen when a disruption of the seal occurs at the free leading edge of the leaflet due to a ruptured chord or papillary muscle making the leaflet flail; or if the leaflet tissue is redundant, the valves may prolapse the level at which coaptation occurs higher into the atrium with further prolapse opening the valve higher in the atrium during ventricular systole.

Functional mitral regurgitation occurs as a result of dilation of heart and mitral annulus secondary to heart failure, most often as a result of coronary artery disease or idiopathic dilated cardiomyopathy. Comparing a healthy annulus in FIG. 7 to an unhealthy annulus in FIG. 9, the unhealthy annulus is dilated and, in particular, the anterior-to-posterior distance along the minor axis (line P-A) is increased. As a result, the shape and tension defined by the annulus becomes less oval (see FIG. 7) and more round (see FIG. 9). This condition is called dilation. When the annulus is dilated, the shape and tension conducive for coaptation at peak contraction pressures progressively deteriorate.

The fibrous mitral annulus is attached to the anterior mitral leaflet in one-third of its circumference. The muscular mitral annulus constitutes the remainder of the mitral annulus and is attached to by the posterior mitral leaflet. The anterior fibrous mitral annulus is intimate with the central fibrous body, the two ends of which are called the fibrous trigones. Just posterior to each fibrous trigone is the commissure of which there are two, the anterior medial (CM) and the posterior lateral commissure (CL). The commissure is where the anterior leaflet meets the posterior leaflet at the annulus.

As before described, the central fibrous body is also intimate with the non-coronary leaflet of the aortic valve. The central fibrous body is fairly resistant to elongation during the process of mitral annulus dilation. It has been shown that the great majority of mitral annulus dilation occurs in the posterior two-thirds of the annulus known as the muscular annulus. One could deduce thereby that, as the annulus dilates, the percentage that is attached to the anterior mitral leaflet diminishes.

In functional mitral regurgitation, the dilated annulus causes the leaflets to separate at their coaptation points in all phases of the cardiac cycle. Onset of mitral regurgitation may be acute, or gradual and chronic in either organic or in functional mitral regurgitation.

In dilated cardiomyopathy of ischemic or of idiopathic origin, the mitral annulus can dilate to the point of causing functional mitral regurgitation. It does so in approximately twenty-five percent of patients with congestive heart failure evaluated in the resting state. If subjected to exercise, echocardiography shows the incidence of functional mitral regurgitation in these patients rises to over fifty percent.

Functional mitral regurgitation is a significantly aggravating problem for the dilated heart, as is reflected in the increased mortality of these patients compared to otherwise comparable patients without functional mitral regurgitation. One mechanism by which functional mitral regurgitation aggravates the situation in these patients is through increased volume overload imposed upon the ventricle. Due directly to the leak, there is increased work the heart is required to perform in each cardiac cycle to eject blood antegrade through the aortic valve and retrograde through the mitral valve. The latter is referred to as the regurgitant fraction of left ventricular ejection. This is added to the forward ejection fraction to yield, the total ejection fraction. A normal heart has a forward ejection fraction of about 50 to 70 percent. With functional mitral regurgitation and dilated cardiomyopathy, the total ejection fraction is typically less than thirty percent. If the regurgitant fraction is half the total ejection fraction in the latter group the forward ejection fraction can be as low as fifteen percent.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

Currently, patient selection criteria for mitral valve surgery are very selective. Possible patient selection criteria for mitral surgery include: normal ventricular function, general good health, a predicted lifespan of greater than 3 to 5 years, NYHA Class III or IV symptoms, and at least Grade 3 regurgitation. Younger patients with less severe symptoms may be indicated for early surgery if mitral repair is anticipated. The most common surgical mitral repair procedure is for organic mitral regurgitation due to a ruptured chord on the middle scallop of the posterior leaflet.

In conventional annuloplasty ring repair, the posterior mitral annulus is reduced along its circumference with sutures passed through a surgical annuloplasty sewing ring cuff. The goal of such a repair is to bring the posterior mitral leaflet forward toward to the anterior leaflet to better allow coaptation.

Surgical edge-to-edge juncture repairs, which can be performed endovascularly, are also made, in which a mid valve leaflet to mid valve leaflet suture or clip is applied to keep these points of the leaflet held together throughout the cardiac cycle. Other efforts have developed an endovascular suture and a clip to grasp and bond the two mitral leaflets in the beating heart.

Grade 3+ or 4+ organic mitral regurgitation may be repaired with such edge-to-edge technologies. This is because, in organic mitral regurgitation, the problem is not the annulus but in the central valve components.

However, functional mitral regurgitation can persist at a high level, even after edge-to-edge repair, particularly in cases of high Grade 3+ and 4+ functional mitral regurgitation. After surgery, the repaired valve may progress to high rates of functional mitral regurgitation over time.

In yet another emerging technology, the coronary sinus is mechanically deformed through endovascular means applied and contained to function solely within the coronary sinus.

It is reported that twenty-five percent of the six million Americans who will have congestive heart failure will have functional mitral regurgitation to some degree. This constitutes the 1.5 million people with functional mitral regurgitation. Of these, the idiopathic dilated cardiomyopathy accounts for 600,000 people. Of the remaining 900,000 people with ischemic disease, approximately half have functional mitral regurgitation due solely to dilated annulus.

By interrupting the cycle of progressive functional mitral regurgitation, it has been shown in surgical patients that survival is increased and in fact forward ejection fraction increases in many patients. The problem with surgical therapy is the significant insult it imposes on these chronically ill patients with high morbidity and mortality rates associated with surgical repair.

The need remains for simple, cost-effective, and less invasive devices, systems, and methods for treating dysfunction of a heart valve, e.g., in the treatment of organic and functional mitral valve regurgitation.

SUMMARY OF THE INVENTION

The invention provides devices, systems, and methods for reshaping a heart valve annulus, including the use of magnetic tools.

One aspect of the invention provides devices, systems, and methods for reshaping a heart valve annulus, including the use of magnetic tools and comprises a first catheter and a second catheter. The first and second catheters each may include a guide lumen having a distal opening, and magnetic or ferromagnetic materials placed adjacent the distal openings of both guide lumens. The magnetic or ferromagnetic materials are desirably sized and configured to magnetically couple the distal opening of the first catheter to the distal opening of the second catheter in an alignment that accommodates passage of an operative component between the guide lumens of the first and second catheters.

Another aspect of the invention provides a plurality of magnetic portions configured to provide both attractive and repulsive forces and this increase the strength of the magnetic coupling between the first and second catheters.

Other features and advantages of the invention shall be apparent based upon the accompanying description, drawings, and claims.

BRIEF DESCRIPTION OF THE DRAWINGS

FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.

FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.

FIG. 4 is an anatomic anterior perspective view of the left and right atriums, with portions broken away and in section to show the interior of the heart chambers and associated structures, such as the fossa ovalis, coronary sinus, and the great cardiac vein.

FIG. 37A is a perspective view of a catheter used in the implantation of an implant system of the type shown in FIGS. 10A to 10C.

FIG. 37B is a partial sectional view showing a magnetic head of the catheter as shown in FIG. 37A.

FIG. 38 is a perspective view of an additional catheter which may be used in the implantation of an implant system of the type shown in FIGS. 10A to 10C.

FIG. 39 is a partial perspective view of the interaction between the magnetic head of the catheter shown in FIG. 37A and the magnetic head of the catheter shown in FIG. 38, showing a guide wire extending out of one magnetic head and into the other magnetic head.

FIG. 40 is an anatomic partial perspective view of the magnetic catheter heads shown in FIG. 39, with one catheter shown in the left atrium and one catheter shown in the great cardiac vein.

FIG. 41 is a perspective view of an additional catheter which may be used in the implantation of an implant system of the type shown in FIGS. 10A to 10C.

FIGS. 54 to 56A are perspective views of alternative implant systems of the type shown in FIGS. 10A to 10C, showing alternative bridge locks in both the anterior bridge stop region and the posterior bridge stop region.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 10A:
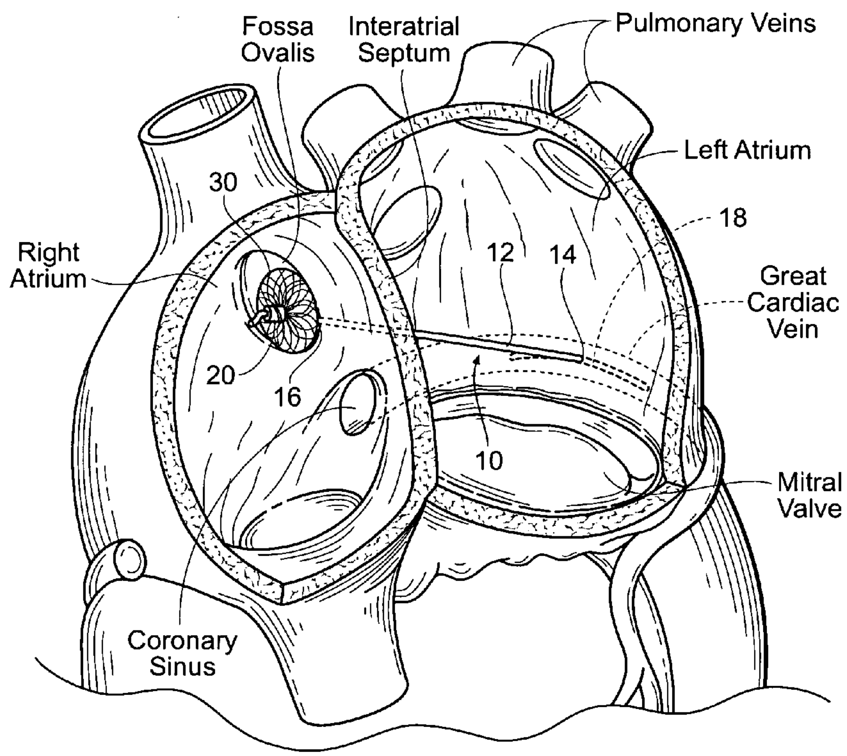
FIGS. 10A and 10B are anatomic anterior perspective views of the left and right atriums, with portions broken away and in section to show the presence of an implant system that includes an inter-atrial bridging element that spans the mitral valve annulus, with a posterior bridge stop positioned in the great cardiac vein and an anterior bridge stop, including a septal member, positioned on the inter-atrial septum, the inter-atrial bridging element extending in an essentially straight path generally from a mid-region of the annulus to the inter-atrial septum.
Figure 10B:
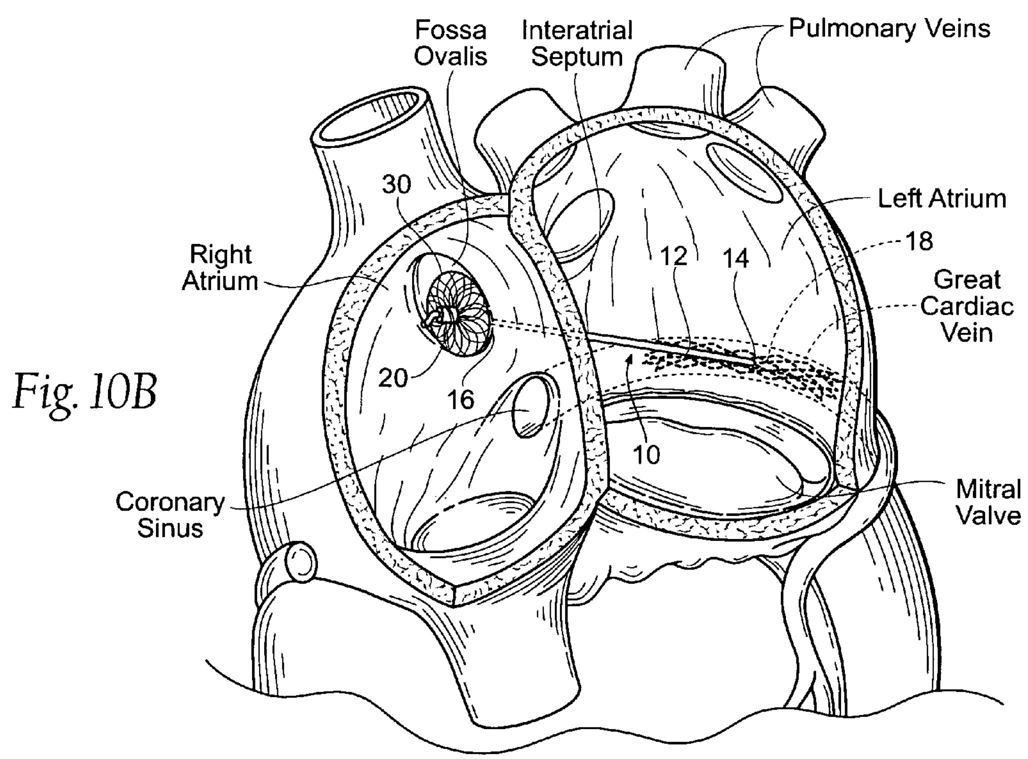
Figure 10C:
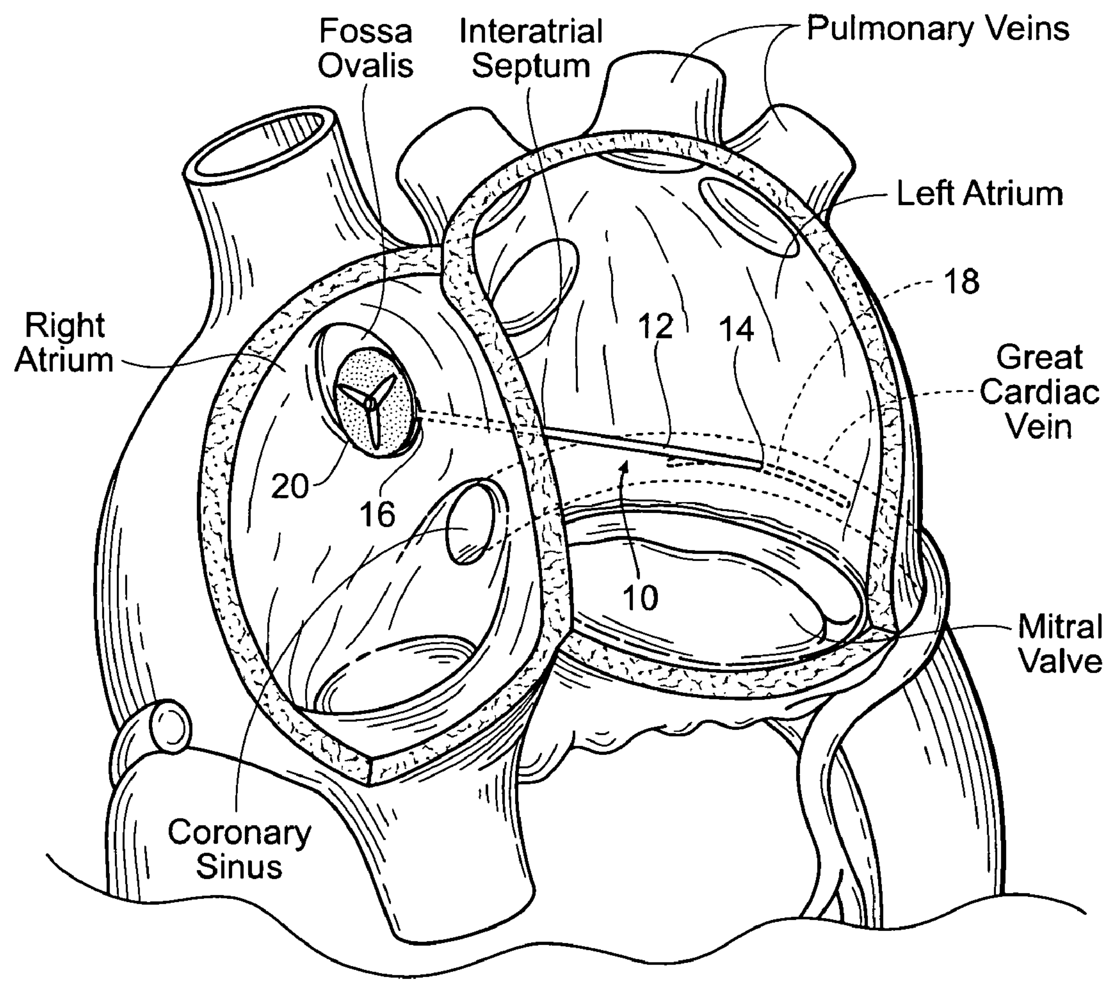
FIG. 10C is an anatomic anterior perspective view of an alternative embodiment of the implant system shown in FIGS. 10A and 10B, showing an anterior bridge stop without the addition of a septal member.

I. Trans-Septal Implants for Direct Shortening of the Minor Axis of a Heart Valve Annulus A. Implant Structure FIGS. 10A to 10C show embodiments of an implant 10 that is sized and configured to extend across the left atrium in generally an anterior-to-posterior direction, spanning the mitral valve annulus. The implant 10 comprises a spanning region or bridging element 12 having a posterior bridge stop region 14 and an anterior bridge stop region 16.

The posterior bridge stop region 14 is sized and configured to allow the bridging element 12 to be placed in a region of atrial tissue above the posterior mitral valve annulus. This region is preferred, because it generally presents more tissue mass for obtaining purchase of the posterior bridge stop region 14 than in a tissue region at or adjacent to the posterior mitral annulus. Engagement of tissue at this supra-annular location also may reduce risk of injury to the circumflex coronary artery. In a small percentage of cases, the circumflex coronary artery may pass over and medial to the great cardiac vein on the left atrial aspect of the great cardiac vein, coming to lie between the great cardiac vein and endocardium of the left atrium. However, since the forces in the posterior bridge stop region are directed upward and inward relative to the left atrium and not in a constricting manner along the long axis of the great cardiac vein, the likelihood of circumflex artery compression is less compared to other technologies in this field that do constrict the tissue of the great cardiac vein. Nevertheless, should a coronary angiography reveal circumflex artery stenosis, the symmetrically shaped posterior bridge stop may be replaced by an asymmetrically shaped bridge stop, such as where one limb of a T-shaped member is shorter than the other, thus avoiding compression of the crossing point of the circumflex artery. The asymmetric form may also be selected first based on a pre-placement angiogram.

An asymmetric posterior bridge stop may be utilized for other reasons as well. The asymmetric posterior bridge stop may be selected where a patient is found to have a severely stenotic distal great cardiac vein, where the asymmetric bridge stop better serves to avoid obstruction of that vessel. In addition, an asymmetric bridge stop may be chosen for its use in selecting application of forces differentially and preferentially on different points along the posterior mitral annulus to optimize treatment, i.e., in cases of malformed or asymmetrical mitral valves.

The anterior bridge stop region 16 is sized and configured to allow the bridging element 12 to be placed, upon passing into the right atrium through the septum, adjacent tissue in or near the right atrium. For example, as is shown in FIGS. 10A to 10C, the anterior bridge stop region 16 may be adjacent or abutting a region of fibrous tissue in the interatrial septum. As shown, the bridge stop site 16 is desirably superior to the anterior mitral annulus at about the same elevation or higher than the elevation of the posterior bridge stop region 14. In the illustrated embodiment, the anterior bridge stop region 16 is adjacent to or near the inferior rim of the fossa ovalis. Alternatively, the anterior bridge stop region 16 can be located at a more superior position in the septum, e.g., at or near the superior rim of the fossa ovalis. The anterior bridge stop region 16 can also be located in a more superior or inferior position in the septum, away from the fossa ovalis, provided that the bridge stop site does not harm the tissue region.

Figure 11A:
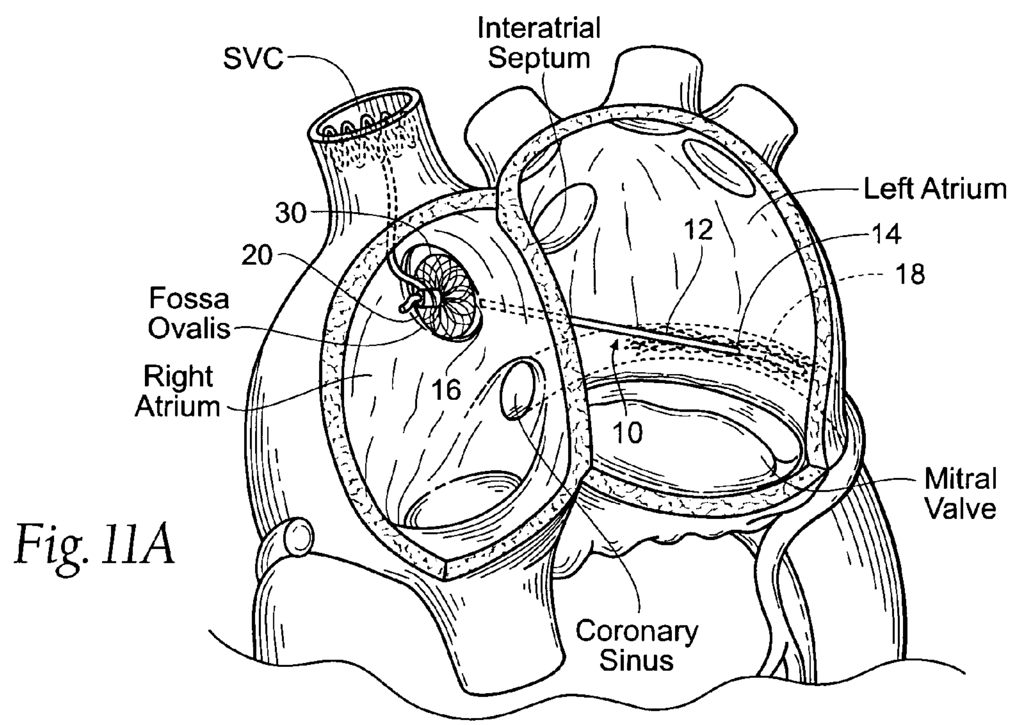
FIG. 11A is an anatomic anterior perspective view of the left and right atriums, with portions broken away and in section to show the presence of an implant system of the type shown in FIGS. 10A and 10B, with the anterior region of the implant extending through a pass-through structure, such as a septal member, in the inter-atrial septum and situated in the superior vena cava.
Figure 11B:
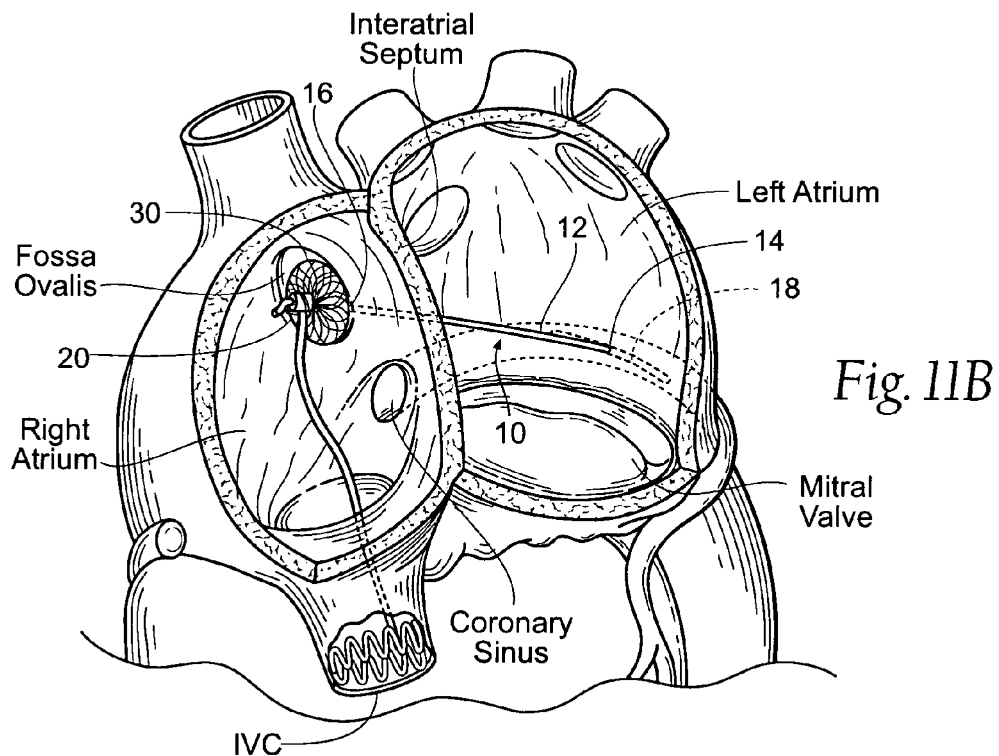
FIG. 11B is an anatomic anterior perspective view of the left and right atriums, with portions broken away and in section to show the presence of an implant system of the type shown in FIGS. 10A and 10B, with the anterior region of the implant extending through a pass-through structure, such as a septal member, in the inter-atrial septum and situated in the inferior vena cava.

Alternatively, as can be seen in FIGS. 11A and 11B, the anterior bridge stop region 16, upon passing through the septum into the right atrium, may be positioned within or otherwise situated in the superior vena cava (SVC) or the inferior vena cava (IVC), instead of at the septum itself.

Figure 1:
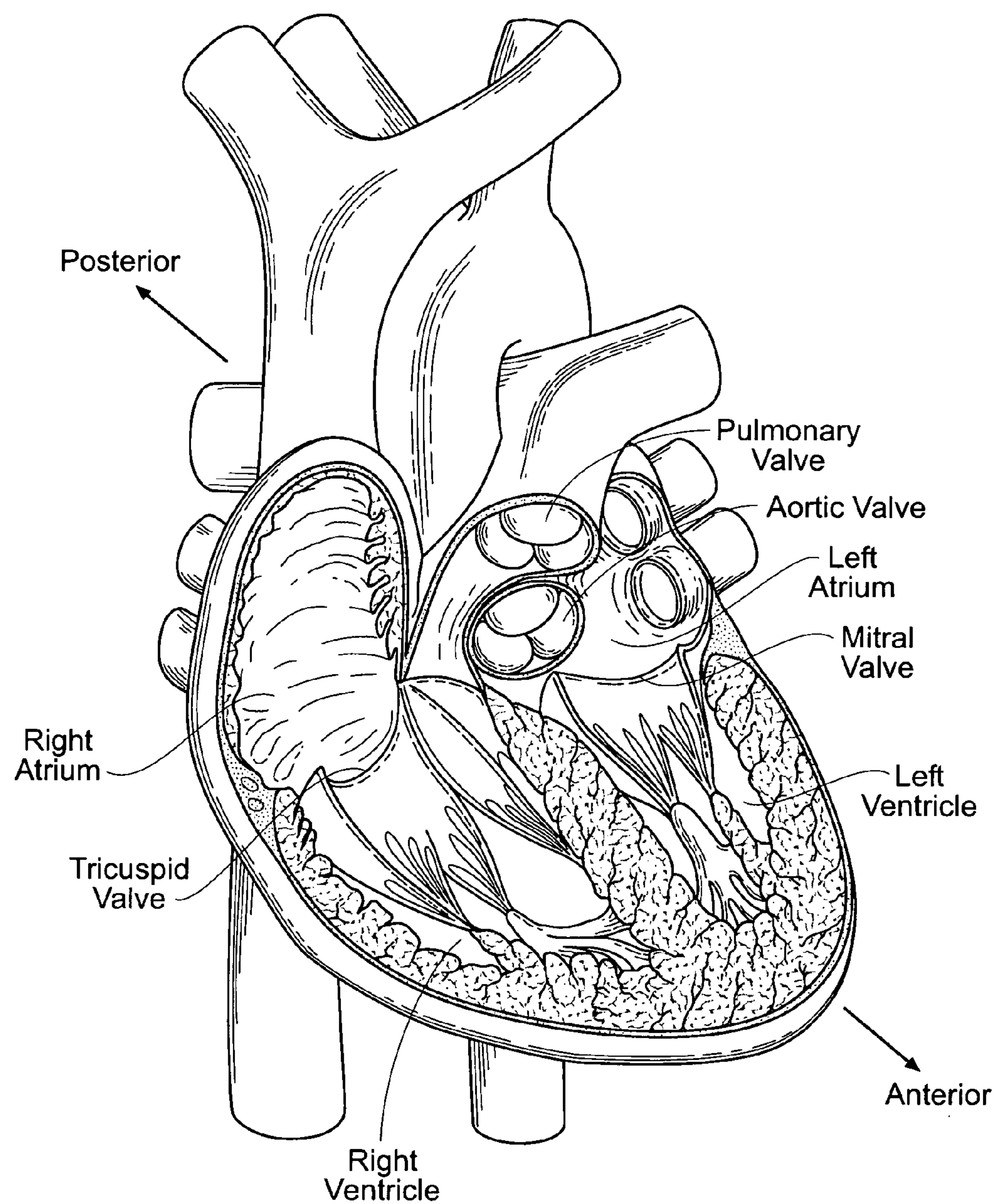
FIG. 1 is an anatomic anterior view of a human heart, with portions broken away and in section to view the interior heart chambers and adjacent structures.
Figure 5:
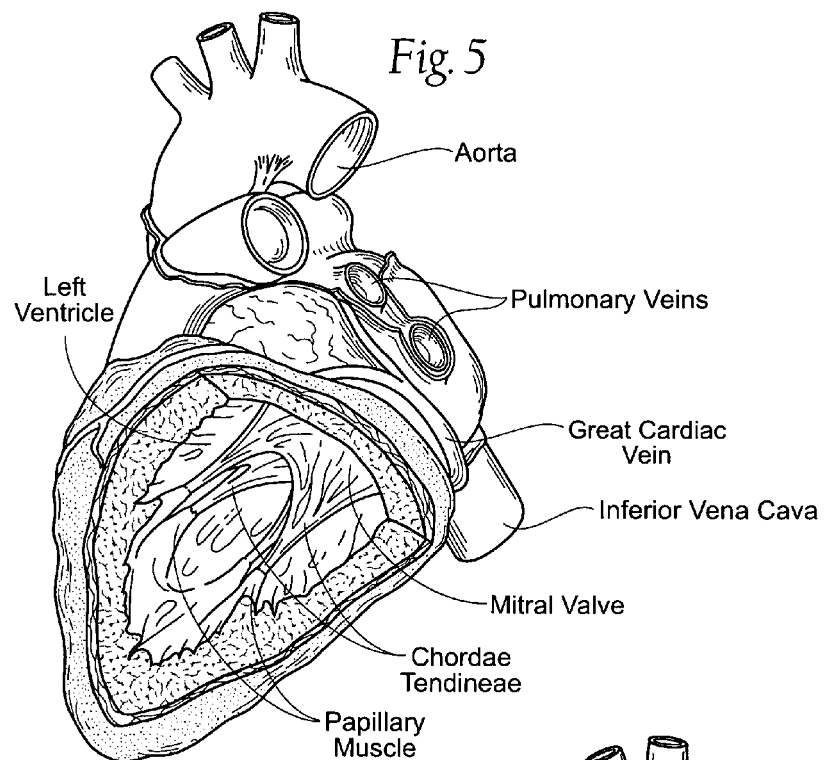
FIG. 5 is an anatomic lateral view of a human heart with portions broken away and in section to show the interior of the left ventricle and associated muscle and chord structures coupled to the mitral valve.
Figure 6:
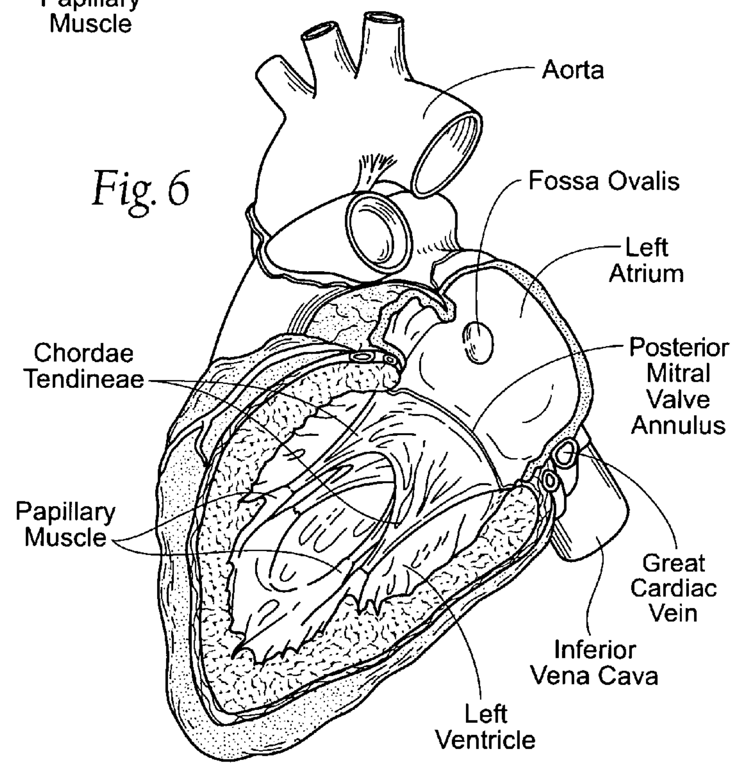
FIG. 6 is an anatomic lateral view of a human heart with portions broken away and in section to show the interior of the left ventricle and left atrium and associated muscle and chord structures coupled to the mitral valve.
Figure 7:
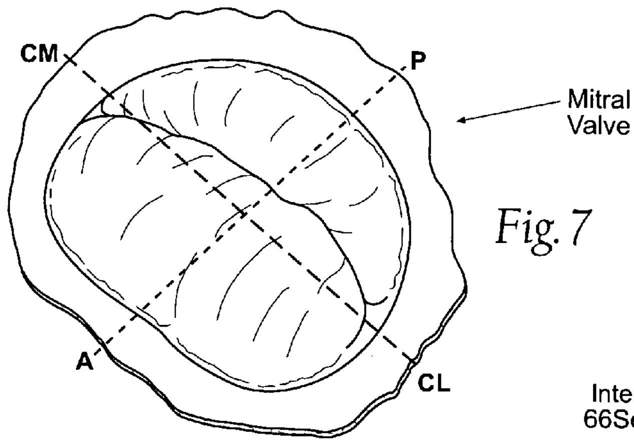
FIG. 7 is a superior view of a healthy mitral valve, with the leaflets closed and coapting at peak contraction pressures during ventricular systole.
Figure 8:
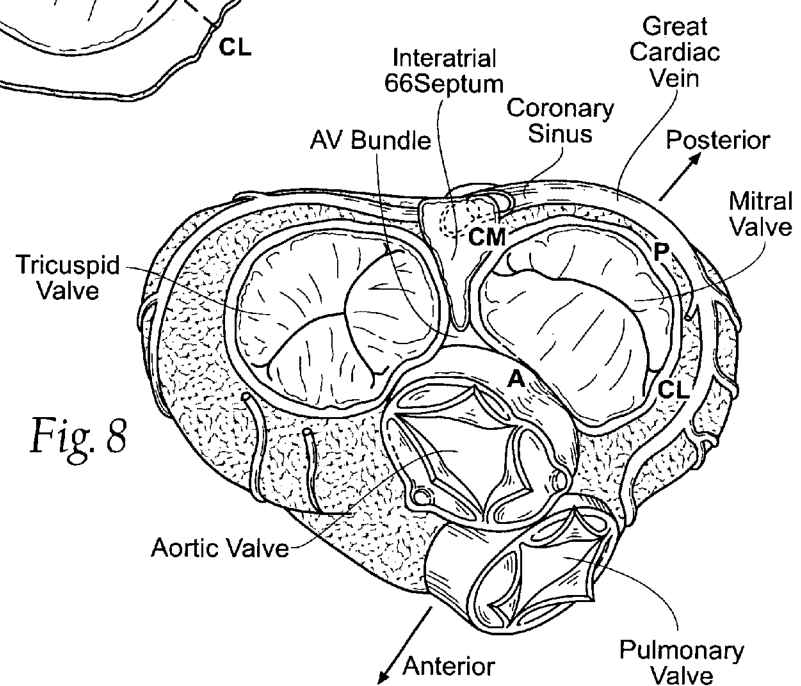
FIG. 8 is an anatomic superior view of a section of the human heart, with the normal mitral valve shown in FIG. 7 closed during ventricular systole (ventricular emptying) of the cardiac cycle.
Figure 9:
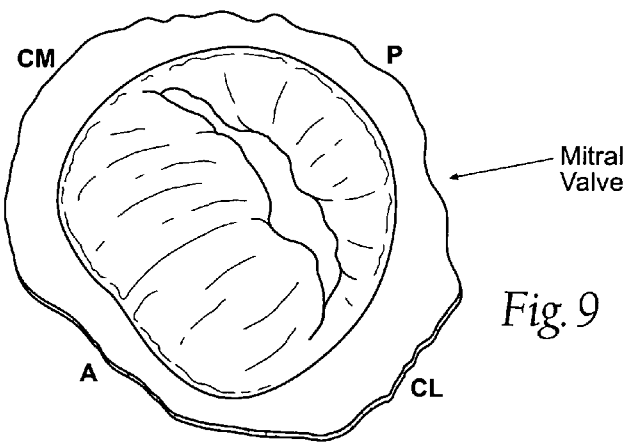
FIG. 9 is a superior view of a dysfunctional mitral valve, with the leaflets failing to coapt during peak contraction pressures during ventricular systole, leading to mitral regurgitation.

In use, the spanning region or bridging element 12 can be placed into tension between the two bridge stop regions 14 and 16. The implant 10 thereby serves to apply a direct mechanical force generally in a posterior to anterior direction across the left atrium. The direct mechanical force can serve to shorten the minor axis (line P-A in FIG. 7) of the annulus. In doing so, the implant 10 can also reactively reshape the annulus along its major axis (line CM-CL in FIG. 7) and/or reactively reshape other surrounding anatomic structures. It should be appreciated, however, the presence of the implant 10 can serve to stabilize tissue adjacent the heart valve annulus, without affecting the length of the minor or major axes.

It should also be appreciated that, when situated in other valve structures, the axes affected may not be the "major" and "minor" axes, due to the surrounding anatomy. In addition, in order to be therapeutic, the implant 10 may only need to reshape the annulus during a portion of the heart cycle, such as during late diastole and early systole when the heart is most full of blood at the onset of ventricular systolic contraction, when most of the mitral valve leakage occurs. For example, the implant 10 may be sized to restrict outward displacement of the annulus during late ventricular diastolic relaxation as the annulus dilates.

The mechanical force applied by the implant 10 across the left atrium can restore to the heart valve annulus and leaflets a more normal anatomic shape and tension. The more normal anatomic shape and tension are conducive to coaptation of the leaflets during late ventricular diastole and early ventricular systole, which, in turn, reduces mitral regurgitation.

In its most basic form, the implant 10 is made from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization.

The implant 10 can be formed by bending, shaping, joining, machining, molding, or extrusion of a metallic or polymer wire form structure, which can have flexible or rigid, or inelastic or elastic mechanical properties, or combinations thereof. Alternatively, the implant 10 can be formed from metallic or polymer thread-like or suture material. Materials from which the implant 10 can be formed include, but are not limited to, stainless steel, Nitinol, titanium, silicone, plated metals, Elgiloy™, NP55, and NP57.

The implant 10 can take various shapes and have various cross-sectional geometries. The implant 10 can have, e.g., a generally curvilinear (i.e., round or oval) cross-section, or a generally rectilinear cross section (i.e., square or rectangular), or combinations thereof. Shapes that promote laminar flow and therefore reduce hemolysis are contemplated, with features such as smoother surfaces and longer and narrower leading and trailing edges in the direction of blood flow.

B. The Posterior Bridge Stop Region

The posterior bridge stop region 14 is sized and configured to be located within or at the left atrium at a supra-annular position, i.e., positioned within or near the left atrium wall above the posterior mitral annulus.

In the illustrated embodiment, the posterior bridge stop region 14 is shown to be located generally at the level of the great cardiac vein, which travels adjacent to and parallel to the majority of the posterior mitral valve annulus. This tributary of the coronary sinus can provide a strong and reliable fluoroscopic landmark when a radio-opaque device is placed within it or contrast dye is injected into it. As previously described, securing the bridging element 12 at this supra-annular location also lessens the risk of encroachment of and risk of injury to the circumflex coronary artery compared to procedures applied to the mitral annulus directly. Furthermore, the supra-annular position assures no contact with the valve leaflets therefore allowing for coaptation and reduces the risk of mechanical damage.

The great cardiac vein also provides a site where relatively thin, non-fibrous atrial tissue can be readily augmented and consolidated. To enhance hold or purchase of the posterior bridge stop region 14 in what is essentially non-fibrous heart tissue, and to improve distribution of the forces applied by the implant 10, the posterior bridge stop region 14 may include a posterior bridge stop 18 placed within the great cardiac vein and abutting venous tissue. This makes possible the securing of the posterior bridge stop region 14 in a non-fibrous portion of the heart in a manner that can nevertheless sustain appreciable hold or purchase on that tissue for a substantial period of time, without dehiscence, expressed in a clinically relevant timeframe.

C. The Anterior Bridge Stop Region

The anterior bridge stop region 16 is sized and configured to allow the bridging element 12 to remain firmly in position adjacent or near the fibrous tissue and the surrounding tissues in the right atrium side of the atrial septum. The fibrous tissue in this region provides superior mechanical strength and integrity compared with muscle and can better resist a device pulling through. The septum is the most fibrous tissue structure in its own extent in the heart. Surgically handled, it is usually one of the only heart tissues into which sutures actually can be placed and can be expected to hold without pledgets or deep grasps into muscle tissue, where the latter are required.

As FIGS. 10A to 10C show, the anterior bridge stop region 16 passes through the septal wall at a supra-annular location above the plane of the anterior mitral valve annulus. The supra-annular distance on the anterior side can be generally at or above the supra-annular distance on the posterior side. As before pointed out, the anterior bridge stop region 16 is shown in FIGS. 10A to 10C at or near the inferior rim of the fossa ovalis, although other more inferior or more superior sites can be used within or outside the fossa ovalis, taking into account the need to prevent harm to the septal tissue and surrounding structures.

By locating the bridging element 12 at this supra-annular level within the right atrium, which is fully outside the left atrium and spaced well above the anterior mitral annulus, the implant 10 avoids the impracticalities of endovascular attachment at or adjacent to the anterior mitral annulus, where there is just a very thin rim of annulus tissue that is bounded anteriorly by the anterior leaflet, inferiorly by the aortic out-flow tract, and medially by the atrioventricular node of the conduction system. The anterior mitral annulus is where the non-coronary leaflet of the aortic valve attaches to the mitral annulus through the central fibrous body. Anterior location of the implant 10 in the supra-annular level within the right atrium (either in the septum or in a vena cava) avoids encroachment of and risk of injury to both the aortic valve and the AV node.

Figure 21A:
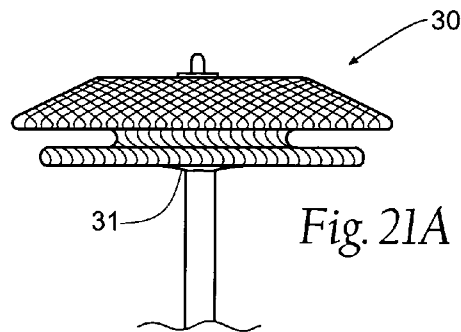
FIG. 21A is a side view of a septal member which may be used as part of the implant system of the type shown in FIGS. 10A and 10B.
Figure 21B:
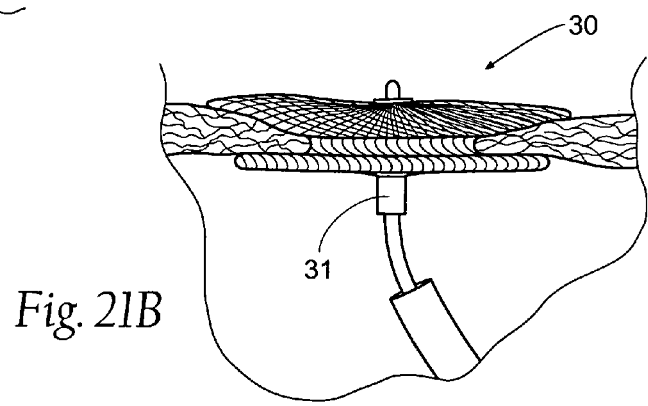
FIG. 21B is a side view of a deployed septal member of the type shown in FIG. 21A, showing the member sandwiching portions of the septum through an existing hole.

The purchase of the anterior bridge stop region 16 in fibrous septal tissue is desirably enhanced by a septal member 30 or an anterior bridge stop 20, or a combination of both. FIGS. 10A and 10B show the anterior bridge stop region including a septal member 30. FIG. 10C shows the anterior bridge stop region without a septal member. The septal member 30 may be an expandable device and also may be a commercially available device such as a septal occluder, e.g., Amplatzer® PFO Occluder (see FIGS. 21A and 21B). The septal member 30 preferably mechanically amplifies the hold or purchase of the anterior bridge stop region 16 in the fibrous tissue site. The septal member 30 also desirably increases reliance, at least partly, on neighboring anatomic structures of the septum to make firm the position of the implant 10. In addition, the septal member 30 may also serve to plug or occlude the small aperture that was created in the fossa ovalis or surrounding area during the implantation procedure.

Figure 11C:
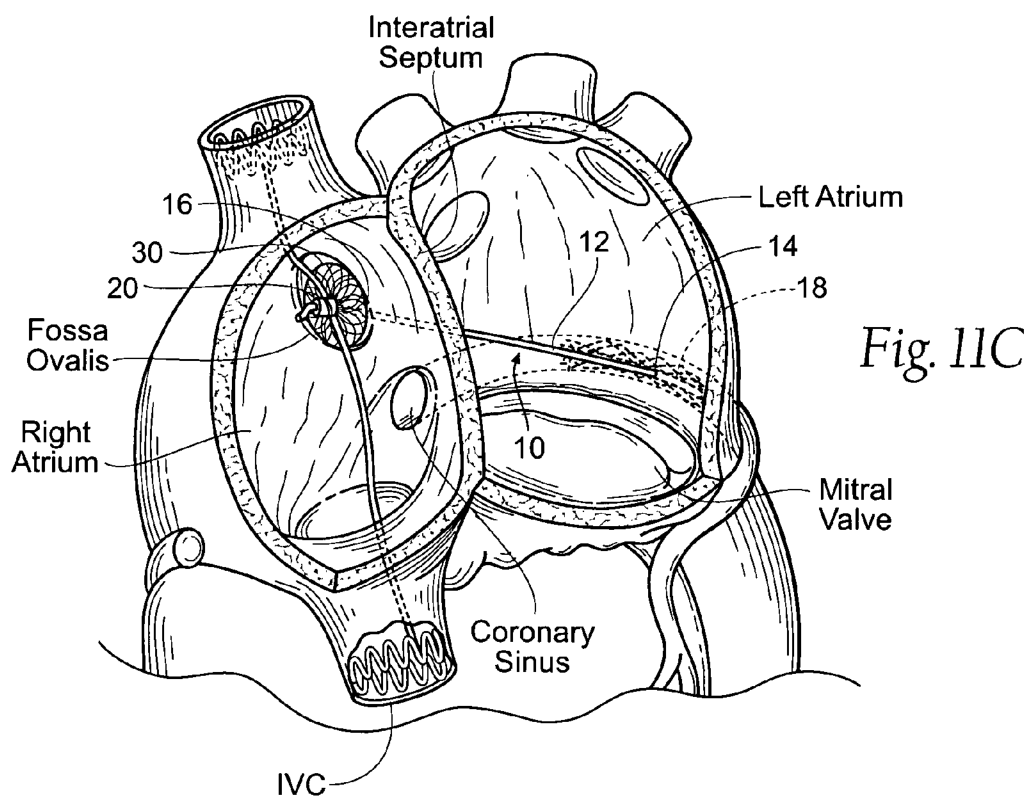
FIG. 11C is an anatomic anterior perspective view of the left and right atriums, with portions broken away and in section to show the presence of an implant system of the type shown in FIGS. 10A to 10C, with the anterior region of the implant situated on the inter-atrial septum, as well as in the superior vena cava and the inferior vena cava.

Anticipating that pinpoint pulling forces will be applied by the anterior bridge stop region 16 to the septum, the forces acting on the septal member 30 should be spread over a moderate area, without causing impingement on valve, vessels or conduction tissues. With the pulling or tensioning forces being transmitted down to the annulus, shortening of the minor axis is achieved. A flexurally stiff septal member is preferred because it will tend to cause less focal narrowing in the direction of bridge element tension of the left atrium as tension on the bridging element is increased. The septal member 30 should also have a low profile configuration and highly washable surfaces to diminish thrombus formation for devices deployed inside the heart. The septal member may also have a collapsed configuration and a deployed configuration. The septal member 30 may also include a hub 31 (see FIGS. 21A and 21B) to allow attachment of the bridge stop 20. A septal brace may also be used in combination with the septal member 30 and anterior bridge stop 20 to distribute forces uniformly along the septum (see FIG. 11C). Alternatively, devices in the IVC or the SVC can be used as bridge stop sites (see FIGS. 11A and 11B), instead of confined to the septum.

Location of the posterior and anterior bridge stop regions 14 and 16 having radio-opaque bridge locks and well demarcated fluoroscopic landmarks respectively at the supra-annular tissue sites just described, not only provides freedom from key vital structure damage or local impingement—e.g., to the circumflex artery, AV node, and the left coronary and non-coronary cusps of the aortic valve—but the supra-annular focused sites are also not reliant on purchase between tissue and direct tension-loaded penetrating/biting/holding tissue attachment mechanisms. Instead, physical structures and force distribution mechanisms such as stents, T-shaped members, and septal members can be used, which better accommodate the attachment or abutment of mechanical levers and bridge locks, and through which potential tissue tearing forces can be better distributed. Further, the bridge stop sites 14, 16 do not require the operator to use complex imaging. Adjustment of implant position after or during implantation is also facilitated, free of these constraints. The bridge stop sites 14, 16 also make possible full intra-atrial retrieval of the implant 10 by endovascularly snaring and then cutting the bridging element 12 at either side of the left atrial wall, from which it emerges.

D. Orientation of the Bridging Element

In the embodiments shown in FIGS. 10A to 10C, the implant 10 is shown to span the left atrium beginning at a posterior point of focus superior to the approximate midpoint of the mitral valve annulus, and proceeding in an anterior direction in a generally straight path directly to the region of anterior focus in the septum. As shown in FIGS. 10A to 10C, the spanning region or bridging element 12 of the implant 10 may be preformed or otherwise configured to extend in this essentially straight path above the plane of the valve, without significant deviation in elevation toward or away from the plane of the annulus, other than as dictated by any difference in elevation between the posterior and anterior regions of placement.

Lateral or medial deviations and/or superior or inferior deviations in this path can be imparted, if desired, to affect the nature and direction of the force vector or vectors that the implant 10 applies. It should be appreciated that the spanning region or bridging element 12 can be preformed or otherwise configured with various medial/lateral and/or inferior/superior deviations to achieve targeted annulus and/or atrial structure remodeling, which takes into account the particular therapeutic needs and morphology of the patient. In addition, deviations in the path of the bridging element may also be imparted in order to avoid the high velocity blood path within a heart chamber, such as the left atrium.

Figure 12:
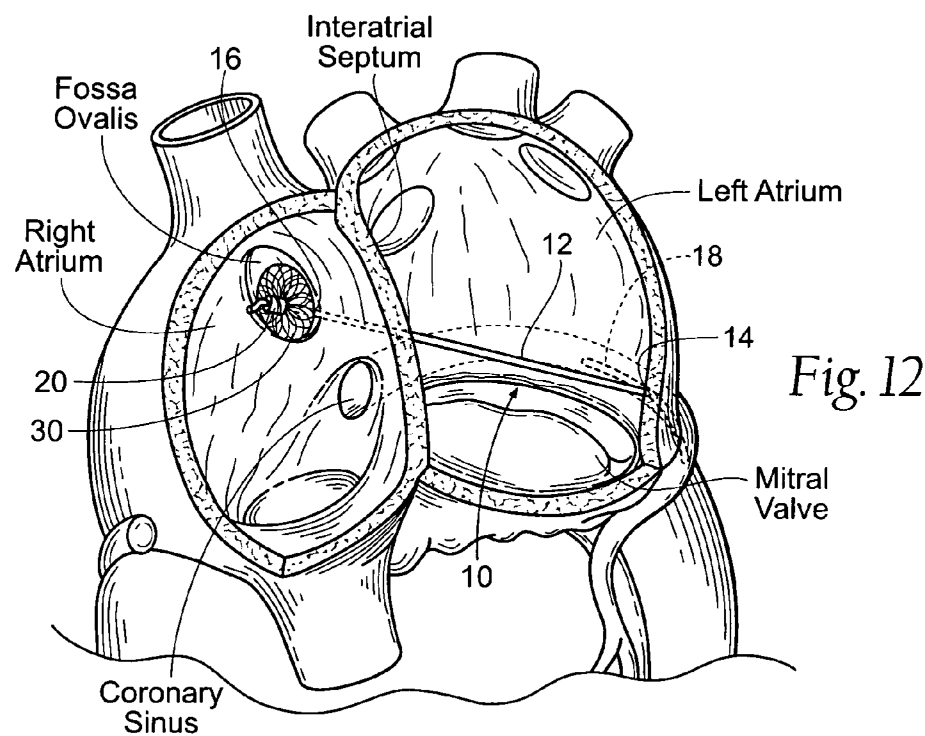
FIG. 12 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in an essentially straight path generally from a lateral region of the annulus.

For example, as shown in FIG. 12, the implant 10 is shown to span the left atrium beginning at a posterior region that is closer to a lateral trigone of the annulus (i.e., farther from the septum). Alternatively, the posterior region can be at a position that is closer to a medial trigone of the annulus (i.e., closer to the septum). From either one of these posterior regions, the implant 10 can extend in an anterior direction in a straight path directly to the anterior region in the septum. As shown in FIG. 12, like FIG. 10A, the spanning region or bridging element 12 of the implant 10 is preformed or otherwise configured to extend in an essentially straight path above the plane of the valve, without significant deviation in elevation toward or away from the plane of the annulus, other than as dictated by the difference in elevation, if any, between the posterior and anterior regions.

Figure 13:
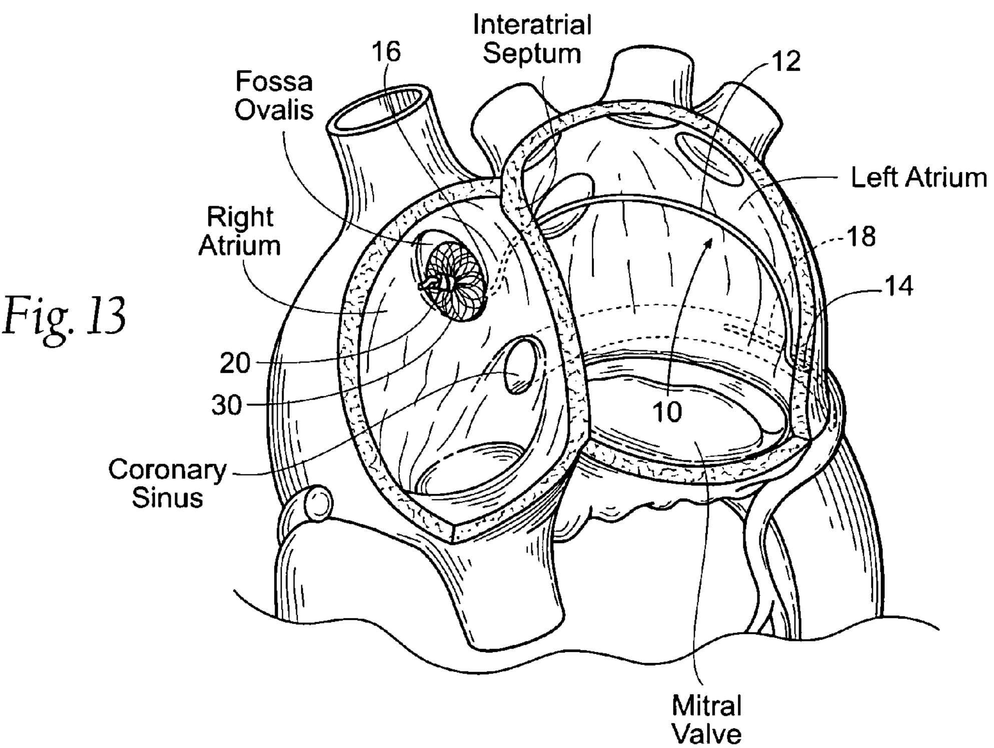
FIG. 13 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in an upwardly curved or domed path generally from a lateral region of the annulus.

Regardless of the particular location of the posterior region (see FIG. 13), the spanning region or bridging element 12 of the implant 10 can be preformed or otherwise configured to arch upward above the plane of the valve toward the dome of the left atrium Alternatively (see FIG. 14), the spanning region or bridging element 12 of the implant 10 can be preformed or otherwise configured to dip downward toward the plane of the valve toward the annulus, extending close to the plane of the valve, but otherwise avoiding interference with the valve leaflets. Or, still alternatively (see FIG. 15), the spanning region or bridging element 12 of the implant 10 can be preformed or otherwise configured to follow a curvilinear path, bending towards a trigone (medial or lateral) of the annulus before passage to the anterior region.

Figure 16:
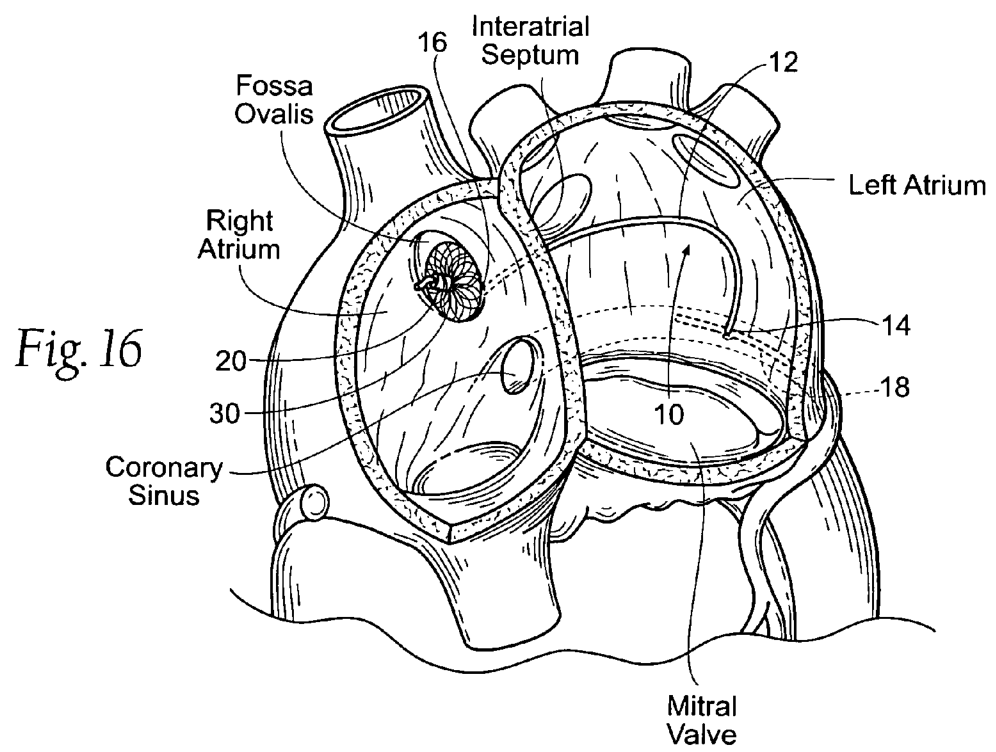
FIG. 16 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a curvilinear path, bending around a trigone of the annulus generally from a mid-region region of the annulus, as well as elevating in an arch toward the dome of the left atrium.
Figure 17:
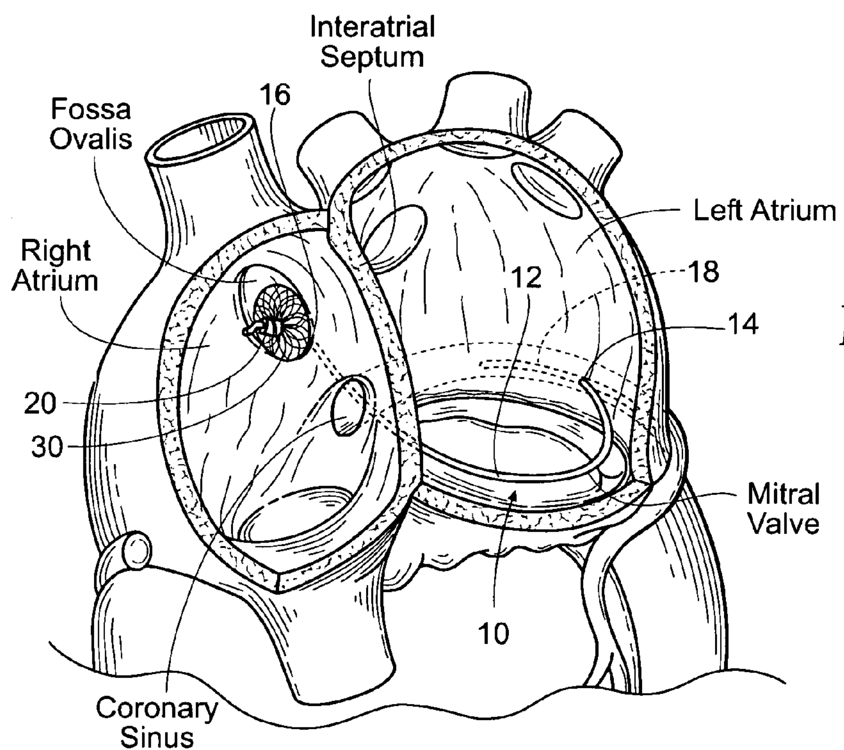
FIG. 17 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a curvilinear path, bending around a trigone of the annulus generally from a mid-region region of the annulus, as well as dipping downward toward the plane of the valve.

Various combinations of lateral/medial deviations and superior/inferior deviations of the spanning region or bridging element 12 of the implant 10 are of course possible. For example, as shown in FIG. 16, the spanning region or bridging element 12 can follow a curvilinear path bending around a trigone (medial or lateral) of the annulus as well as elevate in an arch away from the plane of the valve. Or, as shown in FIG. 17, the spanning region or bridging element 12 can follow a curvilinear path bending around a trigone (medial or lateral) of the annulus as well as dip toward the plane of the valve.

Figure 18:
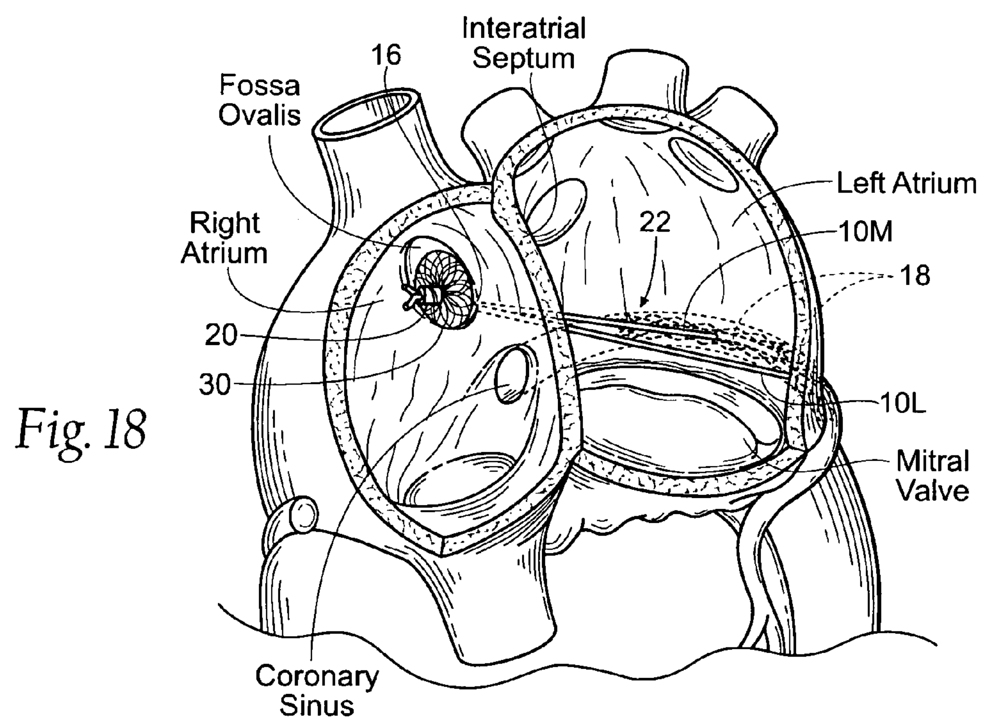
FIG. 18 is an anatomic anterior perspective view of the left and right atriums, with portions broken away and in section to show the presence of an implant system that includes two inter-atrial bridging elements that span the mitral valve annulus, each with a posterior bridge stop in the great cardiac vein and an anterior bridge stop on the inter-atrial septum, the inter-atrial bridging elements both extending in generally straight paths from different regions of the annulus.

Regardless of the orientation, more than one implant 10 can be installed to form an implant system 22. For example, FIG. 18 shows a system 22 comprising a lateral implant 10L and a medial implant 10M of a type consistent with the implant 10 as described. FIG. 18 shows the implants 10L and 10M being located at a common anterior bridge stop region 16. It should be appreciated that the implants 10L and 10M can also include spaced apart anterior bridge stop regions.

Figure 14:
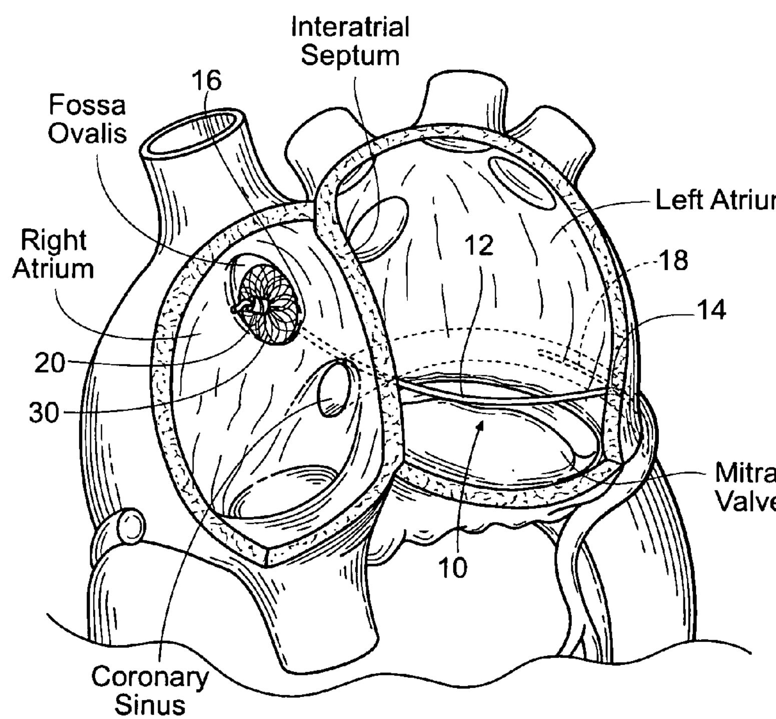
FIG. 14 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a downwardly curved path generally from a lateral region of the annulus.

One or both of the implants 10L and 10M can be straight (as in FIG. 12), or arch upward (as in FIG. 13), or bend downward (as in FIG. 14). A given system 10 can comprise lateral and medial implants 10L and 10M of different configurations. Also, a given system 22 can comprise more than two implants 10.

Figure 15:
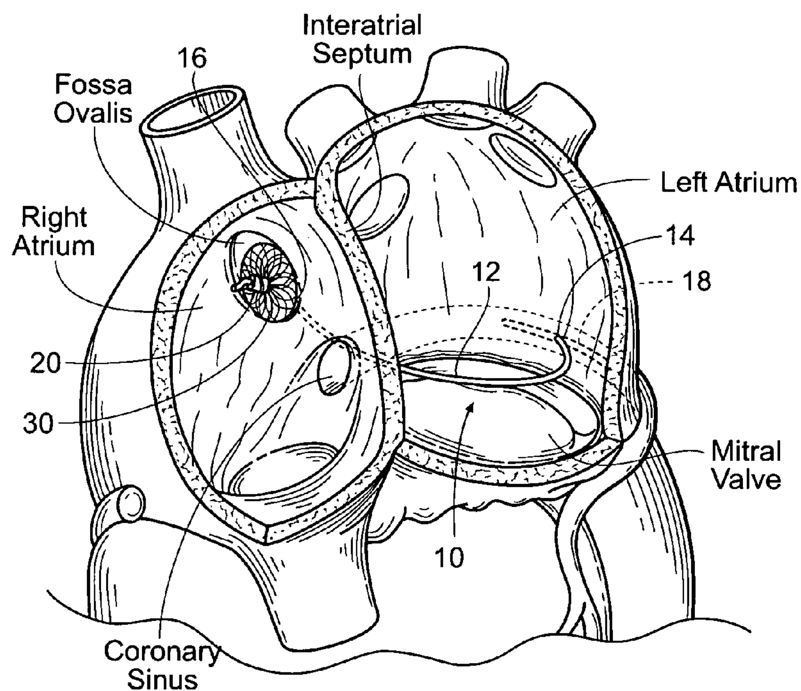
FIG. 15 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a curvilinear path, bending around a trigone of the annulus generally from a mid-region region of the annulus.
Figure 19:
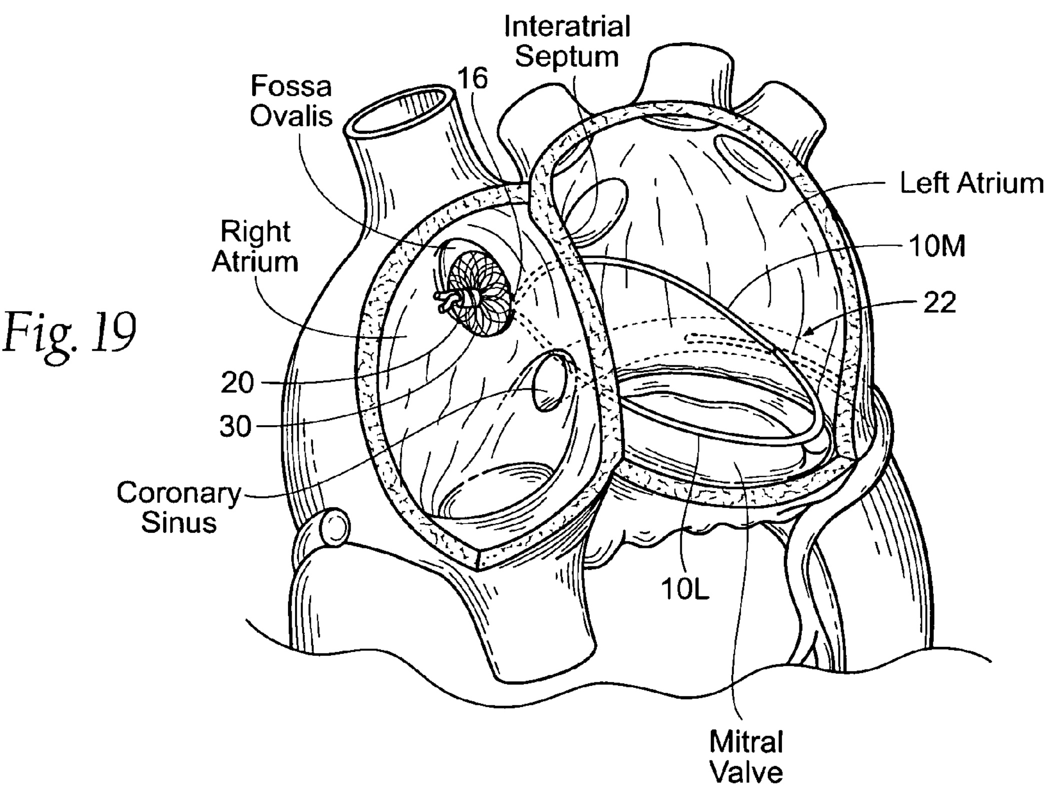
FIG. 19 is an anatomic anterior perspective view of the left and right atriums, with portions broken away and in section to show the presence of an implant system that includes two inter-atrial bridging elements that span the mitral valve annulus, each with a posterior region situated in the great cardiac vein and an anterior region situated on the interatrial septum, the inter-atrial bridging elements both extending in generally curvilinear paths from adjacent regions of the annulus.

FIG. 19 shows a system 22 comprising two curvilinear implants 10L and 10M of the type shown in FIG. 15. In FIG. 19, the curvilinear implants 10L and 10M are shown to be situated at a common posterior region, but the implants 10 can proceed from spaced apart posterior regions, as well. One or both of the curvilinear implants 10L and 10M can be parallel with respect to the plane of the valve (as in FIG. 15), or arch upward (as in FIG. 16), or bend downward (as in FIG. 17). A given system 22 can comprise curvilinear implants 10L and 10M of different configurations.

Figure 20:
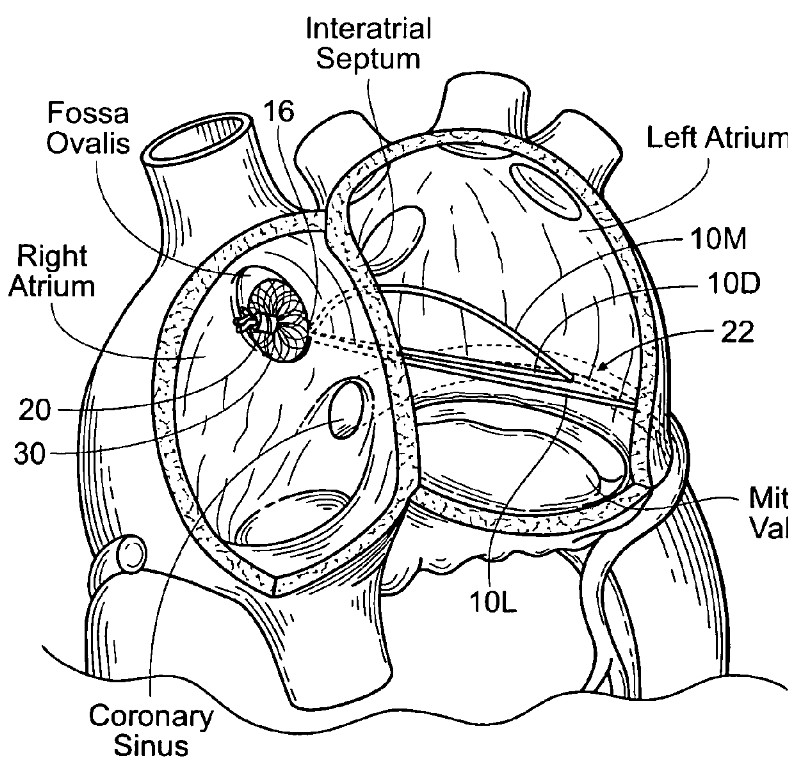
FIG. 20 is an anatomic anterior perspective view of the left and right atriums, with portions broken away and in section to show the presence of an implant system that includes three inter-atrial bridging elements that span the mitral valve annulus, each with a posterior region situated in the great cardiac vein and an anterior region situated on the interatrial septum, two of the inter-atrial bridging elements extending in generally straight paths from different regions of the annulus, and the third inter-atrial bridging elements extending in a generally curvilinear path toward a trigone of the annulus.

FIG. 20 shows a system 22 comprising a direct middle implant 10D, a medial curvilinear implant 10M, and a direct lateral implant 10L. One, two, or all of the implants 10 can be parallel to the valve, or arch upward, or bend downward, as previously described.

E. Posterior and Anterior Bridge Stop

Figure 22A:
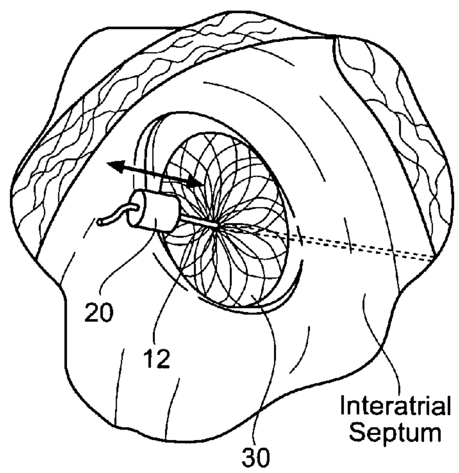
FIGS. 22A and 22B are sectional views showing the ability of a bridge stop used in conjunction with the implant shown in FIGS. 10A to 10C to move back and forth independent of the septal wall and inner wall of the great cardiac vein.
Figure 22B:
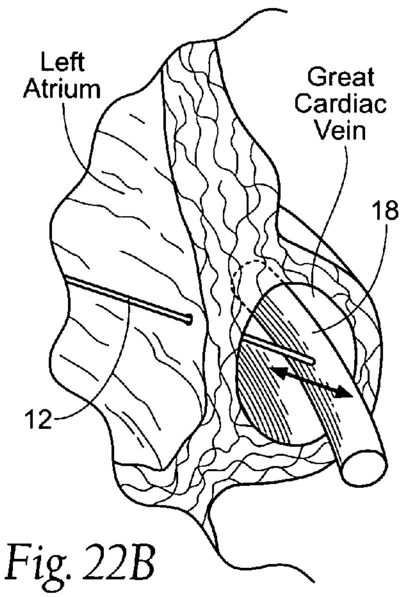

It is to be appreciated that a bridge stop as described herein, including a posterior or anterior bridge stop, describes an apparatus that may releasibly hold the bridging element 12 in a tensioned state. As can be seen in FIGS. 22A and 22B, bridge stops 20 and 18 respectively are shown releasibly secured to the bridging element 12, allowing the bridge stop structure to move back and forth independent of the inter-atrial septum and inner wall of the great cardiac vein during a portion of the cardiac cycle when the tension force may be reduced or becomes zero. Alternative embodiments are also described, all of which may provide this function. It is also to be appreciated that the general descriptions of posterior and anterior are non-limiting to the bridge stop function, i.e., a posterior bridge stop may be used anterior, and an anterior bridge stop may be used posterior.

When the bridge stop is in an abutting relationship to a septal member or a T-shaped member, for example, the bridge stop allows the bridging element to move freely within or around the septal member or T-shaped member, i.e., the bridging element is not connected to the septal member or T-shaped member. In this configuration, the bridging element is held in tension by the bridge stop, whereby the septal member or T-shaped member serves to distribute the force applied by the bridging element across a larger surface area. Alternatively, the bridge stop may be mechanically connected to the septal member or T-shaped member, e.g., when the bridge stop is positioned over and secured to the septal member hub. In this configuration, the bridging element is fixed relative to the septal member position and is not free to move about the septal member.

II. General Methods of Trans-Septal Implantation

The implants 10 or implant systems 22 as just described lend themselves to implantation in a heart valve annulus in various ways. The implants 10 or implant systems 22 can be implanted, e.g., in an open heart surgical procedure. Alternatively, the implants 10 or implant systems 22 can be implanted using catheter-based technology via a peripheral venous access site, such as in the femoral or jugular vein (via the IVC or SVC) under image guidance, or trans-arterial retrograde approaches to the left atrium through the aorta from the femoral artery also under image guidance.

Alternatively, the implants 10 or implant systems 22 can be implanted using thoracoscopic means through the chest, or by means of other surgical access through the right atrium, also under image guidance. Image guidance includes but is not limited to fluoroscopy, ultrasound, magnetic resonance, computed tomography, or combinations thereof.

The implants 10 or implant systems 22 may comprise independent components that are assembled within the body to form an implant, or alternatively, independent components that are assembled exterior the body and implanted as a whole.

FIGS. 23 to 30 show a representative embodiment of the deployment of an implant 10 of the type shown in FIGS. 10A to 10C by a percutaneous, catheter-based procedure, under image guidance.

Figure 23:
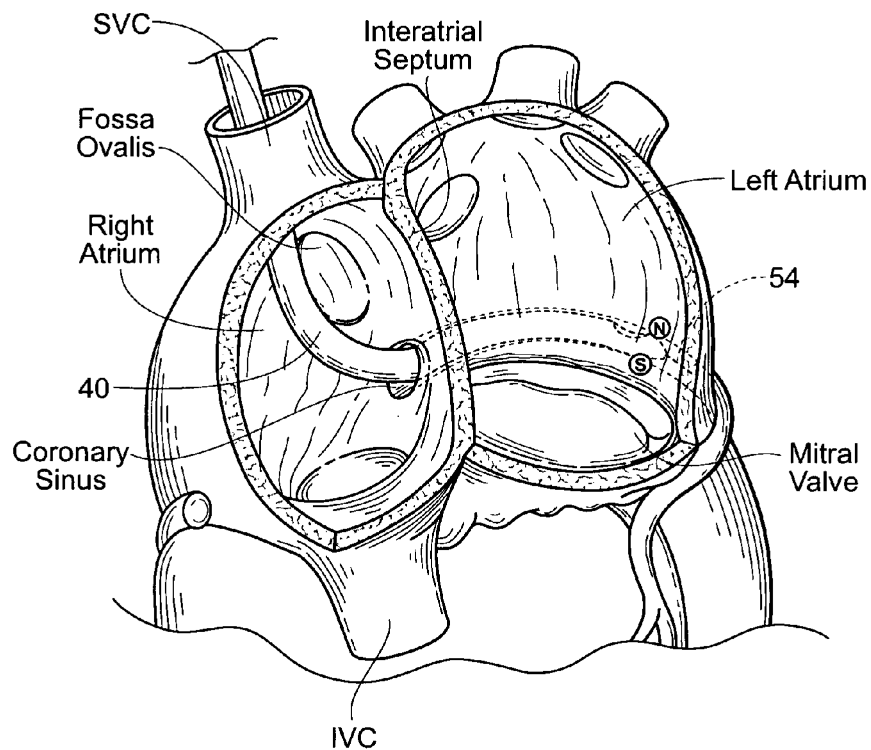
FIGS. 23 to 30 are anatomic views depicting representative catheter-based devices and steps for implanting an implant system of the type shown in FIGS. 10A to 10C.
Figure 24:
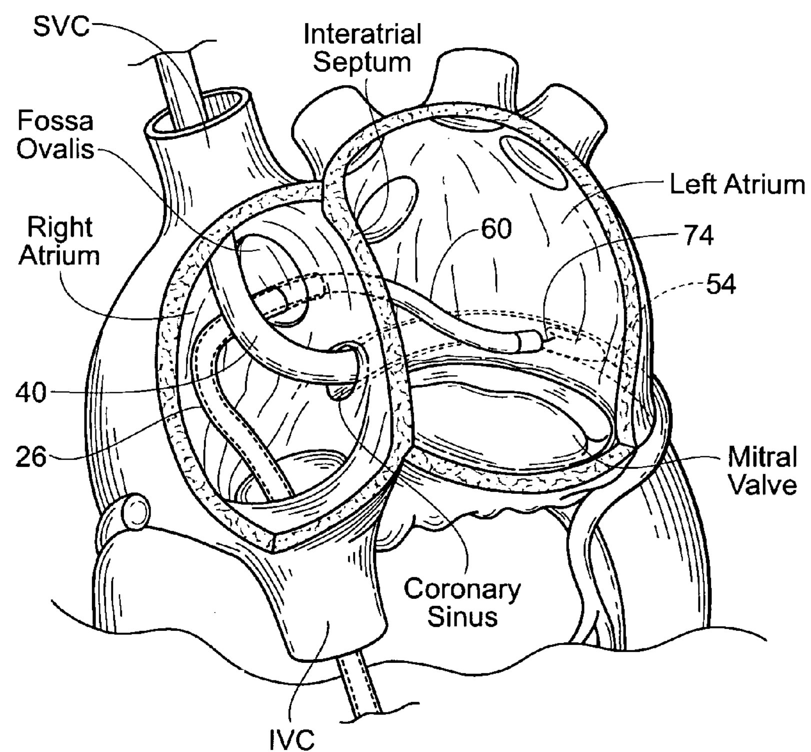

Percutaneous vascular access is achieved by conventional methods into the femoral or jugular vein, or a combination of both. As FIGS. 23 and 24 show, under image guidance, a first catheter, or great cardiac vein catheter 40, and a second catheter, or left atrium catheter 60, are steered through the vasculature into the right atrium. It is a function of the great cardiac vein (GCV) catheter 40 and left atrium (LA) catheter 60 to establish the posterior bridge end stop region. Catheter access to the right and left atriums can be achieved through either a femoral vein to IVC or SVC route (in the latter case, for a caval brace) or an upper extremity or neck vein to SVC or IVC route (in the latter case, for a caval brace). In the case of the SVC, the easiest access is from the upper extremity or neck venous system; however, the IVC can also be accessed by passing through the SVC and right atrium. Similarly the easiest access to the IVC is through the femoral vein; however the SVC can also be accessed by passing through the IVC and right atrium. FIGS. 23, 24, 27, 28 and 29 show access through both a SVC route and an IVC route for purposes of illustration.

The implantation of the implant 10 or implant systems 22 are first described here in four general steps. Each of these steps, and the various tools used, is then described with additional detail below in section III. Additionally, alternative implantation steps may be used and are described in section IV. Additional alternative embodiments of a bridge stop are described in section V, additional alternative embodiments of a T-shaped member or bridge stop are described in section VI, and additional alternative embodiments of an anterior bridge stop are described in section VII.

A first implantation step can be generally described as establishing the posterior bridge stop region 14. As can be seen in FIG. 24, the GCV catheter 40 is steered through the vasculature into the right atrium. The GCV catheter 40 is then steered through the coronary sinus and into the great cardiac vein. The second catheter, or LA catheter 60, is also steered through the vasculature and into the right atrium. The LA catheter 60 then passes through the septal wall at or near the fossa ovalis and enters the left atrium. A Mullins™ catheter 26 may be provided to assist the guidance of the LA catheter 60 into the left atrium. Once the GCV catheter 40 and the LA catheter 60 are in their respective positions in the great cardiac vein and left atrium, it is a function of the GCV and LA catheters 40, 60 to configure the posterior bridge stop region 14.

A second step can be generally described as establishing the trans-septal bridging element 12. A deployment catheter 24 via the LA catheter 60 is used to position a posterior bridge stop 18 and a preferably preattached and predetermined length of bridging element 12 within the great cardiac vein (see FIG. 27). The predetermined length of bridging element 12, e.g., two meters, extends from the posterior bridge stop 18, through the left atrium, through the fossa ovalis, through the vasculature, and preferably remains accessible exterior the body. The predetermined length of bridging element may be cut or detached in a future step, leaving implanted the portion extending from the posterior bridge stop 18 to the anterior bridge stop 20. Alternatively, the bridging element 20 may not be cut or detached at the anterior bridge stop 20, but instead the bridging element 20 may be allowed to extend into the IVC for possible future retrieval.

Figure 29:
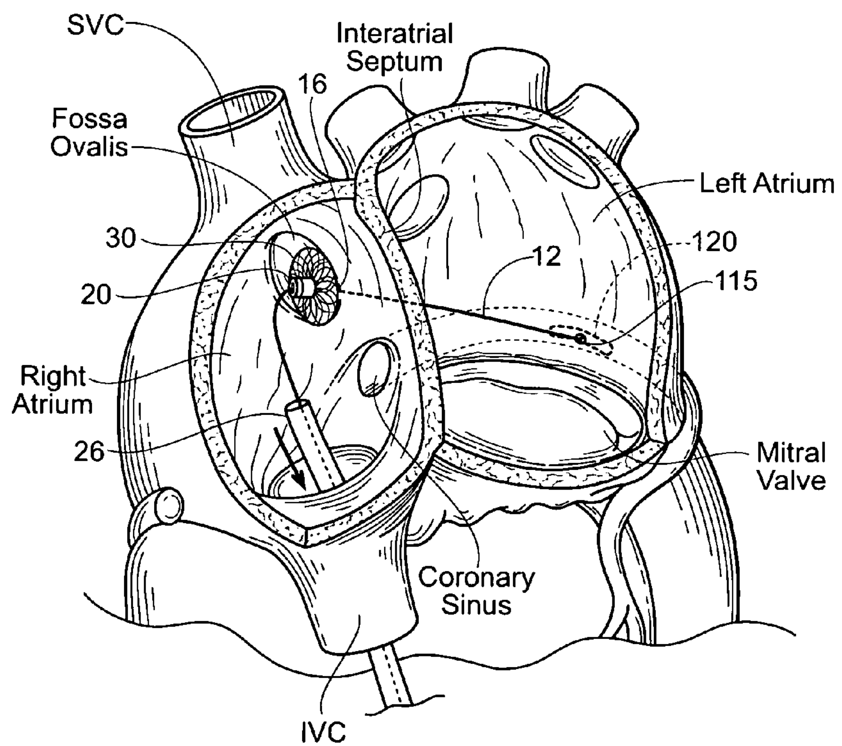

A third step can be generally described as establishing the anterior bridge stop region 16 (see FIG. 29). The bridging element 12 is first threaded through the septal member 30. The septal member 30 is then advanced over the bridging element 12 in a collapsed condition through Mullins catheter 26, and is positioned and deployed at or near the fossa ovalis within the right atrium. A bridge stop 20 may be attached to the bridging element 12 and advanced with the septal member 30, or alternatively, the bridge stop 20 may be advanced to the right atrium side of the septal member 30 after the septal member has been positioned or deployed.

A fourth step can be generally described as adjusting the bridging element 12 for proper therapeutic effects. With the posterior bridge stop region 14, bridging element 12, and anterior bridge stop region 16 configured as previously described, a tension is placed on the bridging element 12. The implant 10 and associated regions may be allowed to settle for a predetermined amount of time, e.g., five or more seconds. The mitral valve and mitral valve regurgitation are observed for desired therapeutic effects. The tension on the bridging element 12 may be adjusted until a desired result is achieved. The bridge stop 20 is then allowed to secure the bridging element 12 when the desired tension or measured length or degree of mitral regurgitation reduction is achieved.

III. Detailed Methods and Implantation Apparatus

The four generally described steps of implantation will now be described in greater detail, including the various tools and apparatus used in the implantation of the implant 10 or implant systems 22. An exemplary embodiment will describe the methods and tools for implanting an implant 10. These same or similar methods and tools may be used to implant an implant system 22 as well.

A. Establish Posterior Bridge Stop Region

1. Implantation Tools

Various tools may be used to establish the posterior bridge stop region 14. For example, the great cardiac vein (GCV) catheter 40, the left atrium (LA) catheter 60, and a cutting catheter 80 may be used.

FIG. 37A shows one embodiment of the GCV catheter 40 in accordance with the present invention. The GCV catheter 40 preferably includes a magnetic or ferromagnetic head 42 positioned on the distal end of the catheter shaft 45, and a hub 46 positioned on the proximal end. The catheter shaft 45 may include a first section 48 and a second section 50. The first section 48 may be generally stiff to allow for torquability of the shaft 45, and may be of a solid or braided construction. The first section 48 includes a predetermined length, e.g., fifty centimeters, to allow positioning of the shaft 45 within the vasculature structure. The second section 50 may be generally flexible to allow for steerability within the vasculature, i.e., into the coronary sinus. The second section 50 may also include a predetermined length, e.g., ten centimeters. The inner diameter or lumen 52 of the catheter shaft 45 is preferably sized to allow passage of a GCV guide wire 54, and additionally an LA guide wire 74 (see FIGS. 39 and 40). Both the GCV guide wire 54 and the LA guide wire 74 may be pre-bent, and both may be steerable. The GCV catheter 40 preferably includes a radio-opaque marker 56 to facilitate adjusting the catheter under image guidance to align with the LA catheter 60.

Figure 25:
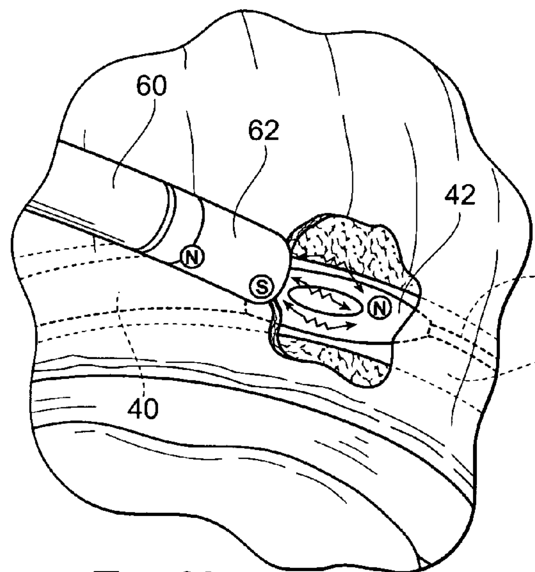

The magnetic or ferromagnetic head 42 is preferably polarized to magnetically attract or couple the distal end of the LA catheter 60 (see FIGS. 37B and 25). The head 42 includes a side hole 58 formed therein to allow for passage of the LA guide wire 74. As shown in FIG. 40, the left atrial side 43 of the head 42 has an attracting magnetic force, and the exterior of the heart side 44 of the head 42 has a repelling magnetic force. It should be appreciated that these magnetic forces may be reversed, as long as the magnetic forces in each catheter coincide with proper magnetic attraction. The magnetic head 42 preferably includes a bullet or coned shaped tip 55 to allow the catheter to track into the vasculature system. Within the tip 55 is an end hole 59, configured to allow for passage of the GCV guide wire 54.

FIG. 38 shows one embodiment of the LA catheter 60. Similar to the GCV catheter 40, the LA catheter 60 preferably includes a magnetic or ferromagnetic head 62 positioned on the distal end of the catheter shaft 65 and a hub 66 positioned on the proximal end. The catheter shaft 65 may include a first section 68 and a second section 70. The first section 68 may be generally stiff to allow for torquability of the shaft 65, and may be of a solid or braided construction. The first section 68 includes a predetermined length, e.g., ninety centimeters, to allow positioning of the shaft 65 within the vasculature structure. The second section 70 may be generally flexible and anatomically shaped to allow for steerability through the fossa ovalis and into the left atrium. The second section 70 may also include a predetermined length, e.g., ten centimeters. The inner diameter or lumen 72 of the catheter shaft 65 is preferably sized to allow passage of an LA guide wire 74, and additionally may accept the guide wire 54 passed from the GCV. The LA catheter 60 may include a radio-opaque marker 76 to facilitate adjusting the catheter 60 under image guidance to align with the GCV catheter 40.

The magnetic or ferromagnetic head 62 of the LA catheter 60 is polarized to magnetically attract or couple the distal end of the GCV catheter 40. As shown in FIG. 40, end side 64 of the head 62 is polarized to attract the GCV catheter head 42. The magnetic forces in the head 62 may be reversed, as long as attracting magnetic poles in the LA catheter 60 and the GCV catheter 40 are aligned. The magnetic head 62 preferably includes a generally planar tip 75, and also includes a center bore 78 sized for passage of the cutting catheter 80 and the LA guide wire 74 (see FIG. 38).

FIG. 41 shows the cutting catheter 80 preferably sized to be positioned within the inner diameter or lumen 72 of the LA catheter 60. Alternatively, the cutting catheter 80 may be positioned over the LA guide wire 74 with the LA catheter 60 removed.

The cutting catheter 80 preferably includes a hollow cutting tip 82 positioned on the distal end of the catheter shaft 85, and a hub 86 positioned on the proximal end. The catheter shaft 85 may include a first section 88 and a second section 90. The first section 88 may be generally stiff to allow for torquability of the shaft 85, and may be of a solid or braided construction. The first section 88 includes a predetermined length, e.g., ninety centimeters, to allow positioning of the shaft 85 within the vasculature structure and the LA catheter.

The second section 90 may be generally flexible to allow for steerability through the fossa ovalis and into the left atrium. The second section 90 may also include a predetermined length, e.g., twenty centimeters. The inner diameter 92 of the catheter shaft 85 is preferably sized to allow passage of the LA guide wire 74. The cutting catheter 80 preferably includes a radio-opaque marker 96 positioned on the shaft 85 so as to mark the depth of cut against the radio-opaque magnet head 62 or marker 76 of the LA catheter 60.

Figure 42A:
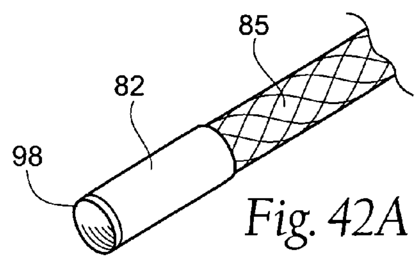
FIGS. 42A to 42C are partial perspective views of catheter tips which may be used with the catheter shown in FIG. 41.
Figure 42B:
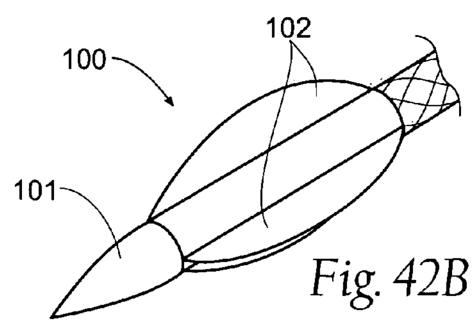
Figure 42C:
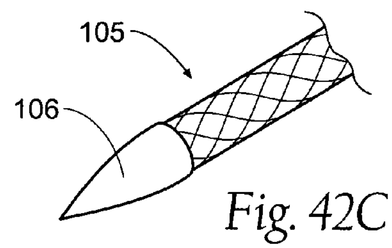

The hollow cutting or penetrating tip 82 includes a sharpened distal end 98 and is preferably sized to fit through the LA catheter 60 and magnetic head 62 (see FIG. 42A). Alternatively, as seen in FIGS. 42B and 42C, cutting or penetrating tips 100 and 105 may be used in place of, or in combination with, the hollow cutting tip 82. The tri-blade 100 of FIG. 42B includes a sharp distal tip 101 and three cutting blades 102, although any number of blades may be used. The tri-blade 100 may be used to avoid producing cored tissue, which may be a product of the hollow cutting tip 82. The elimination of cored tissue helps to reduce the possibility of an embolic complication. The sharp tipped guide wire 105 shown in FIG. 42C may also be used. The sharp tip 106 is positioned on the end of a guide wire to pierce the wall of the left atrium and great cardiac vein.

2. Implantation Methods

Figure 35A:
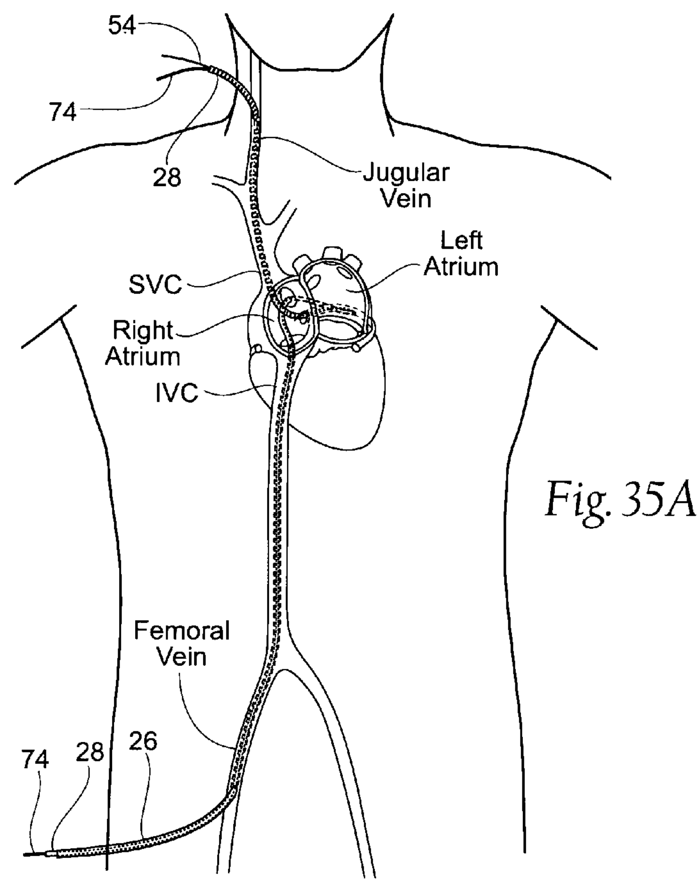
FIG. 35A is an anatomic partial view of a patient depicting access points used for implantation of an implant system, and also showing a loop guide wire accessible to the exterior the body at two locations.
Figure 36A:
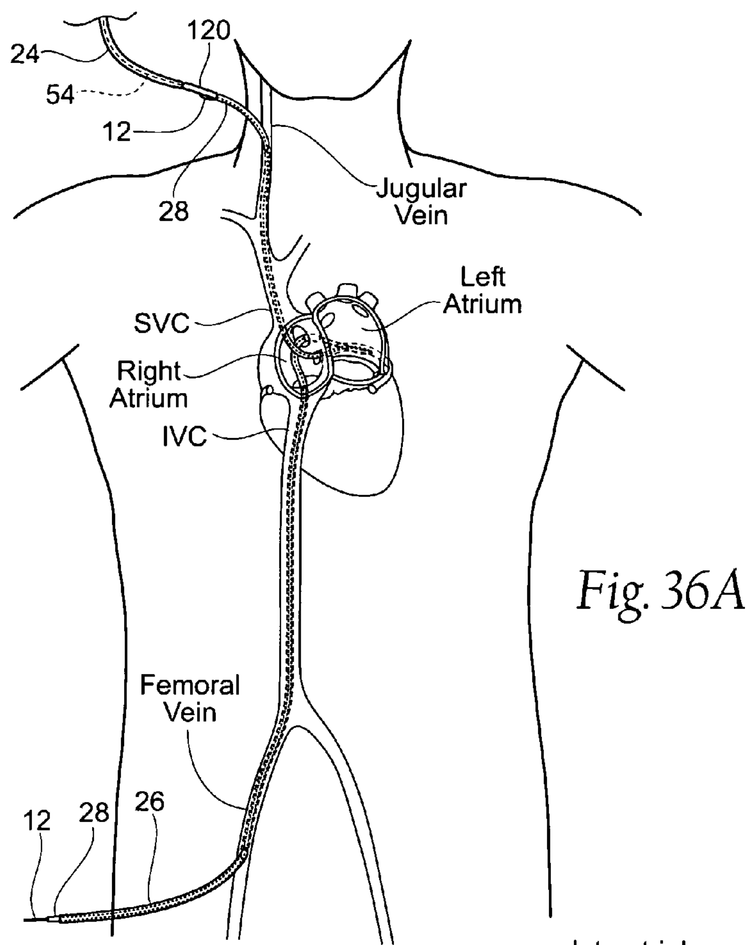
FIG. 36A is an anatomic partial view of a patient showing a bridge stop connected to a bridging element in preparation to be pulled and/or pushed through the vasculature structure and positioned within the great cardiac vein.

Access to the vascular system is commonly provided through the use of introducers known in the art. A 16F or less hemostasis introducer sheath (not shown), for example, may be first positioned in the superior vena cava (SVC), providing access for the GCV catheter 40. Alternatively, the introducer may be positioned in the subclavian vein. A second 16F or less introducer sheath (not shown) may then be positioned in the right femoral vein, providing access for the LA catheter 60. Access at both the SVC and the right femoral vein, for example, also allows the implantation methods to utilize a loop guide wire. For instance, in a procedure to be described later, a loop guide wire is generated by advancing the LA guide wire 74 through the vasculature until it exits the body and extends external the body at both the superior vena cava sheath and femoral sheath. The LA guide wire 74 may follow an intravascular path that extends at least from the superior vena cava sheath through the interatrial septum into the left atrium and from the left atrium through atrial tissue and through a great cardiac vein to the femoral sheath. The loop guide wire enables the physician to both push and pull devices into the vasculature during the implantation procedure (see FIGS. 35A and 36A).

An optional step may include the positioning of a catheter or catheters within the vascular system to provide baseline measurements. An AcuNav™ intracardiac echocardiography (ICE) catheter (not shown), or similar device, may be positioned via the right femoral artery or vein to provide measurements such as, by way of non-limiting examples, a baseline septal-lateral (S-L) separation distance measurement, atrial wall separation, and a mitral regurgitation measurement. Additionally, the ICE catheter may be used to evaluate aortic, tricuspid, and pulmonary valves, IVC, SVC, pulmonary veins, and left atrium access.

The GCV catheter is then deployed in the great cardiac vein adjacent a posterior annulus of the mitral valve. From the SVC, under image guidance, the 0.035 inch GCV guide wire 54, for example, is advanced into the coronary sinus and to the great cardiac vein. Optionally, an injection of contrast with an angiographic catheter may be made into the left main artery from the aorta and an image taken of the left coronary system to evaluate the position of vital coronary arterial structures. Additionally, an injection of contrast may be made to the great cardiac vein in order to provide an image and a measurement. If the great cardiac vein is too small, the great cardiac vein may be dilated with a 5 to 12 millimeter balloon, for example, to midway the posterior leaflet. The GCV catheter 40 is then advanced over the GCV guide wire 54 to a location in the great cardiac vein, for example near the center of the posterior leaflet or posterior mitral valve annulus (see FIG. 23). The desired position for the GCV catheter 40 may also be viewed as approximately 2 to 6 centimeters from the anterior intraventricular vein takeoff. Once the GCV catheter 40 is positioned, an injection may be made to confirm sufficient blood flow around the GCV catheter 40. If blood flow is low or non-existent, the GCV catheter 40 may be pulled back into the coronary sinus until needed.

The LA catheter 60 is then deployed in the left atrium. From the femoral vein, under image guidance, the 0.035 inch LA guide wire 74, for example, is advanced into the right atrium. A 7F Mullins™ dilator with a trans-septal needle is deployed into the right atrium (not shown). An injection is made within the right atrium to locate the fossa ovalis on the septal wall. The septal wall at the fossa ovalis is then punctured with the trans-septal needle and the guide wire 74 is advanced into the left atrium. The trans-septal needle is then removed and the dilator is advanced into the left atrium. An injection is made to confirm position relative to the left ventricle. The 7F Mullins system is removed and then replaced with a 12F or other appropriately sized Mullins system 26. The 12F Mullins system 26 is positioned within the right atrium and extends a short distance into the left atrium.

As seen in FIG. 24, the LA catheter 60 is next advanced over the LA guide wire 74 and positioned within the left atrium. If the GCV catheter 40 had been backed out to allow for blood flow, it is now advanced back into position. The GCV catheter 40 is then grossly rotated to magnetically align with the LA catheter 60. Referring now to. FIG. 25, preferably under image guidance, the LA catheter 60 is advanced and rotated if necessary until the magnetically attractant head 62 of the LA catheter 60 magnetically attracts to the magnetically attractant head 42 of the GCV catheter 40. The left atrial wall and the great cardiac vein venous tissue separate the LA catheter 60 and the GCV catheter 40. The magnetic attachment is preferably confirmed via imaging from several viewing angles, if necessary.

Figure 26:
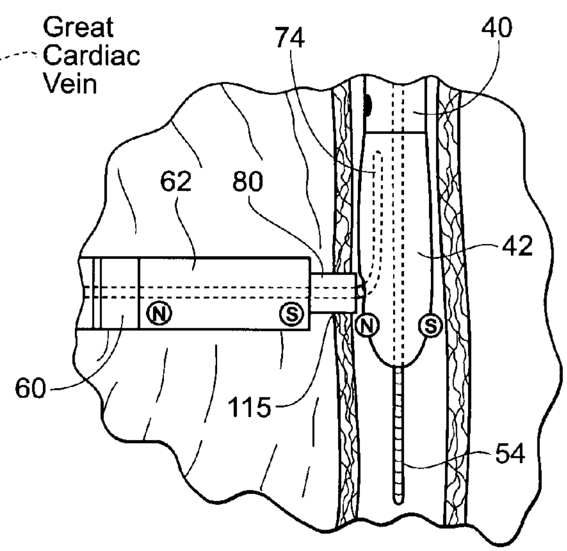

Next, an access lumen 115 is created into the great cardiac vein (see FIG. 26). The cutting catheter 80 is first placed over the LA guide wire 74 inside of the LA catheter 60. The cutting catheter 80 and the LA guide wire 74 are advanced until resistance is felt against the wall of the left atrium. The LA guide wire 74 is slightly retracted, and while a forward pressure is applied to the cutting catheter 80, the cutting catheter 80 is rotated and/or pushed. Under image guidance, penetration of the cutting catheter 80 into the great cardiac vein is confirmed. The LA guide wire 74 is then advanced into the great cardiac vein and further into the GCV catheter 40 toward the coronary sinus, eventually exiting the body at the sheath in the neck. The LA catheter 60 and the GCV catheter 40 may now be removed. Both the LA guide wire 74 and the GCV guide wire 54 are now in position for the next step of establishing the trans-septal bridging element 12.

B. Establish Trans-Septal Bridging Element

Now that the posterior bridge stop region 14 has been established, the trans-septal bridging element 12 is positioned to extend from the posterior bridge stop region 14 in a posterior to anterior direction across the left atrium and to the anterior bridge stop region 16.

In this exemplary embodiment of the methods of implantation, the trans-septal bridging element 12 is implanted via a left atrium to GCV approach. In this approach, the GCV guide wire 54 is not utilized and may be removed. Alternatively, a GCV to left atrium approach is also described. In this approach, the GCV guide wire is utilized. The alternative GCV to left atrium approach for establishing the trans-septal bridging element 12 will be described in detail in section IV.

The bridging element 12 may be composed of a suture material or suture equivalent known in the art. Common examples may include, but are not limited to, 1-0, 2-0, and 3-0 polyester suture, stainless steel braid (e.g., 0.022 inch diameter), and NiTi wire (e.g., 0.008 inch diameter). Alternatively, the bridging element 12 may be composed of biological tissue such as bovine, equine or porcine pericardium, or preserved mammalian tissue, preferably in a gluteraldehyde fixed condition. Alternatively the bridging element 12 may be encased by pericardium, or polyester fabric or equivalent.

Figure 43A:
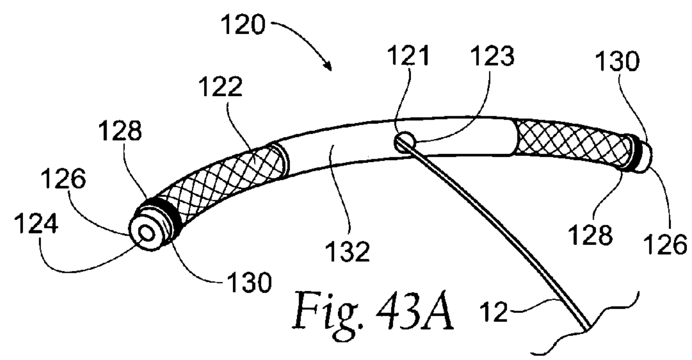
FIG. 43A is a perspective view of a symmetrically shaped T-shaped bridge stop or member which may be used with the implant system of the type shown in FIGS. 10A to 10C.
Figure 43B:
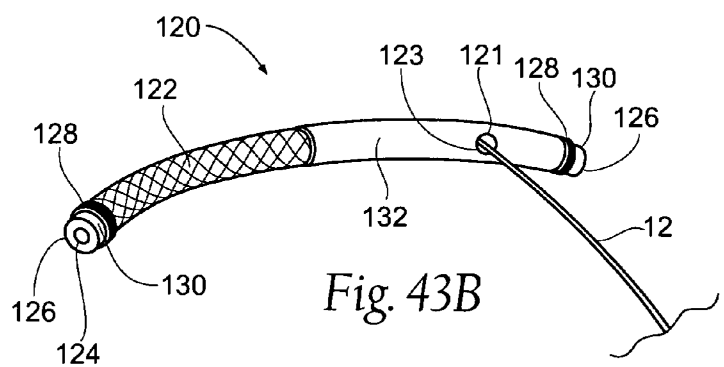
FIG. 43B is a perspective view of an alternative embodiment of the T-shaped bridge stop shown in FIG. 43A, showing the bridge stop being asymmetric and having one limb shorter than the other.

A bridge stop, such as a T-shaped bridge stop 120 is preferably connected to the predetermined length of the bridging element 12. The bridging element 12 may be secured to the T-shaped bridge stop 120 through the use of a bridge stop 150 (see FIG. 44A), or may be connected to the T-shaped bridge stop 120 by securing means 121, such as tying, welding, or gluing, or any combination thereof. As seen in FIGS. 43A and 43B, the T-shaped bridge stop 120 may be symmetrically shaped or asymmetrically shaped, may be curved or straight, and preferably includes a flexible tube 122 having a predetermined length, e.g., three to eight centimeters, and an inner diameter 124 sized to allow at least a guide wire to pass through. The tube 122 is preferably braided, but may be solid as well, and may also be coated with a polymer material. Each end 126 of the tube 122 preferably includes a radio-opaque marker 128 to aid in locating and positioning the T-shaped bridge stop 120. The tube 122 also preferably includes atraumatic ends 130 to protect the vessel walls. The T-shaped bridge stop 120 may be flexurally curved or preshaped so as to generally conform to the curved shape of the great cardiac vein or interatrial septum and be less traumatic to surrounding tissue. The overall shape of the T-shaped bridge stop 120 may be predetermined and based on a number of factors, including, but not limited to the length of the bridge stop, the material composition of the bridge stop, and the loading to be applied to the bridge stop.

A reinforcing center tube 132 may also be included with the T-shaped bridge stop 120. The reinforcing tube 132 may be positioned over the flexible tube 122, as shown, or, alternatively, may be positioned within the flexible tube 122. The reinforcing tube 132 is preferably solid, but may be braided as well, and may be shorter in length, e.g., one centimeter, than the flexible tube 122. The reinforcing center tube 132 adds stiffness to the T-shaped bridge stop 120 and aids in preventing egress of the T-shaped member 120 through the cored or pierced lumen 115 in the great cardiac vein and left atrium wall.

Alternative T-shaped members or bridge locks and means for connecting the bridging element 12 to the T-shaped bridge locks are described in section VI.

Figure 27:
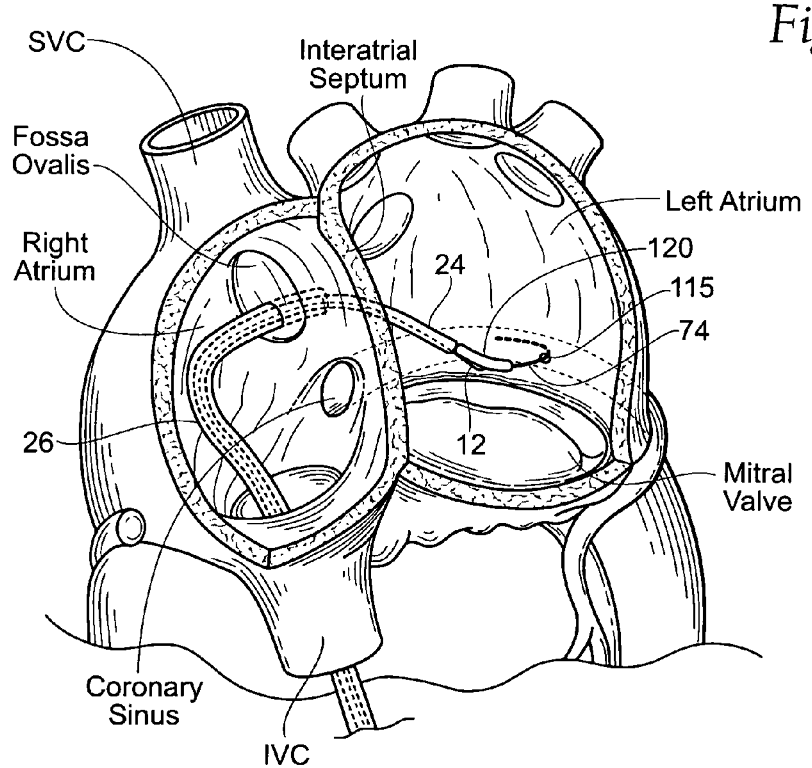

As can be seen in FIG. 27, the T-shaped bridge stop 120 (connected to the leading end of the bridging element 12) is first positioned onto or over the LA guide wire 74. The deployment catheter 24 is then positioned onto the LA guide wire 74 (which remains in position and extends into the great cardiac vein) and is used to push the T-shaped bridge stop 120 through the Mullins catheter 26 and into the right atrium, and from the right atrium through the interatrial septum into the left atrium, and from the left atrium through atrial tissue into a region of the great cardiac vein adjacent the posterior mitral valve annulus. The LA guide wire 74 is then withdrawn proximal to the tip of the deployment catheter 24. The deployment catheter 24 and the guide wire 74 are then withdrawn just to the left atrium wall. The T-shaped bridge stop 120 and the attached bridging element 12 remain within the great cardiac vein. The length of bridging element 12 extends from the posterior T-shaped bridge stop 120, through the left atrium, through the fossa ovalis, through the vasculature, and preferably the trailing end remains accessible exterior the body. Preferably under image guidance, the trailing end of the bridging element 12 is gently pulled, letting the T-shaped bridge stop 120 separate from the deployment catheter 24. Once separation is confirmed, again the bridging element 12 is gently pulled to position the T-shaped bridge stop 120 against the venous tissue within the region of the great cardiac vein and centered over the great cardiac vein access lumen 115. The deployment catheter 24 and the guide wire 74 may then be removed (see FIG. 28).

The trans-septal bridging element 12 is now in position and extends in a posterior to anterior direction from the posterior bridge stop region 14, across the left atrium, and to the anterior bridge stop region 16. The bridging element 12 preferably extends through the vasculature structure and extends exterior the body.

C. Establish Anterior Bridge Stop Region

Now that the trans-septal bridging element 12 is in position, the anterior bridge stop region 16 is next to be established.

In one embodiment, the proximal portion or trailing end of the bridging element 12 extending exterior the body is then threaded through or around an anterior bridge stop, such as the septal member 30. Preferably, the bridging element 12 is passed through the septal member 30 outside of the body nearest its center so that, when later deployed over the fossa ovalis, the bridging element 12 transmits its force to a central point on the septal member 30, thereby reducing twisting or rocking of the septal member. The septal member is advanced over the bridging element 12 in a collapsed configuration through the Mullins catheter 26, and is positioned within the right atrium and deployed at the fossa ovalis and in abutment with interatrial septum tissue. The bridging element 12 may then be held in tension by way of a bridge stop 20 (see FIGS. 29 and 30). The anterior bridge stop 20 may be attached to or positioned over the bridging element 12 and advanced with the septal member 30, or alternatively, the bridge stop 20 may be advanced over the bridging element 12 to the right atrium side of the septal member 30 after the septal member has been positioned or deployed. Alternatively, the bridge stop 20 may also be positioned over the LA guide wire 74 and pushed by the deployment catheter 24 into the right atrium. Once in the right atrium, the bridge stop 20 may then be attached to or positioned over the bridging element 12, and the LA guide wire 74 and deployment catheter 24 may then be completely removed from the body.

Figure 44A:
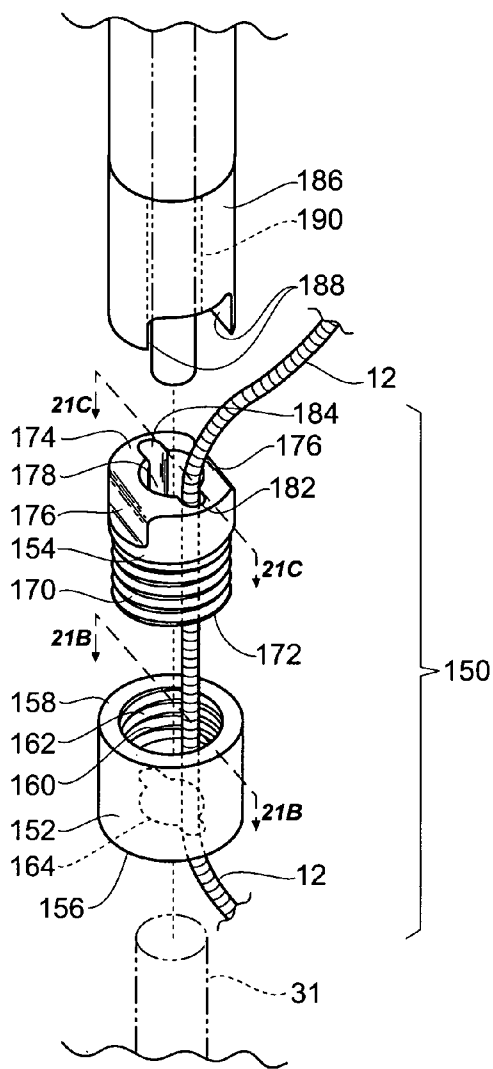
FIG. 44A is an exploded view of a bridge stop and associated driver which may be used with the implant system of the type shown in FIGS. 10A to 10C.
Figure 44B:
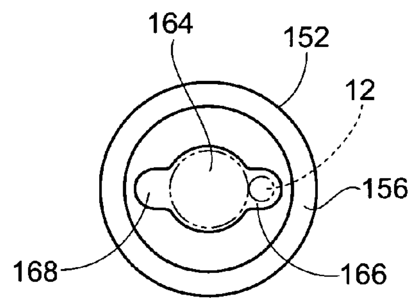
FIG. 44B is a bottom view of the bridge stop shown in FIG. 44A.

FIG. 44A is an exploded view of one embodiment of a bridge stop in accordance with the present invention. The bridge stop 150 preferably includes a tube shaped base 152 and a screw 154. The base 152 includes a first side 156 and a second side 158, wherein use, the first side 156 is disposed toward the septal member 30, or optionally, the first side is disposed over the septal member hub 31, and the second side 158 is adapted to receive the screw 154. The base 152 includes an axially configured bore 160 formed therein having threads 162 beginning at the second side 158 and extending partially within a length of the base 152, although the bore 160 may be threaded throughout its entire length. The threaded bore 160 includes a predetermined inner diameter 164, sized so as to allow the base 152 to be installed over a guide wire, and optionally, positioned over the septal member hub 31. A first channel 166 and, optionally, a second channel 168 may be included within the bore 160 extending from the first side 156 to partially within the base 152 to provide for passage of the bridging element 12 within the bridge stop 150 (see FIG. 44B).

Figure 44C:
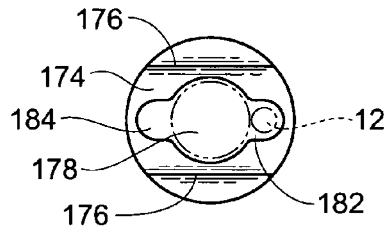
FIG. 44C is a top view of a screw used in the bridge stop of the type shown in FIG. 44A.

A male threaded portion 170 of screw 154 extends from the screw base 172 to approximately midway the length of the screw 154 and is sized to be threadably received within the bore 160 of the base 152. The screw head 174 preferably includes torquing means such as parallel surfaces 176. Surfaces 176 are provided to allow the screw 154 to be tightened and loosened within the base 152. Screw 154 also includes a bore 178 formed therein, sized so as to allow the screw 154 to be installed over a guide wire, and optionally, positioned over the septal member hub 31. A first channel 182 and, optionally, a second channel 184 may be included within the screw bore 178 extending partially within the screw 154, or alternatively, throughout the entire length of the screw 154 (see FIG. 44C). The base 152 and the screw 154 are aligned such that the channel provides for free passage of the bridging element 12 within the bridge stop 150.

In use, the screw 154 is first partially screwed into the base 152, allowing the channel 166, 168 in the base 152 to mate with the channel 182, 184 in the screw 154. The bridging element 12 is then extended through the entire length of the bridge stop 150, and is positioned within the channel formed within the base 152 and the screw 154. The bridging element 12 is then tensioned and the screw 154 is torqued into the base using a driver 186, such that the bridging element 12 is spooled within the bridge stop 150 or around the septal member hub 31, preferably one or more times. When the screw 154 is torqued into the base all the way, the screw compresses against the bridging element 12, preventing any relative motion of the bridging element. The bridging element 12 can no longer move freely within the bridge stop 150, fixing the position of the bridge stop 150 on the bridging element 12.

The driver 186 includes parallel surfaces 188, which are configured to extend over the screw head 174 in a mating relationship with parallel surfaces 176 on the screw head 174. The driver 186 also includes a bore 190 formed therein, sized so as to allow the driver 186 to be positioned over a guide wire.

The bridge stop 150, and alternative embodiments to be described later, have a predetermined size, e.g., eight millimeters by eight millimeters, allowing them to be positioned adjacent a septal member or a T-shaped member, for example. The bridge locks are also preferably made of stainless steel or other biocompatible metallic or polymer materials suitable for implantation.

Additional alternative bridge stop embodiments are described in section V.

D. Bridging Element Adjustment

The anterior bridge stop 20 is preferably positioned in an abutting relationship to the septal member 30, or optionally may be positioned over the septal member hub 31. The bridge stop 20 serves to adjustably stop or hold the bridging element 12 in a tensioned state to achieve proper therapeutic effects.

With the posterior bridge stop region 14, bridging element 12, and anterior bridge stop region 16 configured as previously described, a tension may be applied to the bridging element 12, either external to the body at the proximal portion of the bridging element 12, or internally, including within the vasculature structure and the heart structure. After first putting tension on the bridging element 12, the implant 10 and associated regions may be allowed to settle for a predetermined amount of time, e.g., five seconds. The mitral valve and its associated mitral valve regurgitation are then observed for desired therapeutic effects. The tension on the bridging element 12 may be repeatably adjusted following these steps until a desired result is achieved. The bridge stop 20 is then allowed to secure the desired tension of the bridging element 12. The bridging element may then be cut or detached at a predetermined distance away from the bridge stop 20, e.g., zero to three centimeters into the right atrium. The remaining length of bridging element 12 may then be removed from the vasculature structure.

Alternatively, the bridging element 12 may be allowed to extend into the IVC and into the femoral vein, possibly extending all the way to the femoral access point. Allowing the bridging element to extend into the IVC and into the femoral vein would allow for retrieval of the bridging element in the future, for example, if adjustment of the bridging element is necessary or desired.

The bridging element adjustment procedure as just described including the steps of placing a tension, waiting, observing, and readjusting if necessary is preferred over a procedure including adjusting while at the same time—or real-time—observing and adjusting, such as where a physician places a tension while at the same time observes a real-time ultrasound image and continues to adjust based on the real-time ultrasound image. The waiting step is beneficial because it allows for the heart and the implant to go through a quiescent period. This quiescent period allows the heart and implant to settle down and allows the tension forces and devices in the posterior and anterior bridge stop regions to begin to reach an equilibrium state. The desired results are better maintained when the heart and implant are allowed to settle prior to securing the tension compared to when the mitral valve is viewed and tension adjusted real-time with no settle time provided before securing the tension.

Figure 31:
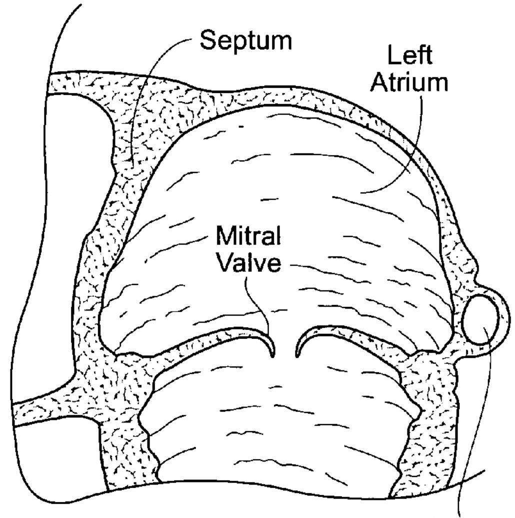
FIG. 31 is an anatomic section view of the left atrium and associated mitral valve structure, showing mitral dysfunction.
Figure 32:
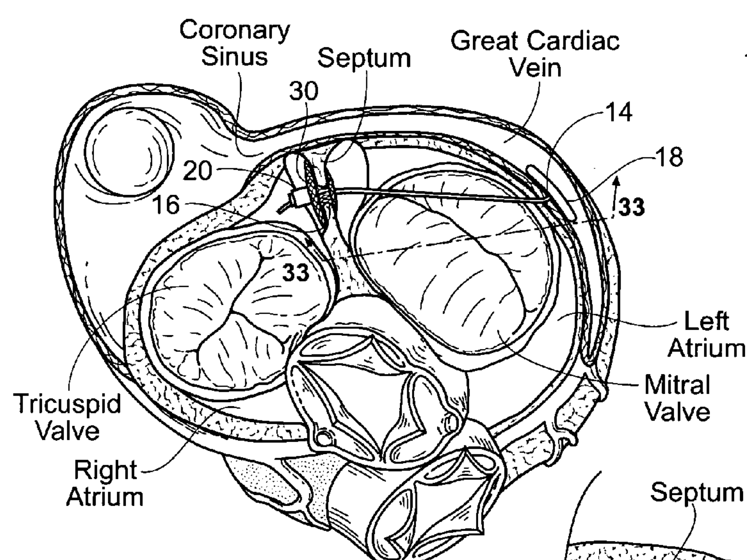
FIG. 32 is an anatomic superior view of a section of the human heart, showing the presence of an implant system of the type shown in FIGS. 10A and 10B.
Figure 33:
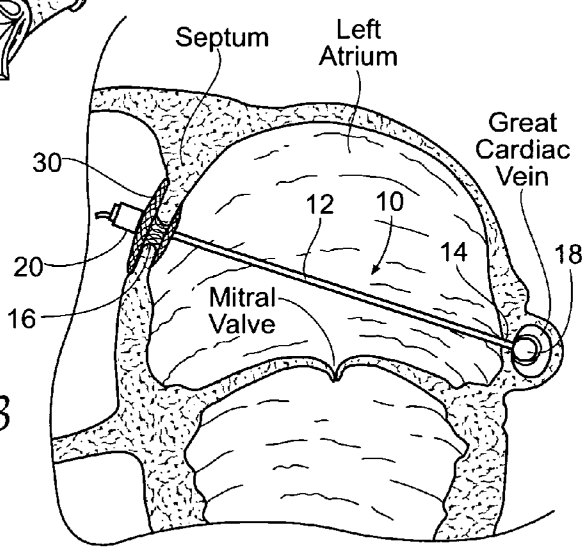
FIG. 33 is an anatomic section view of the implant system taken generally along line 33-33 in FIG. 32, showing the presence of an implant system of the type shown in FIGS. 10A and 10B, and showing proper coaptation of the mitral valve leaflets.

FIG. 31 shows an anatomical view of mitral valve dysfunction prior to the implantation of the implant 10. As can be seen, the two leaflets are not coapting, and as a result the undesirable back flow of blood from the left ventricle into the left atrium can occur. After the implant 10 has been implanted as just described, the implant 10 serves to shorten the minor axis of the annulus, thereby allowing the two leaflets to coapt and reducing the undesirable mitral regurgitation (see FIGS. 32 and 33). As can be seen, the implant 10 is positioned within the heart, including the bridging element 12 that spans the mitral valve annulus, the anterior bridge stop 20 and septal member 30 on or near the fossa ovalis, and the posterior bridge stop 18 within the great cardiac vein.

IV. Alternative Implantation Steps

The steps of implantation as previously described may be altered due to any number of reasons, such as age, health, and physical size of patient, and desired therapeutic effects. In one alternative embodiment, the posterior T-shaped bridge stop 120 (or alternative embodiments) is implanted via a GCV approach, instead of the left atrial approach as previously described. In an additional alternative embodiment, the coring procedure of the left atrial wall is replaced with a piercing procedure from the great cardiac vein to the left atrium.

A. GCV Approach

As previously described, penetration of the cutting catheter 80 into the great cardiac vein is confirmed under image guidance (see FIG. 26). Once penetration is confirmed, the LA guide wire 74 is advanced into the great cardiac vein and into the GCV catheter 40. The LA guide wire 74 is further advanced through the GCV catheter 40 until its end exits the body (preferably at the superior vena cava sheath). The LA catheter 60 and the GCV catheter 40 may now be removed. Both the LA guide wire 74 and the GCV guide wire 54 are now in position for the next step of establishing the trans-septal bridging element 12 (see FIG. 35A). At this point, an optional exchange catheter 28 may be advanced over the LA guide wire 74, starting at either end of the guide wire 74 and entering the body at either the femoral sheath or superior vena cava sheath, and advancing the exchange catheter 28 until it exits the body at the other end of the guide wire 74. The purpose of this exchange catheter is to facilitate passage of the LA guide wire 74 and bridging element 12, in a procedure to be described below, without cutting or injuring the vascular and heart tissues. In a preferred embodiment, the exchange catheter 28 is about 0.040 to 0.060 inch ID, about 0.070 to 0.090 inch OD, about 150 cm in length, has a lubricious ID surface, and has an atraumatic soft tip on at least one end so that it can be advanced through the vasculature without injuring tissues. It is to be appreciated that the ID, OD, and length may vary depending on the specific procedure to be performed.

In the GCV approach, the trans-septal bridging element 12 is implanted via a GCV to left atrium approach. A predetermined length, e.g., two meters, of bridging element 12 (having a leading end and a trailing end) is connected at the leading end to the tip of the LA guide wire 74 that had previously exited the body at the superior vena cava sheath and the femoral sheath. In this embodiment, the LA guide wire 74 serves as the loop guide wire, allowing the bridging element to be gently pulled or retracted into and through at least a portion of the vasculature structure and into a heart chamber. The vascular path of the bridging element may extend from the superior vena cava sheath through the coronary sinus into a region of the great cardiac vein adjacent the posterior mitral valve annulus, and from the great cardiac vein through atrial tissue into the left atrium, and from the left atrium into the right atrium through the interatrial septum, and from the right atrium to the femoral sheath.

Figure 34A:
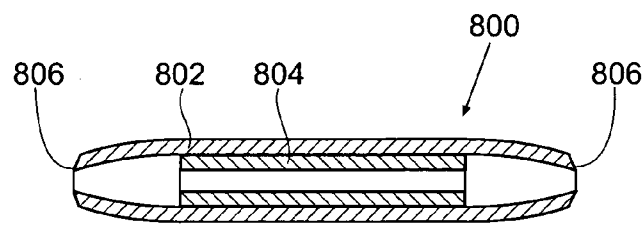
FIGS. 34A to 34D are sectional views of a crimp tube for connecting a guide wire to a bridging element, and showing the variations in the crimps used.
Figure 34B:
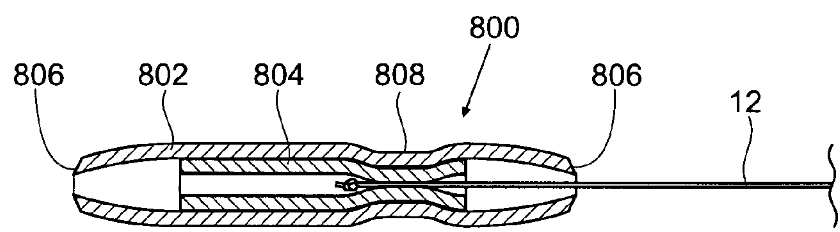
Figure 34C:
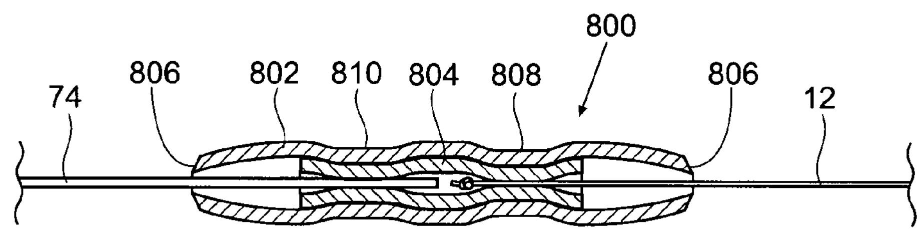
Figure 34D:
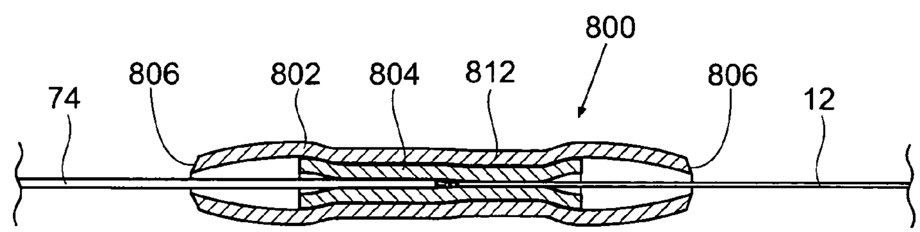

As can be seen in FIGS. 34A to 34D, a crimp tube or connector 800 may be used to connect the bridging element 12 to at least one end of the LA guide wire 74. FIG. 34A shows a crimp tube 800 preferably having an outer protective shell 802 and an inner tube 804. The outer protective shell 802 is preferably made of a polymeric material to provide atraumatic softness to the crimp tube, although other crimpable materials may be used. The inner tube 804 may be made of a ductile or malleable material such as a soft metal so as to allow a crimp to hold the bridging element 12 and guide wire 74 in place. The crimp tube ends 806 may be gently curved inward to aid in the movement of the crimp tube as the tube 800 moves through the vasculature. It is to be appreciated that the crimp tube may simply comprise a single tube made of a ductile or malleable material.

The bridging element 12 is positioned partially within the crimp tube 800. A force is applied with a pliers or similar crimping tool to create a first crimp 808 (see FIG. 34B). The end of the bridging element may include a knot, such as a single overhand knot, to aid in the retention of the bridging element 12 within the crimp tube. Next, the LA guide wire 74 is positioned partially within the crimp tube 800 opposite the bridging element 12. A force is again applied with a pliers or similar crimping tool to create a second crimp 810 (see FIG. 34C). Alternatively, both the bridging element 12 and the guide wire 74 may be placed within the crimp tube 800 at opposite ends and a single crimp 812 may be used to secure both the bridging element 12 and the guide wire 74 within the crimp tube (see FIG. 34D). It is to be appreciated that the crimp tube 800 may be attached to the bridging element 12 or guide wire prior to the implantation procedure so as to eliminate the step of crimping the bridging element 12 within the crimp tube 800 during the implantation procedure. The guide wire 74 is now ready to be gently retracted. It can also be appreciated that apparatus that uses adhesives or alternatively pre-attached mechanisms that snap together may also be used for connecting bridge elements to guide wires.

Figure 35B:
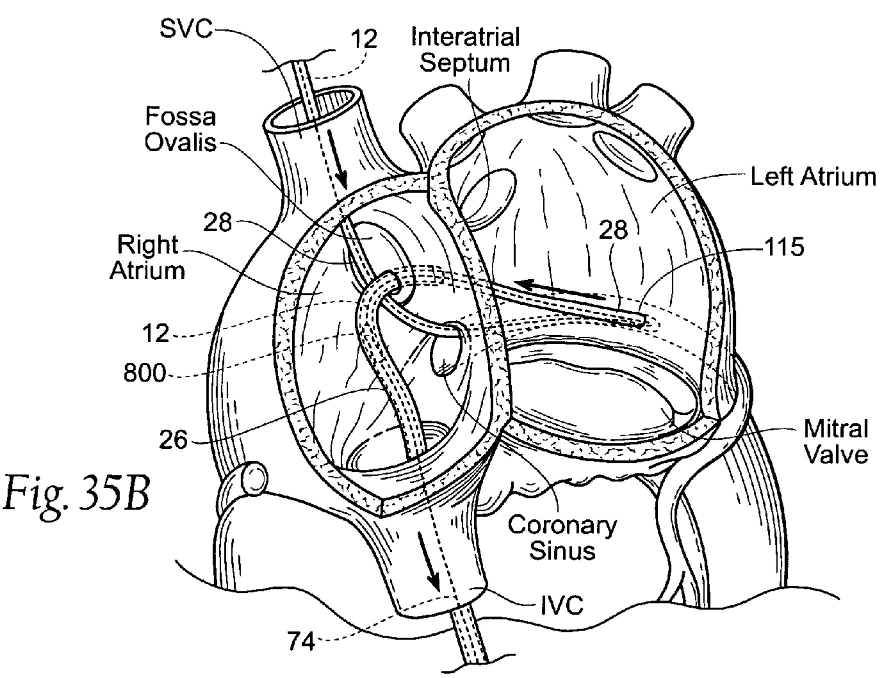
FIG. 35B is an anatomic view depicting a representative alternative catheter-based device for implanting an implant system of the type shown in FIGS. 10A to 10C, and showing a bridging element being pulled through the vasculature structure by a loop guide wire.

As can be seen in FIG. 35B, the LA guide wire 74 is gently retracted, causing the bridging element 12 to follow through the vasculature structure. If the optional exchange catheter 28 is used (as shown in FIGS. 35 A and 35B), the LA guide wire 74 retracts through the lumen of the exchange catheter 28 without injuring tissues. The LA guide wire 74 is completely removed from the body at the femoral vein sheath, leaving the bridging element 12 extending from exterior the body (preferably at the femoral sheath), through the vasculature structure, and again exiting at the superior vena cava sheath. The LA guide wire 74 may then be removed from the bridging element 12 by cutting or detaching the bridging element 12 at or near the crimp tube 800.

Figure 36B:
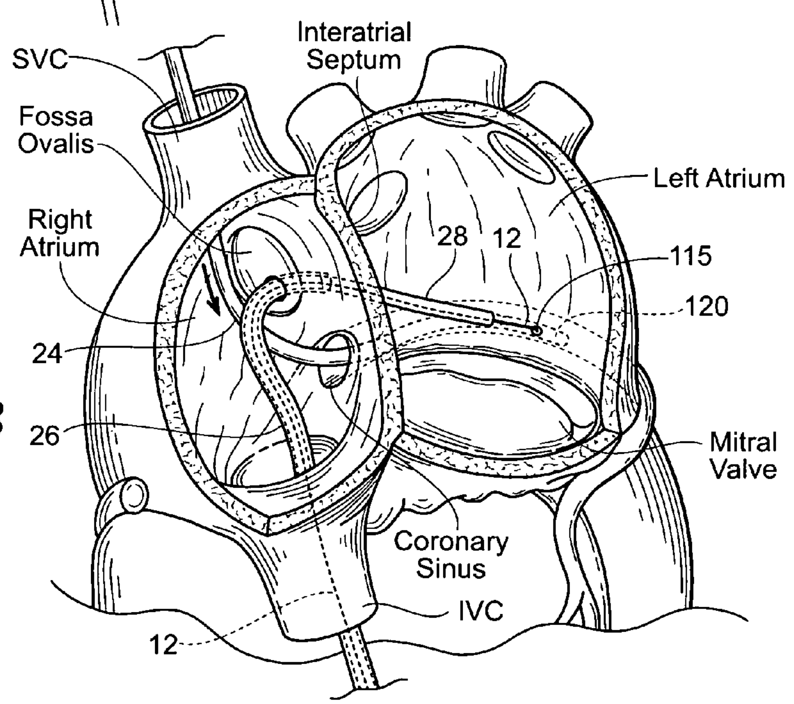
FIG. 36B is an anatomic view depicting a representative alternative catheter-based device for implanting a system of the type shown in FIGS. 10A to 10C, and showing a bridge stop being positioned within the great cardiac vein.

A posterior bridge stop, such as a T-shaped bridge stop 120 is preferably connected to the trailing end of bridging element 12 extending from the superior vena cava sheath. The T-shaped bridge stop 120 is then positioned onto or over the GCV guide wire 54. A deployment catheter 24 is then positioned onto or over the GCV guide wire 54 and is used to advance or push the T-shaped bridge stop 120 and bridging element 12 through the right atrium, through the coronary sinus, and into the great cardiac vein. If the optional exchange catheter 28 is used, the exchange catheter is gently retracted with the bridging element 12 or slightly ahead of it (see FIGS. 36A and 36B). Optionally, the bridging element 12 may be pulled from the femoral vein region, either individually, or in combination with the deployment catheter 24, to advance the T-shaped bridge stop 120 and bridging element 12 into position in the great cardiac vein. The GCV guide wire 54 is then retracted letting the T-shaped bridge stop 120 separate from the GCV guide wire 54 and deployment catheter 24. Preferably under image guidance, and once separation is confirmed, the bridging element 12 is gently pulled to position the T-shaped bridge stop 120 in abutment against the venous tissue within the great cardiac vein and centered over the GCV access lumen 115. The deployment catheter 24 and optional exchange catheter 28 may then be removed.

Figure 28:
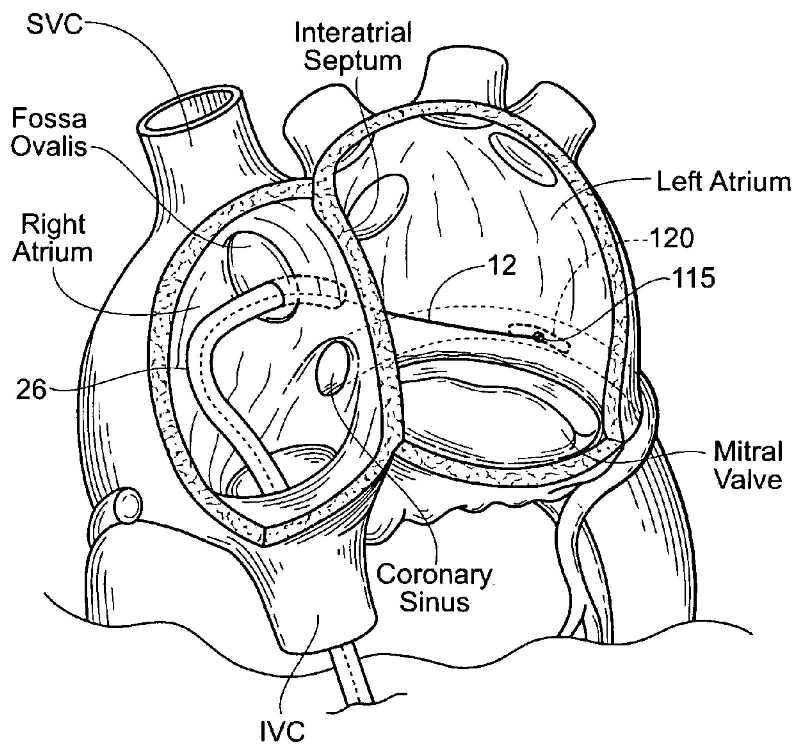
Figure 30:
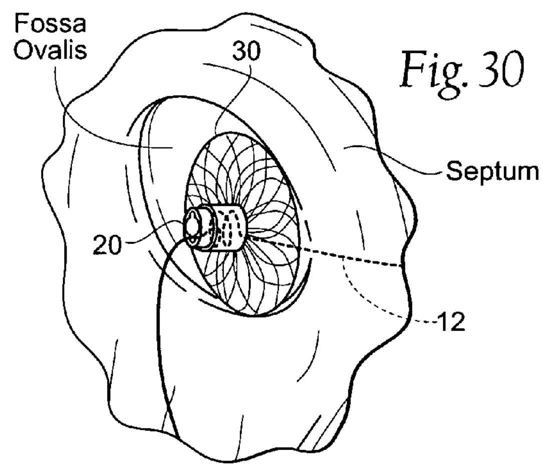

The T-shaped bridge stop 120 and the attached bridging element 12 remain within the great cardiac vein. The length of bridging element 12 extends from the posterior T-shaped bridge stop 120, through the left atrium, through the fossa ovalis, through the vasculature, and preferably remains accessible exterior the body. The bridging element 12 is now ready for the next step of establishing the anterior bridge stop region 16, as previously described, and as shown in FIGS. 28 to 30.

B. Piercing Procedure

In this alternative embodiment, the procedure to core a lumen from the left atrium into the great cardiac vein is replaced with a procedure where a sharp-tipped guide wire within the great cardiac vein is used to create a passage from the great cardiac vein into the left atrium. Alternative embodiments for the magnetic head of both the GCV catheter 40 and the LA catheter 60 are preferably used for this procedure.

Figure 45A:
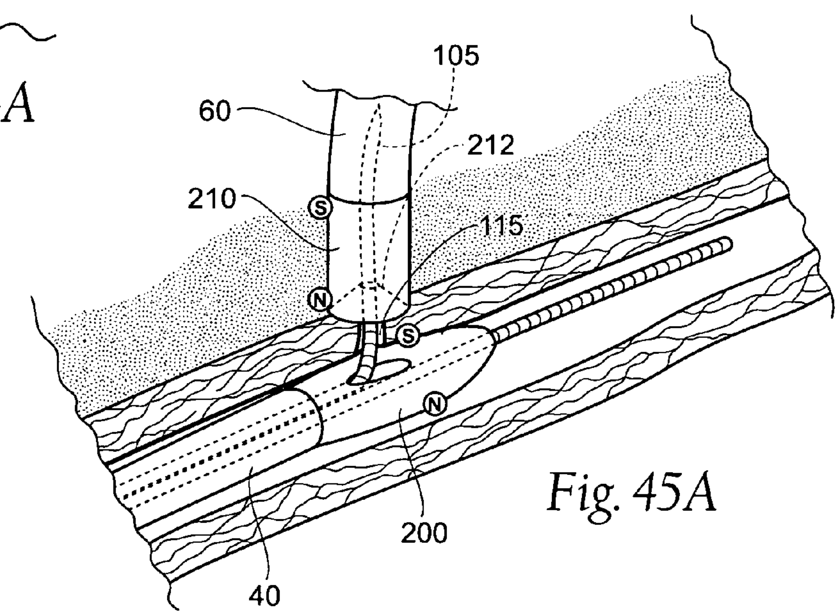
FIG. 45A is an anatomic partial perspective view of alternative magnetic catheter heads, with one catheter shown in the left atrium and one catheter shown in the great cardiac vein, and showing a side to end configuration.
Figure 45B:
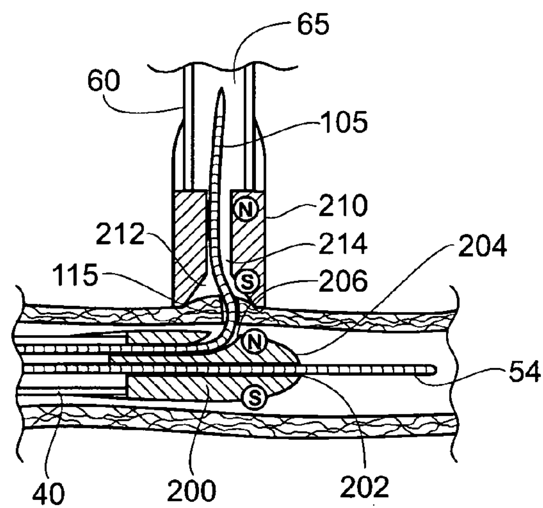
FIG. 45B is a partial sectional view of the alternative magnetic catheter heads of the type shown in FIG. 45A; showing a guide wire piercing the wall of the great cardiac vein and left atrium and extending into the receiving catheter.

FIGS. 45A and 45B show an end to side polarity embodiment for the GCV catheter magnetic head 200 and the LA catheter magnetic head 210. Alternatively, a side to side polarity may be used. The GCV catheter magnetic head 200 can maintain the same configuration for both the end to side polarity and the end to end polarity, while the LA catheter magnetic head 215 is shown essentially rotated ninety degrees for the side to side polarity embodiment (see FIG. 46).

Figure 45C:
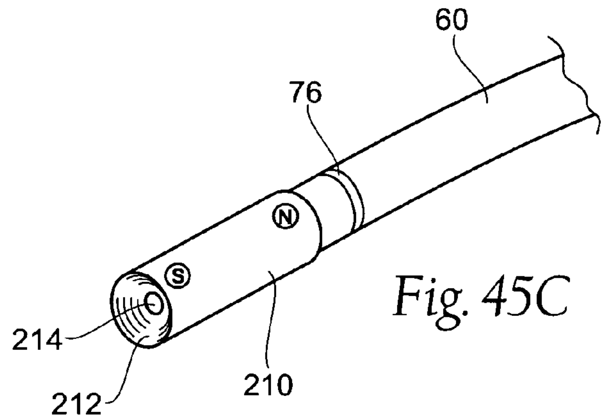
FIG. 45C is a partial perspective view of an alternative magnetic head of the type shown in FIG. 45B.

As seen in FIG. 45B, the GCV catheter magnetic head 200 includes a dual lumen configuration. A navigation guide wire lumen 202 allows the GCV guide wire 54 to extend through the cone or bullet shaped end 204 of the head 200 in order to steer the GCV catheter 40 into position. A second radially curved side hole lumen 206 allows the sharp tipped guide wire 105 (or tri-blade 100, for example) to extend through the head 200 and directs the sharp tipped guide wire 105 into the LA catheter magnetic head 210. The LA catheter magnetic head 210 includes a funneled end 212 and a guide wire lumen 214 (see FIG. 45C). The funneled end 212 directs the sharp tipped guide wire 105 into the lumen 214 and into the LA catheter shaft 65.

Figure 46:
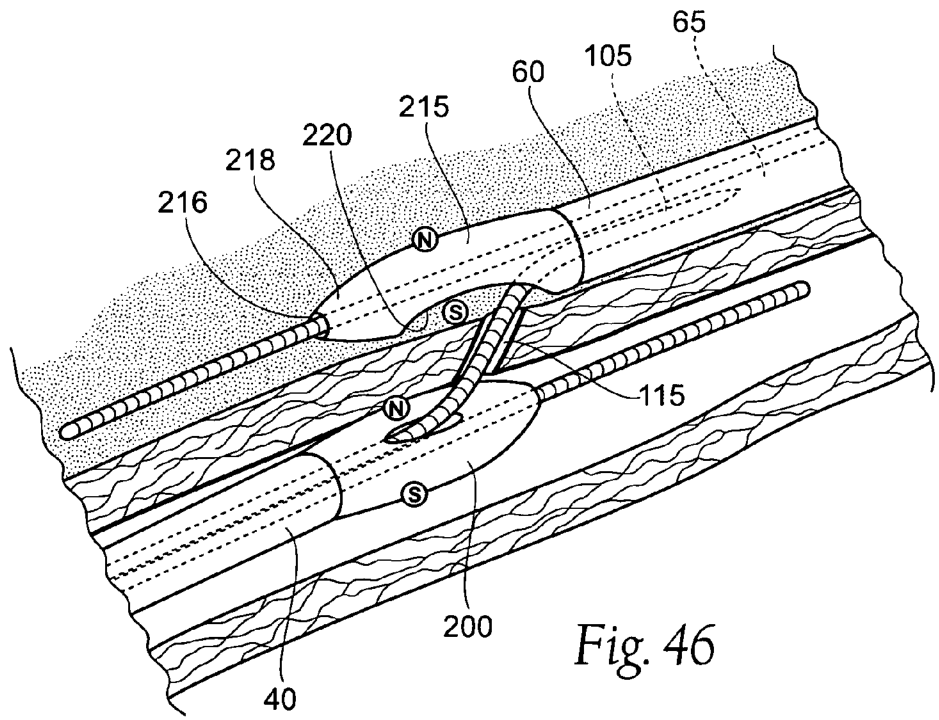
FIG. 46 is an anatomic partial perspective view of an additional alternative embodiment for the magnetic catheter heads of the type shown in FIG. 45A, showing a side to side configuration.

FIG. 46 shows the alternative embodiment of the LA catheter magnetic head 215 used with the side to side polarity embodiment. The head 215 may have the same configuration as the GCV catheter magnetic head 42 shown in FIGS. 39 and 40 and described in section III. The head 215 includes a navigation guide wire lumen 216 at the cone or bullet shaped end 218, and a side hole 220. The side hole 220 funnels the sharp tipped guide wire 105 (or tri-blade 100, for example), from the GCV catheter 40 to the LA catheter 60 and directs the guide wire 105 into the LA catheter shaft 65.

In use, both the GCV catheter 40 and the LA catheter 60 are advanced into the great cardiac vein and left atrium as previously described. The GCV catheter 40 and the LA catheter 60 each includes the alternative magnetically attractant head portions as just described. As best seen in FIGS. 45A and 45B, a sharp-tipped guide wire 105 is advanced through the GCV catheter 40 to the internal wall of the great cardiac vein. The sharp-tipped guide wire 105 is further advanced until it punctures or pierces the wall of the great cardiac vein and the left atrium, and enters the funneled end 212 within the LA catheter head 210. The sharp-tipped guide wire 105 is advanced further until it exits the proximal end of the LA catheter 60. Both the GCV catheter 40 and the LA catheter 60 may now be removed, leaving the GCV guide wire 54 and the sharp-tipped guide wire 105 in place. The posterior T-shaped bridge stop 120 is now implanted via the GCV approach, as previously described, and as shown in FIGS. 35A to 36B.

V. Alternative Bridge Stop Embodiments

Additional alternative embodiments of bridge stop devices may be used and are herein described. The bridge stop serves to secure the bridging element 12 at the posterior or anterior bridge stop region 14, 16, or both.

Figure 47A:
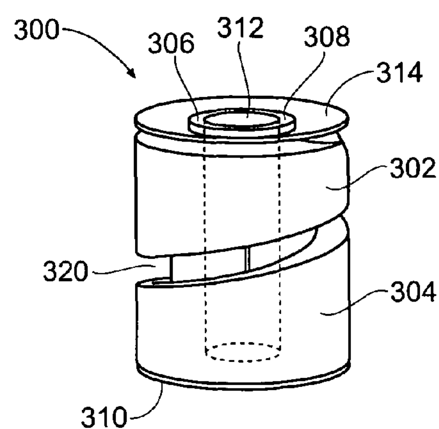
FIGS. 47A to 51 are perspective and sectional views of alternative embodiments of a bridge stop of the type shown in FIG. 44A.
Figure 47B:
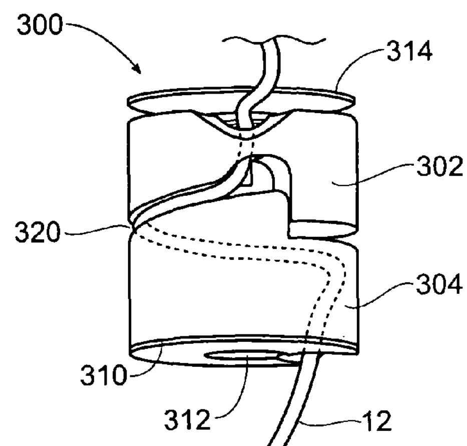

FIGS. 47A and 47B are perspective views of an alternative embodiment of a bridge stop 300 in accordance with the present invention. The bridge stop 300 preferably includes a fixed upper body 302 and a movable lower body 304. Alternatively, the upper body 302 may be movable and the lower body 304 may be fixed. The upper body 302 and lower body 304 are positioned circumjacent a tubular shaped rivet 306. The upper body 302 and lower body 304 are preferably held in position by the rivet head 308 and a base plate 310. The rivet 306 and base plate 310 includes a predetermined inner diameter 312, sized so as to allow the bridge stop 300 to be installed over a guide wire. A spring, such as a spring washer 314, or also known in the mechanical art as a Belleville Spring, is positioned circumjacent the rivet 306 and between the rivet head 308 and the upper body 302, and applies an upward force on the lower body 304. The lower body 304 is movable between a bridge unlocked position (see FIG. 47A), and a bridge locked position (see FIG. 47B). In the bridge unlocked position, the lower body 304 and the upper body 302 are not in contacting communication, creating a groove 320 between the upper body 302 and lower body 304. In the bridge locked position, the axial force of the spring washer 314 urges the lower body 304 into contacting, or near contacting communication with the upper body 302, whereby the bridging element 12, which has been positioned within the groove 320, is locked in place by the axial force of the lower body 304 being applied to the upper body 302.

In use, the bridging element 12 is positioned within the groove 320 while the lower body 304 is maintained in the bridge unlocked position 316. The bridge stop 300 is positioned against the septal member 30 and the bridging element 12 is adjusted to proper tension. The lower body 304 is then allowed to move toward the upper body 302, thereby fixing the position of the bridge stop 300 on the bridging element 12.

Figure 48A:
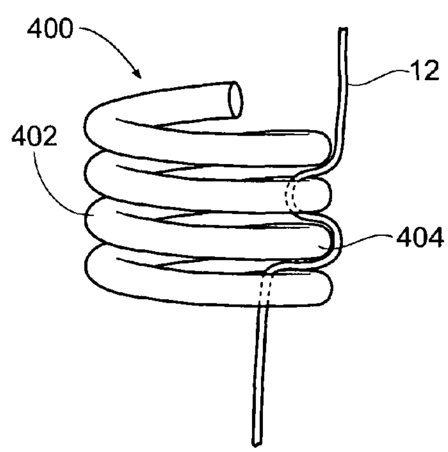
Figure 48B:
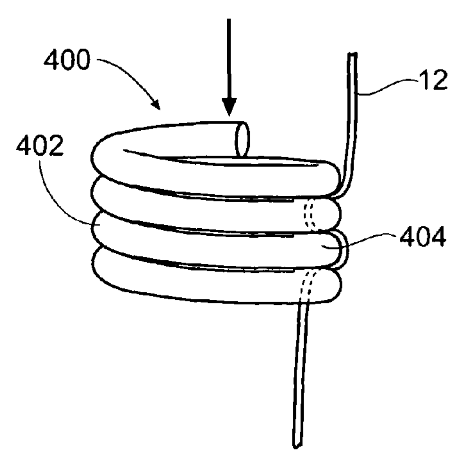

FIGS. 48A and 48B are perspective views of an alternative embodiment of the bridge stop 350 shown in FIGS. 47A and 47B. The bridge stop 400 preferably includes an extension or tension spring 402 wherein at least one revolution of the spring coils 404 is in a contacting relationship while the spring 402 is in a natural or no-load position. When in a tensioned state, the at least one revolution of the spring coils 404 is in a non-contacting relationship. In use, an axial tension force is applied to the spring 402, allowing the spring coils 404 to separate (see FIG. 48A). While in the tensioned state, the bridging element 12 is positioned between and/or around at least one, and preferably multiple spring coils 404. The bridge stop 400 is positioned against the septal member 30 and the bridging element 12 is adjusted to proper tension. The tension force is then removed from the spring 402 and the spring 404 is allowed to return to its no-load state (see FIG. 48B). In the spring's no-load state, the coils 404 provide a tight fit against the bridging element 12, thereby fixing the position of the bridge stop 400 on the bridging element 12.

Figure 49:
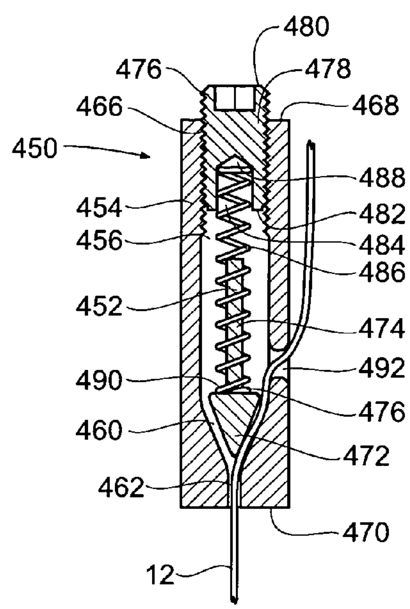

FIG. 49 is a cross sectional view of an alternative embodiment of a bridge stop 450 in accordance with the present invention. The bridge stop 450 preferably includes a plunger 452 within a tube 454. The tube 454 includes a plunger bore 456 extending partially through the length of the tube 454. The bore 456 then tapers inward at 460 creating a smaller bore 462. An internally threaded portion 466 of plunger bore 456 extends from the first side 468 of the tube 454 to approximately midway between the first side 468 and the second side 470 of tube 454. Alternatively, the threaded portion 466 may be external on the tube 454. The plunger 452 is positioned within the plunger bore 456. The plunger 452 has a conical shaped head 472 and a shaft 474 extending from the base 476 of the conical shaped head 472. A torque screw 478, having a first side 480 and a second side 482, is threaded into bore 456. The first side 480 includes receiver means for a driver tool to rotate the torque screw 478, such as, but not limited to phillips, slotted, six lobe, or square. The second side 482 includes a pocket 484. A compression spring 486 having a first end 488 is positioned within the pocket 484, and a second end 490 of the compression spring 486 is positioned over the shaft 474 of the plunger 452.

An aperture 492 is disposed within the wall of the shaft 474 at a point above where the plunger bore 456 begins to taper inward. Bridging element 12 is shown disposed through the small bore 462 and through aperture 492.

In use, the torque screw 478 may be backed off to allow the plunger head 472 to move away from the tapered portion 460 of the plunger bore 456. Bridging element 12 is disposed within bore 462 and extends out of the tube 454 at aperture 492. The bridge stop 450 is then positioned against the septal member 30 and the bridging element 12 is adjusted to proper tension. The torque screw 478 is then torqued into the bore 456, causing the plunger head 472 to provide a tight fit against the bridging element 12, thereby fixing the position of the bridge stop 450 on the bridging element 12.

Figure 50:
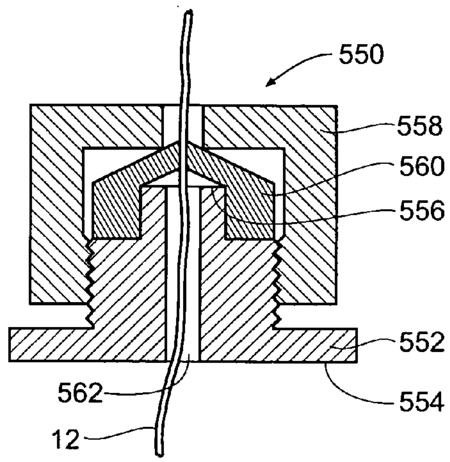

FIG. 50 is a cross sectional view of an additional alternative embodiment of a bridge stop 550, in accordance with the present invention. The bridge stop 550 preferably includes a base portion 552 having a first side 554 and a second side 556, a cap 558 threaded over the base portion 552, and a collet 560 positioned between the second side 556 of the base 552 and the cap 558. The collet 560 is seated on the second side 556 of the base 552. A bore 562 extends axially through the base 552, collet 560, and cap 558. In use, the cap 558 may be backed off to allow the bore 562 within the collet 560 to expand sufficiently to allow the bridging element 12 to slide freely through the bridge stop 550. The bridge stop 550 is then positioned against the septal member 30 and the bridging element 12 is adjusted to proper tension. The cap 558 is then tightened onto the base 552, which causes the bore 562 within the collet 560 to close down. The collet 560 provides a tight fit against the bridging element 12, thereby fixing the position of the bridge stop 550 on the bridging element 12. Collet 560 can be made of an elastomer or deformable type of material to make the pinching force more distributed and less traumatic to the bridging element 12.

Figure 51:
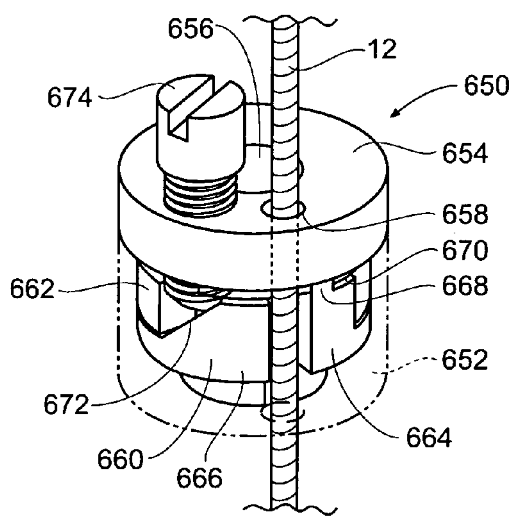

FIG. 51 is a perspective view of an additional alternative embodiment of a bridge stop 650 in accordance with the present invention. The bridge stop 650 comprises a housing 652 having a lid 654. The bridge stop 650 may be tubular in shape, and may include an axially positioned lumen 656 extending therethrough; the lumen 656 being sized to allow the bridge stop 650 to be positioned over a guide wire for implantation and optionally secured to hub 31 of the septal member 30. A second radially offset axial lumen 658 also extends through the bridge stop 650. The second lumen 658 allows for passage of the bridging element 12 through the bridge stop 650.

Positioned within the housing 652 is a spring band 660 and a spacer 662. The spring band 660 is generally circular in shape and has a fixed end 664 and a free end 666. The fixed end 664 includes a tab 668 positioned within a slot 670 in the lid 654 to prevent movement of the fixed end. The free end 666 includes an inclined angle 672 which allows for circumferential displacement when the inclined angle 672 is depressed. The spacer 662 is positioned adjacent the spring band 660, and keeps the spring band in alignment and free of buckling. As seen in FIG. 51, a screw 674 may be positioned in the lid 654, and when turned into the bridge stop 650, the screw 674 provides a force on the inclined angle 672. The free end 666 of the spring band 660 is caused to rotate toward the fixed end 664, thereby pinching the bridging element 12 within the bridge stop 650 (between the fixed end 664 and the free end 666), and fixing the position of the bridge stop 650 on the bridging element 12.

It is to be appreciated that each embodiment of the bridge stop may be configured to have a bridge securing configuration in its static state, so as to require a positive actuation force necessary to allow the bridging element to move freely within or around the bridge stop. When a desirable tension in the bridge element is achieved, the actuation force is removed, thereby returning the bridge stop back to its static state and securing the bridge stop to the bridging element. Alternatively, the bridge stop may be configured to allow free movement of the bridging element 12 in its static state, thereby requiring a positive securing force to be maintained on the bridge stop necessary to secure the bridging element within the bridge stop.

Preferably, the bridge securing feature is unambiguous via tactile or fluoroscopic feedback. The securing function preferably may be locked and unlocked several times, thereby allowing the bridging element to be readjusted. The bridge stop material is also desirably radio-opaque or incorporates radio-opaque features to enable the bridge stop to be located with fluoroscopy.

VI. Alternative T-Shaped Bridge Stop Embodiments

Additional alternative embodiments of T-shaped bridge stop devices may be used and are herein described. The T-shaped bridge stop may serve to secure the bridging element 12 at the anterior bridge stop region 16, or the posterior bridge stop region 14, or both. It is to be appreciated that the alternative embodiments of the T-shaped bridge stop devices may be symmetrical as shown, or may also be asymmetrically shaped.

Figure 52A:
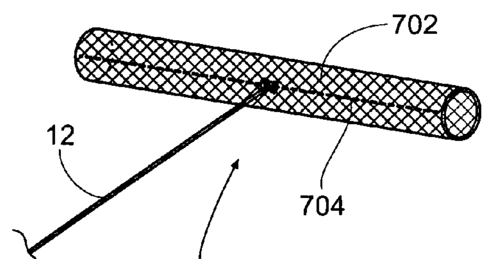
FIG. 52A is a perspective view of an alternative embodiment of a T-shaped bridge stop or member of the type shown in FIG. 43A, showing a balloon expandable or self-expanding stent with a reinforcing strut.

FIG. 52A is a perspective view of an alternative embodiment of a T-shaped bridge stop 700 in accordance with the present invention. The T-shaped bridge stop 700 preferably includes an intravascular stent 702 and, optionally, a reinforcing strut 704. The stent 702 may be a balloon expandable or self expanding stent. As previously described, the T-shaped bridge stop 700 is preferably connected to a predetermined length of the bridging element 12. The bridging element 12 may be held within, on, or around the T-shaped bridge stop 700 through the use of any of the bridge locks as previously described, or may be connected to the T-shaped bridge stop 700 by way of tying, welding, or gluing, for example, or any combination.

Figure 52B:
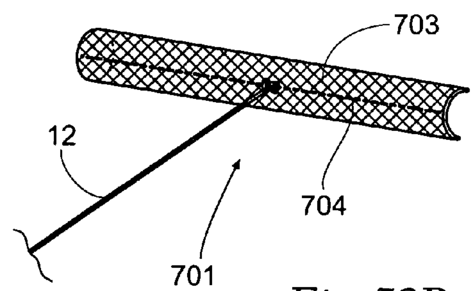
FIG. 52B is a perspective view of an alternative embodiment of a T-shaped bridge stop or member of the type shown in FIG. 52A, showing the expandable or self-expanding stent in a lattice or half stent configuration.

FIG. 52B is a perspective view of an alternative embodiment of the T-shaped bridge stop 700 in accordance with the present invention. The alternative T-shaped bridge stop 701 preferably includes a lattice or half round intravascular stent 703 and, optionally, a reinforcing strut 704. The "C" shaped stent 703 may be a balloon expandable stent or self expanding stent. As previously described, the T-shaped bridge stop 701 is preferably connected to a predetermined length of the bridging element 12. The bridging element 12 may be held within, on, or around the T-shaped bridge stop 701 through the use of any of the bridge locks as previously described, or may be connected to the T-shaped bridge stop 701 by way of tying, welding, or gluing, for example, or any combination.

Figure 53A:
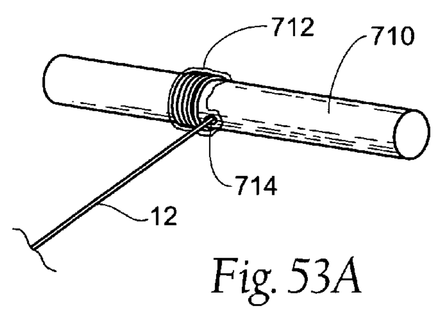
FIGS. 53A to 53F are perspective views showing alternative methods of connecting a bridging element to a bridge stop or T-shaped member.

FIGS. 53A to 53E show alternative methods of connecting the bridging element 12 to a T-shaped bridge stop 710. FIG. 53A shows a T-shaped member 710 where the bridging element 12 is wound around the T-shaped member 710. The bridging element 12 may be secured by adhesive 712, knot, or a securing band placed over the bridging element 12, for example. Alternatively, the bridging element 12 may first be threaded through a lumen 714 extending through the T-shaped member 710 perpendicular the length of the T-shaped member. The bridging element 12 may then be wound around the T-shaped member, and secured by adhesive 712, securing band, or knot, for example.

Figure 53B:
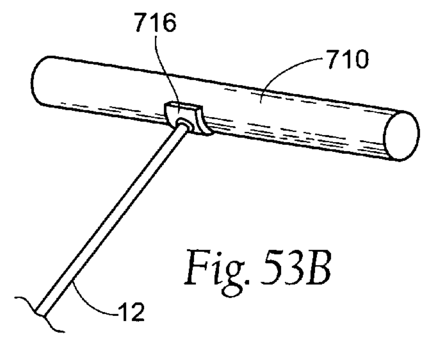

FIG. 53B shows a T-shaped member 710 where the bridging element 12 is welded or forged to a plate 716. The plate 716 may then be embedded within the T-shaped member 710, or alternatively, secured to the T-shaped member 710 by gluing or welding, for example.

Figure 53C:
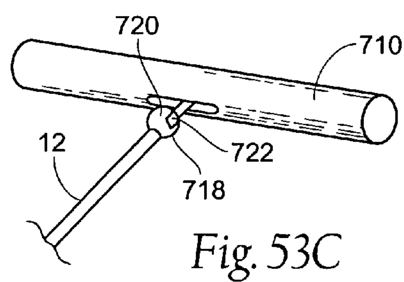
Figure 53D:
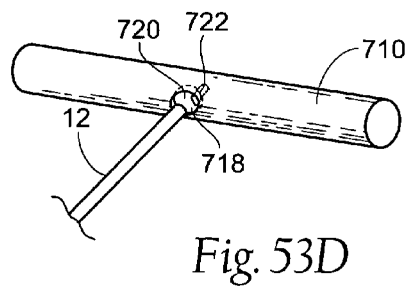

FIGS. 53C and 53D show alternative embodiments where a ball and socket joint 718 connects the bridging element 12 to the T-shaped member 710. In FIG. 53C, the ball and socket joint 718 is located external to the T-shaped member 710. Alternatively, the ball and socket joint 718 may be positioned partially or completely within the T-shaped member 710, as seen in FIG. 53D. The bridging element 12 is secured to the socket 720, and the ball 722 is secured to the T-shaped member 710. The ball and socket joint 718 allows for free rotation of the bridging element 12 relative to the T-shaped member 710 or vice versa. The ball and socket joint 718 is preferably made of a micro-machined stainless steel, although other implantable materials may be used as well.

Figure 53E:
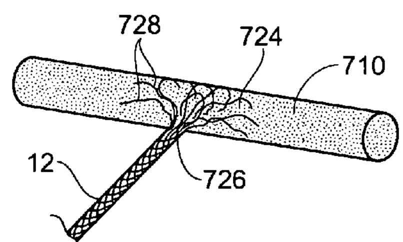

FIG. 53E shows an additional alternative embodiment of the T-shaped member 710 where the bridging element 12 is embedded in a polymeric substrate 724 of the T-shaped member 710. In this embodiment, the bridging element 12 preferably is a braided stainless steel micro-cable. The end 726 of the bridging element 12 is separated into an assortment of strands 728, which are then embedded in the polymeric substrate 724.

Figure 53F:
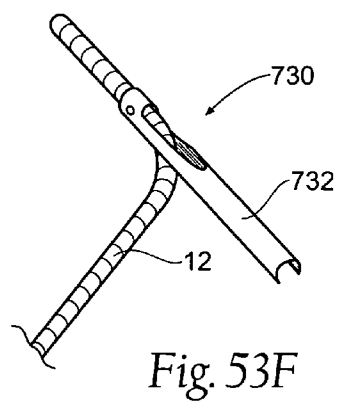

FIG. 53F shows a guide wire or bridging element style hinged T-shaped bridge stop embodiment 730 having a hinged leg 732. When in the expanded state, as shown in FIG. 53F, the hinged leg 732 forms one arm of a "T." The hinged leg 732 has a "C" shaped or concave profile, allowing the hinged leg 732 to lie over the guide wire or bridging element 12 while tracking to its final location. When the guide wire or bridging element 12 is gently retracted, the hinged leg 732 pivots away from the bridging element 12 forming the T-shaped bridge stop.

VII. Alternative Anterior Bridge Stop Embodiments

In place of, or in combination with the septal member 30 previously described, alternative embodiments of an anterior bridge stop may be used.

Figure 54:
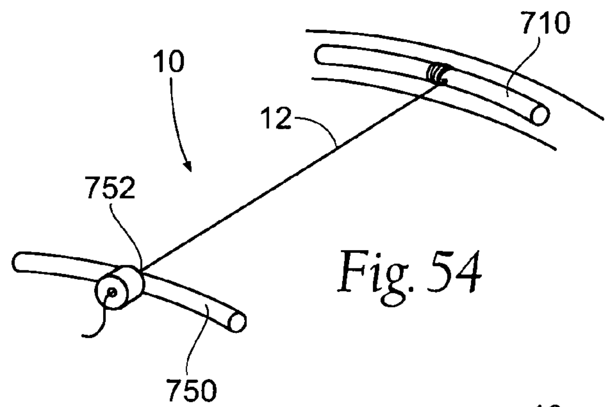

FIG. 54 shows an implant 10 having a T-shaped bridge stop 710 in the great cardiac vein and an anterior T-shaped bridge stop 750. The anterior T-shaped bridge stop 750 may be of a construction of any of the T-shaped bridge stop embodiments described. The T-shaped member 750 includes a lumen 752 extending through the T-shaped member 750 perpendicular to the length of the T-shaped member. The bridging element 12 may be secured by a free floating bridge stop as previously described.

Figure 55:
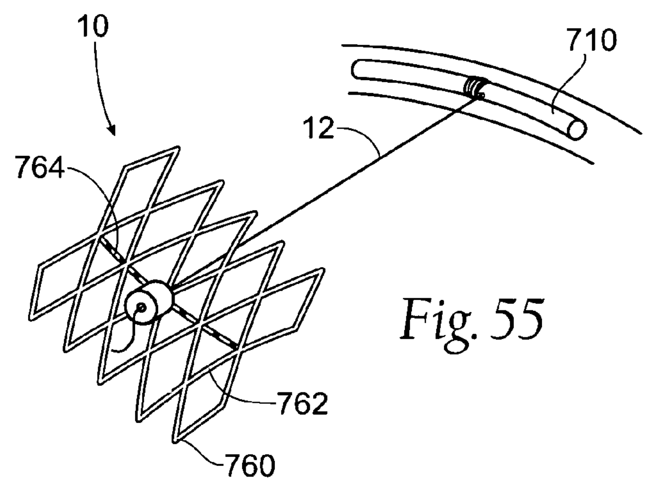

FIG. 55 shows an implant 10 having a T-shaped bridge stop 710 in the great cardiac vein and an anterior lattice style bridge stop 760. The lattice 762 is positioned on the septal wall at or near the fossa ovalis. Optionally, the lattice 762 may include a reinforcement strut 764 to distribute the bridging element 12 tension forces over a greater area on the septal wall. The anterior lattice style bridge stop 760 may be packed in a deployment catheter with the bridging element 12 passing through its center. The lattice 762 is preferably self expanding and may be deployed by a plunger. The bridging element 12 may be secured by a free floating bridge stop as previously described.

Figure 56A:
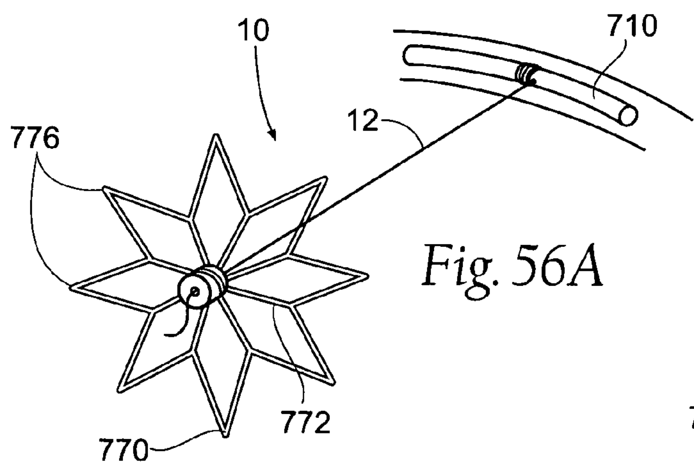
Figure 56B:
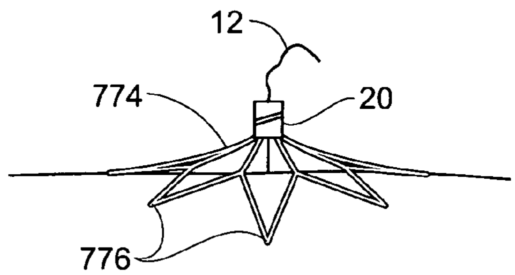
FIG. 56B is a side view of an alternative bridge stop of the type shown in FIG. 56A.

FIG. 56A shows an implant 10 having a T-shaped bridge stop 710 in the great cardiac vein and an anterior star shaped bridge stop 770. The star 772 is positioned on the septal wall at or near the fossa ovalis. The star shaped bridge stop 770 may be packed in a deployment catheter with the bridging element 12 passing through its center. The star 772 is preferably self expanding and may be deployed by a plunger. When the star shaped bridge stop 770 is deployed, the center portion 774 stands proud of the septal wall to concentrate forces to the star points 776 (see FIG. 56B). The bridging element 12 may be secured by a free floating bridge stop as previously described.

Figure 57:
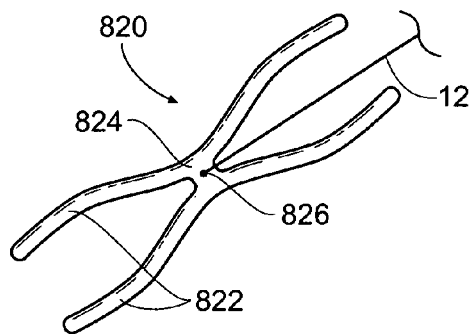
FIGS. 57 to 59 are perspective views of additional alternative bridge locks.

FIG. 57 shows an additional embodiment of an anterior bridge stop 820. The bridge stop 820 includes at least two arms 822 extending radially from a generally central portion 824, and preferably includes more than two arms, as shown in FIG. 57. The bridge stop 820 is positioned on the septal wall at or near the fossa ovalis. The bridge stop 820 may be packed in a deployment catheter with the bridging element 12 passing through its center lumen 826. The bridge stop is preferably self expanding and may be deployed by a plunger after being folded into a catheter. The bridging element 12 may be secured by a free floating bridge stop as previously described or fixed in position.

Figure 58:
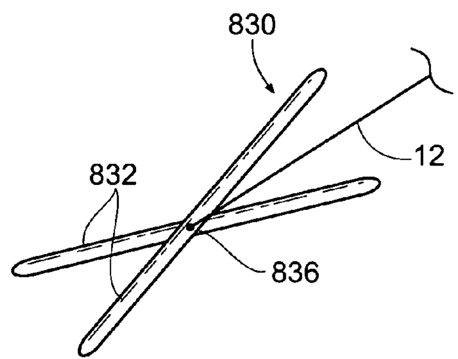

FIG. 58 shows an additional embodiment of an anterior bridge stop 830. The bridge stop 830 again includes at least two arms 832, and preferably includes more than two. In this embodiment, each arm 832 is an independent member, and is free to move relative to the remaining arms. The bridge stop 830 is positioned on the septal wall at or near the fossa ovalis. The bridge stop 830 may be packed in a deployment catheter with the bridging element 12 passing through a lumen 836 in each arm; the lumen being located generally central along the longitudinal axis of each arm. The bridge stop is preferably self expanding and may be deployed by a plunger. The bridging element 12 may be secured by a free floating bridge stop as previously described or fixed in position.

Figure 59:
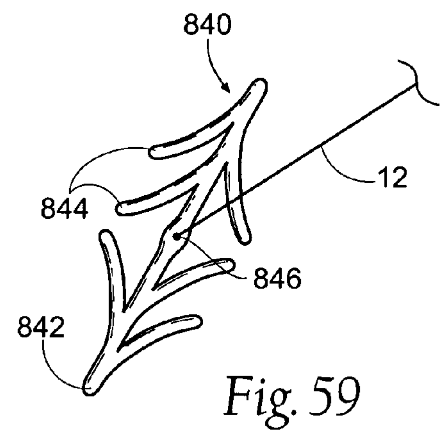

FIG. 59 shows an additional embodiment of an anterior bridge stop 840. The bridge stop 840 includes at least one main trunk 842, and at least one arm 844 extending radially from the trunk 842, and preferably more than one arm, as shown in FIG. 59. The bridge stop 840 is positioned on the septal wall at or near the fossa ovalis. The bridge stop 840 may be packed in a deployment catheter with the bridging element 12 passing through a lumen 846; the lumen being located generally central along the longitudinal axis of the trunk 842. The bridge stop is preferably self expanding and may be deployed by a plunger. The bridging element 12 may be secured by a free floating bridge stop as previously described or fixed in position.

Figure 60A:
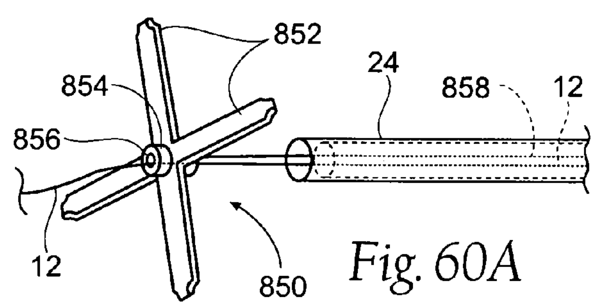
FIG. 60A is a perspective view of an alternative bridge stop and showing the deployment catheter and deployment wire.
Figure 60B:
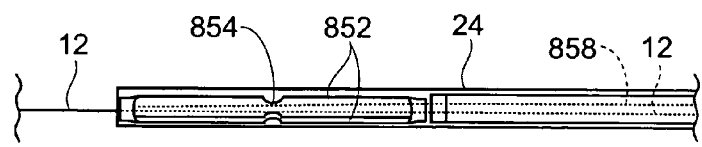
FIG. 60B is a side view of the alternative bridge stop of the type shown in FIG. 60A, showing the bridge stop in the deployment catheter prior to being deployed.

FIG. 60A shows an additional embodiment of an anterior bridge stop 850. The bridge stop 850 includes at least one arm 852 extending radially from a generally central portion 854, and preferably includes more than one arm, as shown in FIG. 60A. The bridge stop 850 is positioned on the septal wall at or near the fossa ovalis. The bridge stop 850 may be packed in a deployment catheter 24 with the bridging element 12 passing through its center lumen 856 (see FIG. 60B). The bridge stop 850 may be self expanding and may be deployed by a plunger, or alternatively may be deployed by applying tension, on a deployment wire 858 and pushing on the plunger to expand the at least one arm 852. The forces of the deployment wire 858 and plunger cause the bridge stop 850 to be plastically deformed into its final shape. The bridging element 12 may be secured by a free floating bridge stop as previously described or fixed in position.

FIGS. 61A to 62B show additional embodiments of an anterior bridge stop incorporating the use of porcine or equine pericardium to spread the tension forces of the bridging element 12, and also to provide a padding surface to the septal wall and to promote the bridge stop's ingrowth within the septal wall tissue.

Figure 61A:
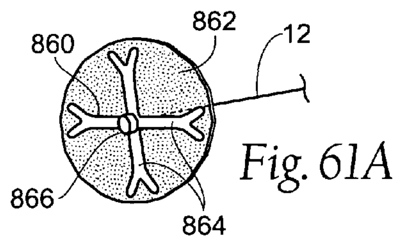
FIG. 61A is a perspective view of an alternative bridge stop including a single layer of pericardium.
Figure 61B:
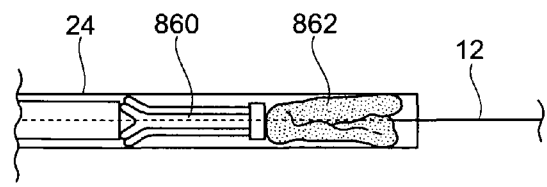
FIG. 61B is a side view of the alternative bridge stop of the type shown in FIG. 61A, showing the bridge stop in the deployment catheter prior to being deployed.

As can be seen in FIG. 61A, a pad 862 of pericardium is positioned on the septal wall side of a bridge stop 860. The bridge stop 860 as shown includes a plurality of arms 864 extending radially from a generally central portion 866. The bridge stop 860, including the pericardium pad 862, is positioned on the septal wall at or near the fossa ovalis, with the pericardium pad 862 positioned between the septal wall and the bridge stop 860. The bridge stop 860 and pericardium pad 862 may be packed in a deployment catheter 24 with the bridging element 12 passing through both the bridge stop 860 and the pericardium pad 862 (see FIG. 61B). The bridge stop 860, including the pericardium pad 862, is preferably self expanding and may be deployed by a plunger. The bridging element 12 may be secured by a free floating bridge stop as previously described or fixed in position.

Figure 62A:
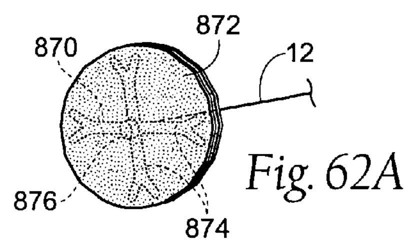
FIG. 62A is a perspective view of an alternative bridge stop including multiple layers of pericardium.
Figure 62B:
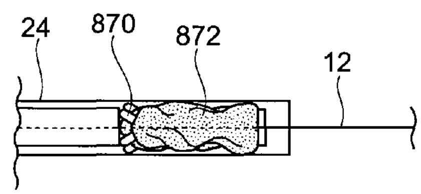
FIG. 62B is a side view of the alternative bridge stop of the type shown in FIG. 62A, showing the bridge stop in the deployment catheter prior to being deployed.

FIG. 62A shows an alternative embodiment of the bridge stop 860. FIG. 62A, shows a bridge stop 870 positioned between at least two layers of pericardium 872. Pericardium 872 may be a single piece of pericardium having a butterfly cut to allow the bridge stop 870 to be positioned between the two layers, or the pericardium may include at least two separate pads, so as to allow the bridge stop 870 to be positioned between the at least two pads. The bridge stop 870 as shown includes a plurality of arms 874 extending radially from a generally central portion 876. The bridge stop 870, including the pericardium pad 872, is positioned on the septal wall at or near the fossa ovalis, with one layer of the pericardium pad 872 being positioned between the septal wall and the bridge stop 870, and the other layer of pericardium 872 exposed to the right atrium. The bridge stop 870 and pericardium pad 872 may be packed in a deployment catheter 24 with the bridging element 12 passing through both the bridge stop 870 and the pericardium pad 872 (see FIG. 62B). The bridge stop 870, including the pericardium pad 872, is preferably self expanding and may be deployed by a plunger. The bridging element 12 may be secured by a free floating bridge stop as previously described or fixed in position.

Both bridge stop embodiments 860 and 870 may include any of the self-expanding embodiments described herein, and as shown are non-limiting embodiments for incorporation with a pericardium pad or pads. It should also be appreciated that pads 862 and 872 may be composed of biological tissue other than pericardium and further may be lined with polyester fabric or equivalent to promote tissue in-growth.

Figure 63A:
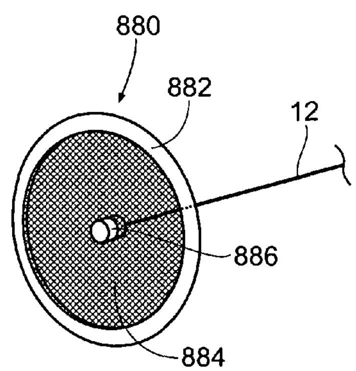
FIG. 63A is a perspective view of an alternative bridge stop including a balloon structure.
Figure 63B:
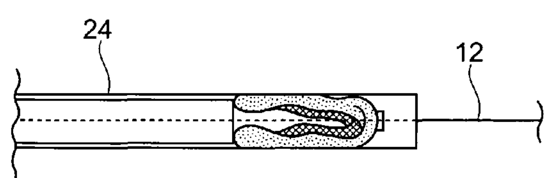
FIG. 63B is a side view of the alternative bridge stop of the type shown in FIG. 63A, showing the bridge stop in the deployment catheter prior to being deployed.
Figure 63C:
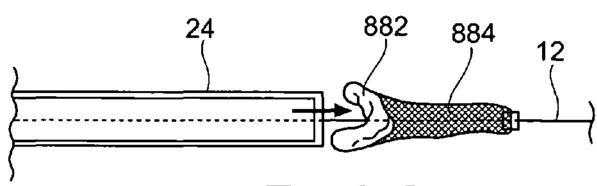
FIG. 63C is a side view of the alternative bridge stop of the type shown in FIG. 63A, showing the bridge stop just after exiting the deployment catheter and prior to being deployed.

FIGS. 63A to 63C show an additional embodiment of an inflatable anterior bridge stop 880. The bridge stop 880 includes a balloon portion 882 and a central portion 884. The balloon portion 882 may take on any number of shapes, and is shown as a loop or ring. The central portion 884 may comprise a fabric or other implantable material to allow for tissue ingrowth. The balloon 882 may be inflated with a glue material in a liquid state, such as an epoxy glue, or other materials that will harden allowing the balloon to maintain its expanded configuration. The resulting pressure from the inflation process encourages the balloon portion 882 and the central portion 884 to expand to its deployed configuration. When the balloon inflation material has hardened, the hoop or ring shaped balloon spreads the tension force from the bridging element 12 and keeps the central fabric portion open and flat. The bridge stop 880 is positioned on the septal wall at or near the fossa ovalis. The bridge stop 880 may be packed in a deployment catheter 24 with the bridging element 12 passing through a lumen 886 in the central portion 884 (see FIG. 63B). The bridge stop is preferably self expanding and may be deployed by a plunger. FIG. 63C shows the bridge stop 880 just after exiting the deployment catheter 24 and prior to inflation of the balloon portion 882. The bridging element 12 may be secured by a free floating bridge stop as previously described or fixed in position.

VIII. Fixed Length Bridging Element for Predetermined Tension Across a Heart Valve Annulus or for Predetermined Reduction in Septal-Lateral Length In order to achieve desired septal-lateral mitral valve dimension, the proper bridge length between the fossa ovalis and the GCV must be selected.

The septal-lateral mitral valve annulus length and the fossa ovalis to GCV length may be readily assessed using three dimensional echocardiography or magnetic resonance imaging, for example, either prior to or during the implantation procedure in order to properly size the fixed length bridging element prior to implantation.

Figure 64:
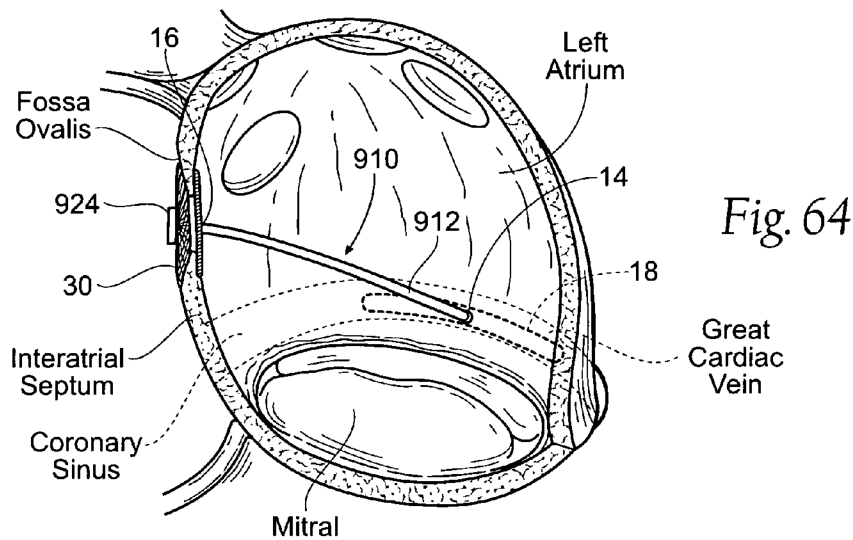
FIG. 64 is an anatomic anterior perspective view of the left atrium and a portion of the right atrium, with portions broken away and in section to show the presence of an alternative implant system of the type shown in FIGS. 10A to 10C, the alternative implant system includes a fixed length inter-atrial bridging element that spans the mitral valve annulus, with a posterior bridge stop positioned in the great cardiac vein and an anterior bridge stop positioned on the inter-atrial septum, the inter-atrial bridging element extending in an essentially straight path generally from a mid-region of the annulus to the inter-atrial septum.
Figure 65:
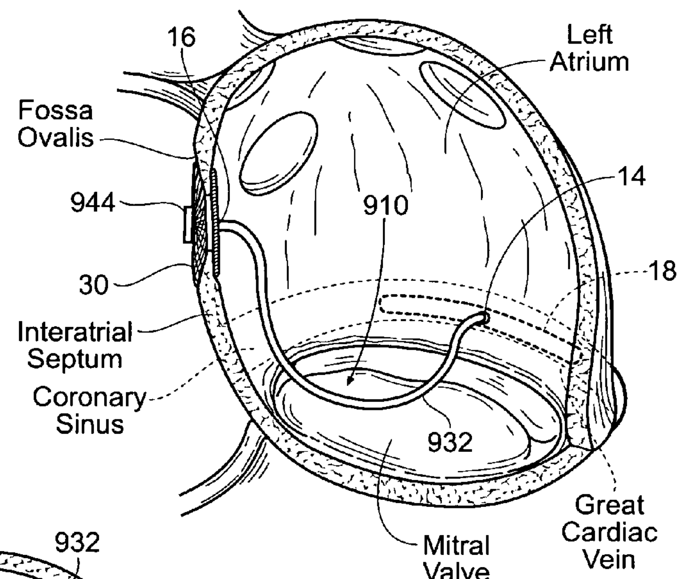
FIG. 65 is an anatomic anterior perspective view of the left atrium, and a portion of the right atrium, with portions broken away and in section to show the presence of an alternative implant system of the type shown in FIG. 64, the alternative implant system includes a fixed length inter-atrial bridging element that spans the mitral valve annulus, with a posterior region situated in the great cardiac vein and an anterior region situated on the interatrial septum, the fixed length inter-atrial bridging element extending in a curvilinear path, bending around a trigone of the annulus generally from a mid-region region of the annulus, as well as dipping downward toward the plane of the valve.
Figure 66:
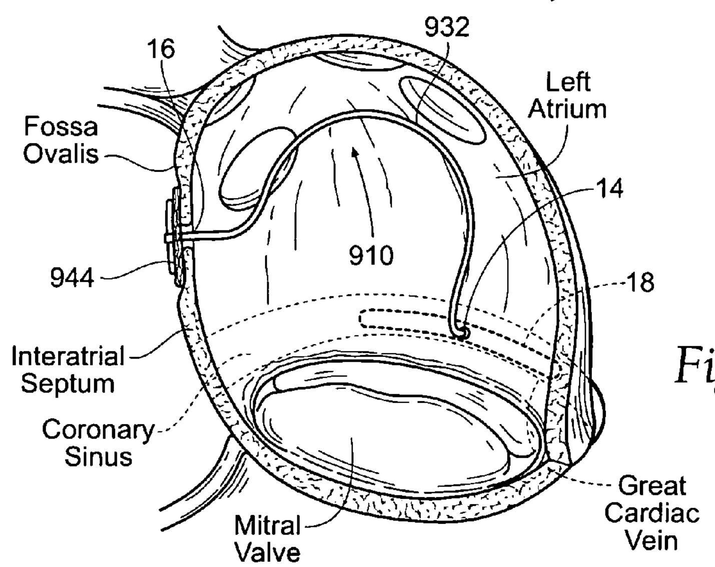
FIG. 66 is an anatomic anterior perspective view of the left atrium, and a portion of the right atrium, with portions broken away and in section to show the presence of an alternative implant system of the type shown in FIG. 64, the alternative implant system includes a fixed length inter-atrial bridging element that spans the mitral valve annulus, with a posterior region situated in the great cardiac vein and an anterior region situated on the interatrial septum, the fixed length inter-atrial bridging element extending in a curvilinear path, bending around a trigone of the annulus generally from a mid-region region of the annulus, as well as elevating in an arch toward the dome of the left atrium.

FIGS. 64 to 66 show embodiments of an implant system 910 having a fixed length bridging element. Implantation of the implant 910 having a fixed length bridging element is similar to the implantation of the implant 10 and adjustable bridging element 12 as previously described, except that the bridging element is of a fixed length and is not adjusted during or after implantation. The overall length of the fixed length bridging element may be chosen as a percentage, e.g., 125 to 150 percent, of the desired septal-lateral length. The length of the fixed length bridging element will always be greater than the desired septal-lateral length.

Normal septal-lateral distances measured in normal persons may be used as a basis for determining the proper therapeutic septal-lateral distances in persons being treated. Target therapeutic septal-lateral distance may, for example, be chosen as some percentage, e.g. 125 percent, of septal-lateral distance in normal persons. The target septal-lateral distance must be sufficient to produce a therapeutic reduction in mitral regurgitation, but not over-stretch or tear tissues.

The use of a fixed length bridging element may reduce the complexity of the implantation of the implant system 910 because adjustment of a bridging element is not required. The implant system may also reduce the overall length of time for the implantation procedure.

Figure 67:
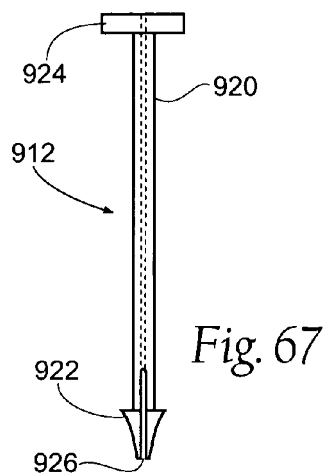
FIG. 67 is a side view of a fixed length inter-atrial bridging element of the type shown in FIG. 64, and showing the fixed length bridging element with a connective head on a first end and a stop on a second end.
Figure 68:
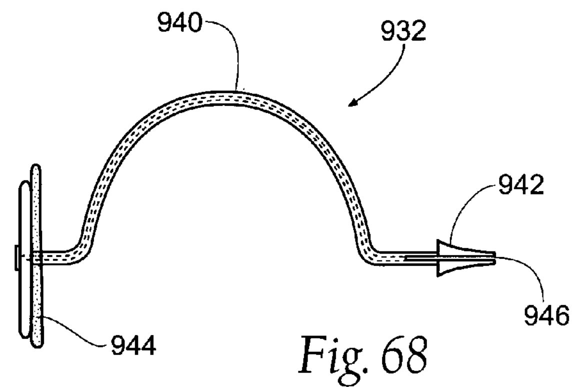
FIG. 68 is a side view of an arched or non-linear fixed length inter-atrial bridging element of the type shown in FIGS. 65 and 66, and showing the arched fixed length bridging element with a connective head on a first end and a stop on a second end.
Figure 69:
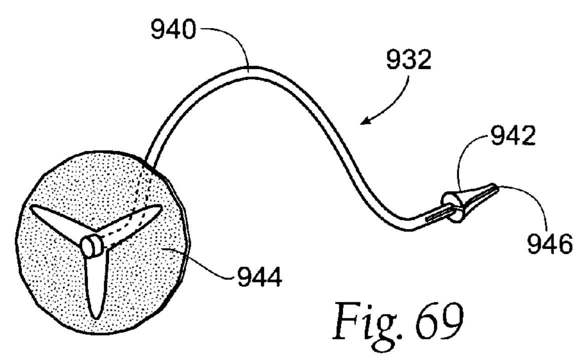
FIG. 69 is a perspective view of the arched fixed length inter-atrial bridging element of the type shown in FIG. 68, and showing and showing an alternative embodiment for a bridge stop on a second end.

The fixed length bridging element may be generally straight, as shown in FIG. 67, or may be generally arched or non-linear, as shown in FIGS. 68 and 69. FIGS. 65 and 66 show a sample of alternative deviations of the path of the arched fixed length bridging element 932, similar to those shown in FIGS. 12 to 20. Any single deviation or combinations of lateral or medial deviations and/or superior or inferior deviations in this path can be imparted, if desired, to affect the nature and direction of the force vector or vectors that the implant 910 applies. It should be appreciated that the fixed length bridging element can be preformed or otherwise configured with various medial/lateral and/or inferior/superior deviations to achieve targeted annulus and/or atrial structure remodeling, which takes into account the particular therapeutic needs and morphology of the patient. In addition, deviations in the path of the fixed length bridging element may also be imparted in order to avoid the high velocity blood path within a heart chamber, such as the left atrium. Also, stainless steel and Nitinol bridge elements may be used (as previously described and represented by FIGS. 13 to 17 and 19) that have curved septal to lateral components that impart desired ranges of tension and length in combination.

A. Fixed Length Bridging Element Structure

The fixed length bridging element may be constructed of a generally rigid material, such as stainless steel, in order to provide a predetermined reduction in the septal-lateral length, while allowing a wider range of tension across the heart valve annulus. Alternatively, the fixed length bridging element may be constructed of a semi-flexible or springy material, such as Nitinol, in order to provide a predetermined narrow range of tension across a heart valve annulus, such as the mitral valve annulus. A semi-flexible or springy material also facilitates the implantation of the fixed length bridging element using a deployment catheter. Nitinol has favorable fatigue properties and is also non-thrombogenic.

Figure 70A:
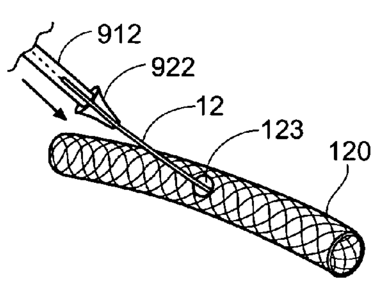
FIGS. 70A and 70B are perspective views showing the connective head of the fixed length bridging element guided by the tracking rail into the receiving aperture in a posterior or anterior bridge stop structure.
Figure 70B:
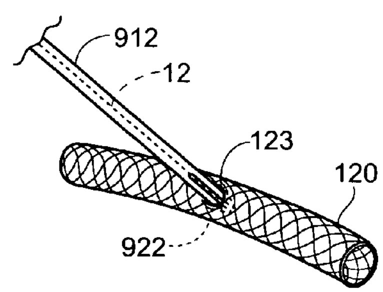

As shown in FIG. 67, the fixed length bridging element 912 comprises a hollow tube 920 having a connective or retentive member or head 922 at a first end and a retainer or stop 924 at a second end. The inner diameter of the hollow tube 920 must be large enough to enclose bridging element 12. The head 922 is preferably cone or chevron shaped and may include at least one crevice or slit 926 sized to allow each portion of the head 922 to flex so that the head can be inserted into a receiving aperture 123 in a T-shaped member or bridge stop 120 and snap into place (see FIGS. 70A and 70B). The stop 924 at the second end of the hollow tube 920 may be any practical shape (i.e. circular, square, triangle, or rod shaped) that offers sufficient surface area to abut the septal member 30 without allowing the stop 924 of the fixed length bridging element 912 to pass through the septal member. Alternatively, a septal member 30 may not be used and the stop 924 may abut the septal wall. Stop 924, for example, may incorporate any of the bridge stop embodiments described herein, and more particularly may incorporate any of the embodiments described in FIGS. 54 to 63C.

Figure 71A:
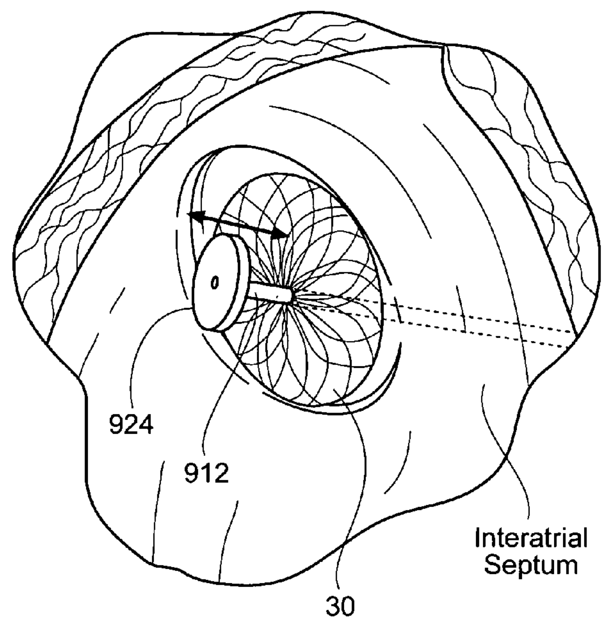
FIGS. 71A and 71B are sectional views showing the ability of a bridge stop used in conjunction with the implant shown in FIG. 64 to move back and forth independent of the septal wall and inner wall of the great cardiac vein.
Figure 71B:
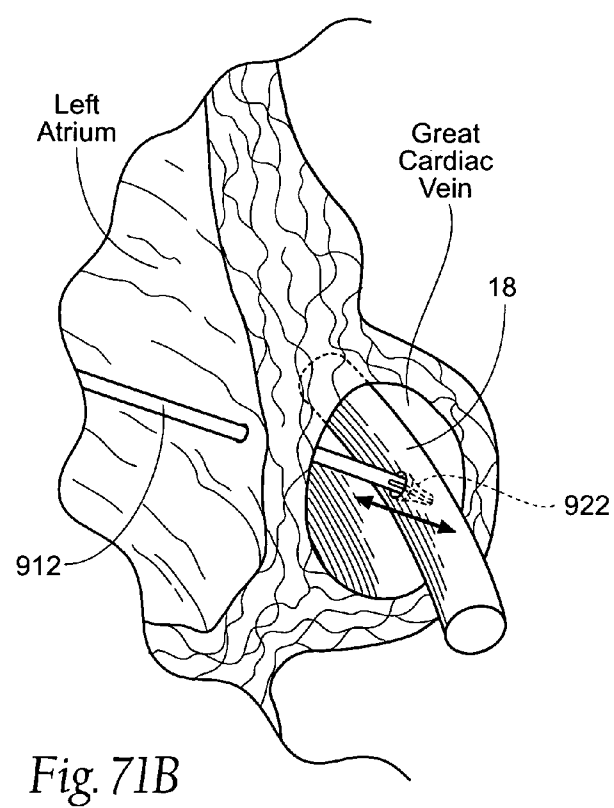

As previously described in relation to the implant 10, the stop 924 and the bridge stop 120 remain free to move back and forth independent of the inter-atrial septum and the inner wall of the great cardiac vein during a portion of the cardiac cycle when the tension force may be reduced or becomes zero (see FIGS. 71A and 71B).

FIGS. 68 and 69 show an alternative embodiment of a fixed length bridging element. The arched fixed length bridging element 932 comprises a hollow tube 940 having a connective or retentive head 942 at a first end and a retainer or stop 944 at a second end. The head 942 is preferably cone or chevron shaped and may include at least one crevice or slit 946 sized to allow each portion of the head 942 to flex so that the head can be inserted into a receiving aperture 123 in a T-shaped member or bridge stop 120 and snap into place (see FIGS. 70A and 70B). The stop 944 at the second end of the hollow tube 940 may be any practical shape (i.e. circular, square, triangle, or rod shaped) that offers sufficient surface area to abut the septal member 30 without allowing the stop 944 of the fixed length bridging element 932 to pass through the septal member 30. Alternatively, a septal member 30 may not be used and the stop 944 may abut the septal wall. Stop 944, for example, may incorporate any of the bridge stop embodiments described herein, and more particularly may incorporate any of the embodiments described in FIGS. 54 to 63C.

As previously described in relation to the implant 10, the stop 944 and the bridge stop 120 remain free to move back and forth independent of the inter-atrial septum and the inner wall of the great cardiac vein during a portion of the cardiac cycle when the tension force may be reduced or becomes zero (see FIGS. 71A and 71B).

Detailed Methods for Fixed Length Bridging Element Implantation

The steps of implantation and implantation apparatus as described in sections III(A) "Establish Posterior Bridge Stop Region" and III(B) "Establish Trans-Septal Bridging Element" are also used in conjunction with the implantation of the fixed length bridging element 912 and 932 and are therefore not repeated here. The remaining steps for implantation of the fixed length bridging element are described below. In addition, the bridging element 12 as described in these steps takes on an alternative purpose of serving as a "tracking rail" for delivery of the fixed length bridging element to its final implanted position.

1. Establish Anterior Bridge Stop Region

Now that the trans-septal bridging element or tracking rail 12 is in position, the anterior bridge stop region 16 is next to be established. In an alternative embodiment not incorporating a septal member 30, the step including the deployment of the septal member 30 may be skipped.

As seen in FIG. 29, the LA guide wire 74 is first backed out to at least the right atrium. In one embodiment incorporating a septal member 30, the proximal portion of the tracking rail 12 extending exterior the body is then threaded through or around the septal member 30. Preferably, the tracking rail 12 is passed through the septal member 30 outside of the body nearest its center so that when the fixed length bridging element 912 later passes over the tracking rail 12, the stop 924 of the fixed length bridging element 912 will also be centered and will transmit its force to a central point on the septal member 30, thereby reducing twisting or rocking of the septal member. The septal member is advanced over the tracking rail 12, through the vasculature, and is positioned within the right atrium and deployed at the fossa ovalis in a manner consistent with the manufacturer's instructions. At this point, tension may be applied under image guidance to establish the appropriate tension and/or length of bridging needed.

2. Fixed Length Bridging Element Positioning

Figure 72:
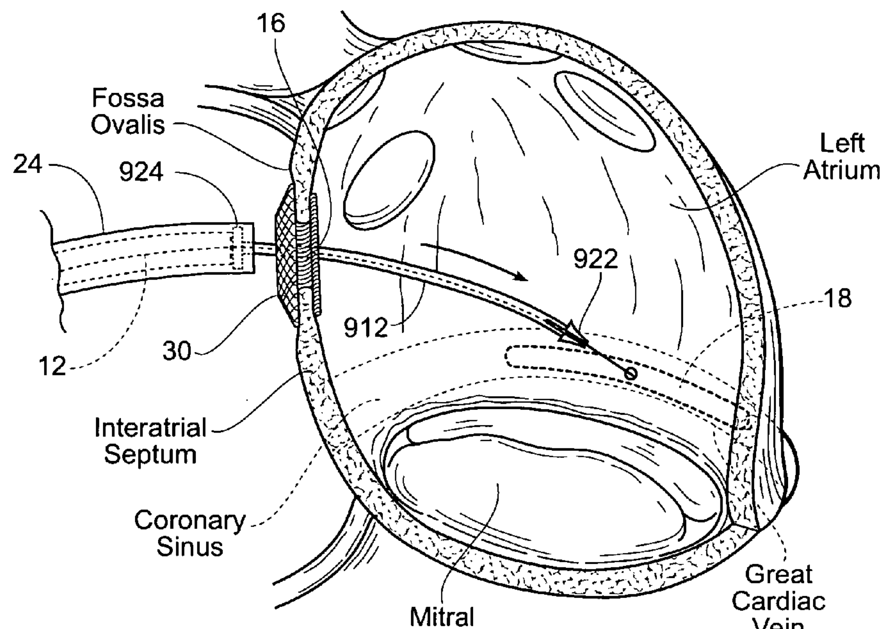
FIG. 72 is an anatomic anterior perspective view of the left atrium and a portion of the right atrium, with portions broken away and in section to show a step of implanting the implant system including the fixed length inter-atrial bridging element of the type shown in FIG. 64.
Figure 73:
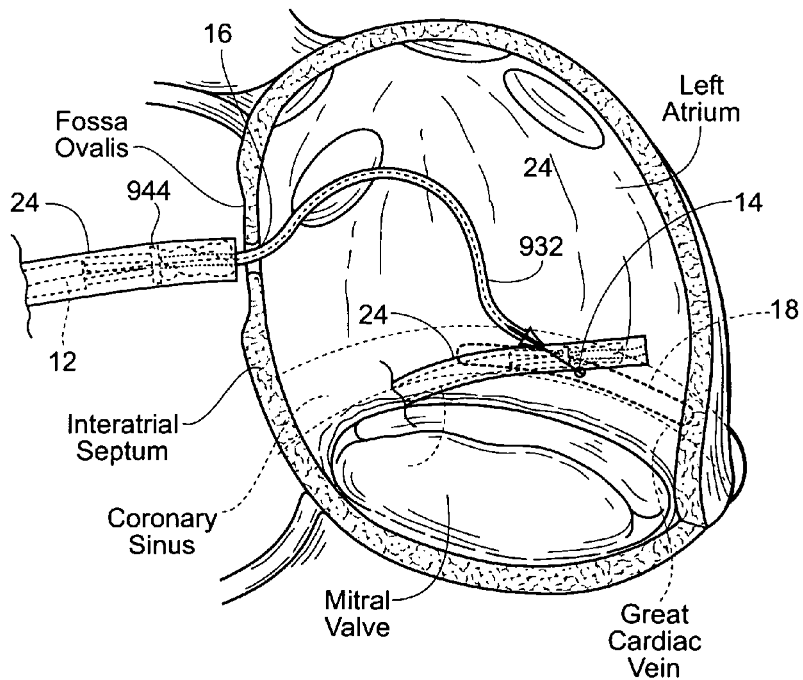
FIG. 73 is an anatomic anterior perspective view of the left atrium and a portion of the right; atrium, with portions broken away and in section to show a step of implanting the implant system including the arched fixed length inter-atrial bridging element of the type shown in FIGS. 65 and 66.

With the posterior bridge stop region 14, tracking rail 12, and anterior bridge stop region 16 configured as described, the fixed length bridging element 912, 932 is next to be positioned. External the body, the fixed length bridging element 912, 932 is positioned over the tracking rail 12 having an end remaining external the body. With a tension maintained on the tracking rail 12, the deployment catheter 24 may then be used to gently push the fixed length bridging element 912, 932 through the vasculature and into the right atrium, following the path of the tracking rail 12. When a septal member 30 is used, additional pushing of the deployment catheter 24 allows the shaped head of the fixed length bridging element 912, 932 to pass through the interstices of the septal member 30 until the stop 924, 944 of the fixed length bridging element comes to rest on the septal member 30 and restricts further passage (see FIG. 72). When a septal member 30 is not used, the stop 924, 944 comes to rest on the septal wall and restricts further passage. FIG. 73 shows the deployment of the arched fixed length bridging element 932 without the use of a septal member, and prior to the deployment of the stop 944.

Still with continued tension maintained on the tracking rail 12, a compressive force is applied to the deployment catheter 24 causing the shaped head 922, 942 to continue to follow the path of the tracking rail 12 directly into the receiving aperture 123 in the T-shaped member 120. The shaped head 922, 942 snaps into place within the aperture 123 in the T-shaped member (see FIGS. 70A and 70B). The tracking rail 12 may then be cut or detached, leaving a portion free to dangle or recoil within the tube 920, 940 of the fixed length bridging element, with the remainder removed along with the deployment catheter 24.

Alternatively, the tracking rail 12 may be allowed to extend into the IVC and into the femoral vein, possibly extending all the way to the femoral access point. Allowing the tracking rail to extend into the IVC and into the femoral vein would allow for future retrieval of the tracking rail, which would provide for access to the fixed length implant.

IX. Alternative Implantation Tools

Alternative embodiments of the GCV catheter 1040 and LA catheter 1060 may be used and are herein described. In this alternative embodiment, the procedure to core a lumen from the left atrium into the great cardiac vein is replaced with a procedure where a sharp tipped guide wire 1080 within the great cardiac vein is used to create a passage from the great cardiac vein into the left atrium.

Figure 74:
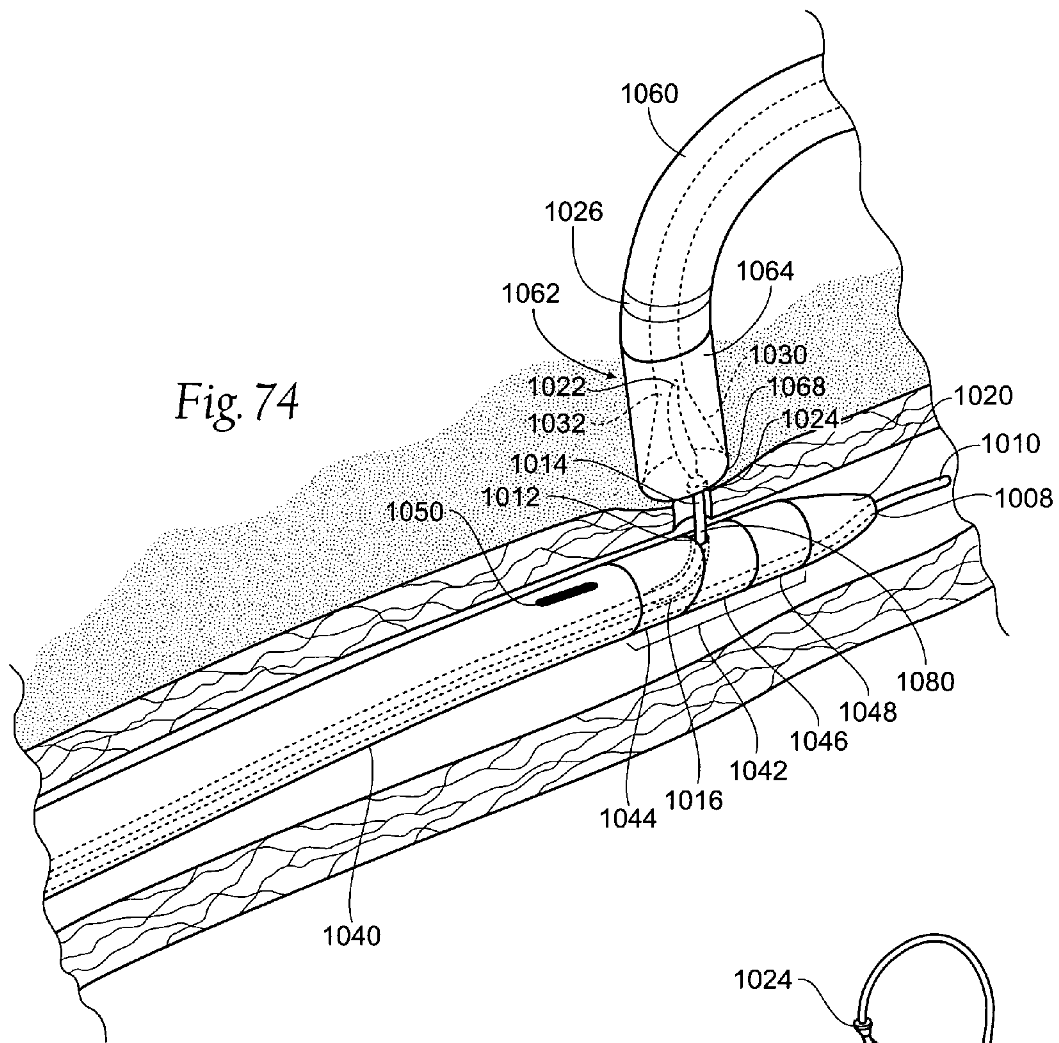
FIG. 74 is an anatomic partial perspective view of alternative magnetic catheter heads, with one catheter shown in the left atrium and one catheter shown in the great cardiac vein, and showing a side to end configuration.

FIG. 74 shows an alternative embodiment of the GCV catheter 1040 in accordance with the present invention. The GCV catheter 1040 preferably includes a magnetic head 1042 including a plurality of magnetic or ferromagnetic portions 1044,1046,1048 positioned near the distal end 1020 of the catheter 1040. As seen in FIG. 74, the GCV catheter magnetic head 1042 may include a dual lumen configuration. A navigation guide wire lumen 1008 allows the GCV guide wire 1010 to extend through the cone or bullet shaped head 1042 in order to steer the GCV catheter 1040 into position. A second side hole lumen 1012 allows the sharp tipped guide wire 1014 to extend through the head 1042 and directed the sharp tipped guide wire 1014 into the LA catheter magnetic head 1062. Both the GCV guide wire 1010 and the LA guide wire (not shown) may be pre-bent, and both may be steerable. The GCV catheter 1040 preferably includes a radio-opaque marker 1050 to facilitate adjusting the catheter 1040 under image guidance to align with the LA catheter 1060.

Figure 75:
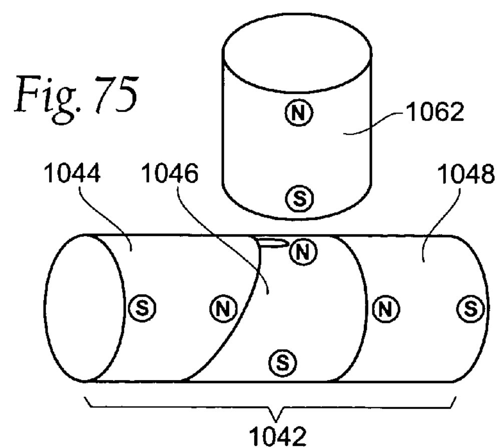
FIG. 75 is a simplified schematic of the magnetic catheter heads of FIG. 74.

The magnetic or ferromagnetic head 1042 is preferably polarized to magnetically attract or couple the distal end of the LA catheter 1060 (see FIG. 75). The magnetic portion 1042 includes a side hole 1012 formed therein to allow for passage of the LA guide wire 1014. As shown in FIG. 75, the magnetic portion comprises three magnets glued or clamped together. The magnetic portion 1042 comprises a distal magnet 1048, a proximal magnet 1044, and a center magnet 1046 between the distal 1048 and proximal 1044 magnets. The combination of magnets causes not only an attraction to the center to the triple magnet combination from the N-S attraction, but also S-S repulsion from the far end of the proximal 1044 and distal 1048 magnets. The center magnet 1046 has its poles oriented normal to the distal 1048 and proximal 1044 magnets which creates a radial focus to a single point on the system.

As shown in FIG. 74, the GCV catheter proximal magnet 1044 and center magnet 1046 are shaped and grooved at their intersection to create a ramp 1016 to turn the wire 1014 into the LA catheter 1060. In this case the exit hole 1012 is deliberately proximal of the magnetic center to lessen the ramp curve to less than 90 degrees, and therefore lessen the forces to make the bend in the wire 1014, with the funnel 1030 in the LA magnetic head 1062 large enough to catch the advancing wire 1014 into its center hole.

FIG. 74 shows an alternative embodiment of the LA catheter 1060. The LA catheter 1060 preferably includes a magnetic or ferromagnetic head 1062 positioned on the distal end 1068 of the catheter 1060. The inner diameter or lumen of the catheter shaft is preferably sized to allow passage of an LA wire and additionally may accept the guide wire passed 1014 from the GCV catheter 1040. The LA catheter 1060 may include a radio-opaque marker 1026 to facilitate adjusting the catheter 1060 under image guidance to align with the GCV catheter 1040.

The magnetic or ferromagnetic head 1062 of the LA catheter 1060 is polarized to magnetically attract or couple the distal end 1020 of the GCV catheter 1040. As shown in FIG. 75 the distal end 1068 of the LA magnetic head 1062 is polarized to attract the GCV catheter magnetic portion 1042. It should be noted that the magnetic forces in the heads 1042, 1062 may be reversed as long as attracting magnetic poles in the LA catheter 1060 and GCV catheter 1040 are aligned. The LA catheter 1060 magnetic head 1062 preferably includes a interior funnel 1030 and a center bore 1032 sized for passage of the cutting catheter and the LA guide wire 1014.

Figure 76:
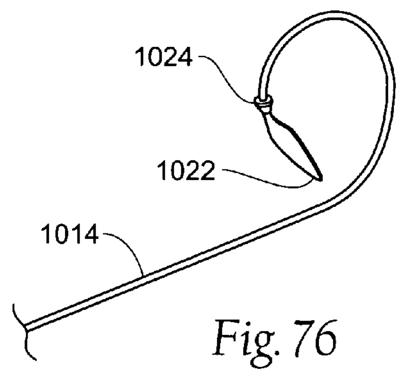
FIG. 76 is a partial perspective view of an alternative guide wire as shown in FIG. 74.

FIG. 76 shows a puncturing wire 1014 preferably sized and configured to be positioned within an inner diameter or lumen of the GCV catheter 1040. The wire tip 1022 of the puncturing wire may be flattened to allow the distal tip to bend more easily in its narrow dimension and make the transition into and out of the ramped 1016 and funneled 1030 sections of the magnets 1042, 1062. The flattened distal tip 1022 has a different bending modulus than the remainder of the puncturing wire 1014 which causes the distal tip 1022 to bend more easily in its narrow dimension. Additionally, the distal tip 1022 is designed to assume a flat down position through the curved or ramped portion of the catheter 1040. The tip 1022 may also be sharpened to reduce the puncturing force necessary. The sharpened tip 1022 may cause adjacent tissue to become easily lacerated. For that reason, the distal tip of the wire 1014 may be pre-shaped into a "pigtail" as shown in FIG. 76. In this manner, if the wire 1014 exits the catheter system it will curl up on itself and become less traumatic to the adjacent tissue. The wire tip 1022 could further be made of or laminated with radio-opaque materials 1024 to allow operator feedback as to the wire tip's 1022 location as it progresses through the system. The radio-opaque material 1024 could be any known material such as platinum and radio-opaque ring markers.

In use, the GCV catheter 1040 and the LA catheter 1060 may be advanced into the great cardiac vein and left atrium as previously described. The GCV catheter 1040 and the LA catheter 1060 each include the alternative magnetically attractive heads 1042,1062 as just described. As is shown in FIG. 74 the sharp-tipped guide wire 1014 is advanced through the GCV catheter 1040 to the internal wall of the great cardiac vein. The sharp-tipped guide wire 1014 is further advanced until it punctures or pierces the wall of the great cardiac vein and the left atrium, and enters the funneled end 1030 within the LA catheter 1060. Both the GCV catheter 1040 and the LA vein catheter 1060 may now be removed, leaving the GCV guide wire 1010 and the sharp-tipped guide wire 1014 in place. The posterior T-shaped bridge stop is now implanted via the GCV approach, as previously described and shown in FIGS. 35A to 36B.

Figure 77:
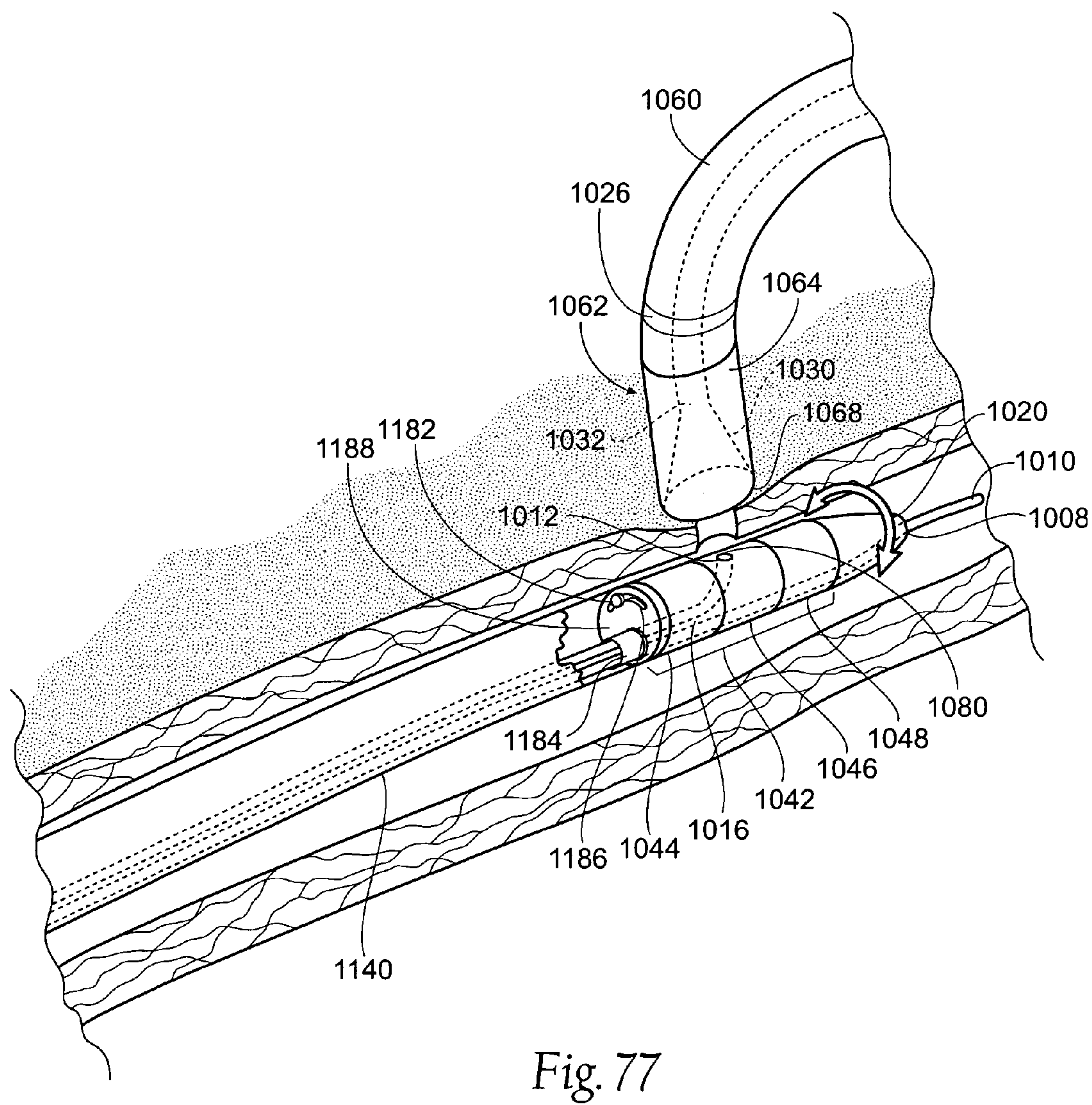
FIG. 77 is an anatomic partial perspective view of alternative magnetic catheter heads, with one catheter shown in the left atrium and one catheter shown in the great cardiac vein, showing a side to end configuration.

FIG. 77 shows an additional alternative embodiment of a GCV catheter 1140. The GCV catheter 1140 includes a three magnet arrangement 1042 as is described above and shown in FIG. 75, however the three magnet assembly 1042 is free to partially swivel.

The three magnet assembly 1042 includes the terminations of the delivery guide wire lumen 1008 and the puncturing wire lumen 1012. The three magnet assembly further includes a journal tube 1184 and a retaining pin 1182 coupled thereto. The journal tube 1184 and retaining pin 1182 may be attached by any known means such as gluing or screwing the parts to the magnets 1042.

A retaining button 1188 is formed at the end of the flexible portion of the catheter shaft 1140. The retaining button 1188 has a partial circumferential slot 1186 extending therethrough. The retaining pin 1182 attached to the three magnet assembly 1042 extends through the slot 1186. The retaining button 1188 also includes an aperture through which the journal tube 1184 extends.

The journal tube 1184 acts as a bearing surface around which the magnet assembly 1042 partially rotates. The rotation is limited by the engagement of the retaining pin 1182 in the slot 1186. The magnetic portion 1042 may rotate in a first direction until the retaining pin 1182 engages the first end of the slot 1186. The magnetic portion 1042 may then rotate in a second direction until the retaining pin 1182 engages the second end of the slot 1186. The partial rotation eliminates the chance that the wire lumens will kink.

The swiveling action removes some of the operator dependence by allowing the magnetic assembly 1042 to precisely align itself with the fourth magnet portion 1062 located in the LA catheter head by the force of their natural magnetic attraction. The magnetic attraction between the LA catheter head 1062 and GCV magnetic portion 1042 is the same as described in the previous embodiment and is shown in FIG. 75.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A system for establishing an access between a left atrium and a great cardiac vein, the system comprising a first catheter comprising a first catheter body sized and configured for axial advancement over a guide wire from a right atrium into in the great cardiac vein, the first catheter body having a center axis along which axial advancement occurs and including a distal end, the first catheter body including a guide wire lumen that extends along the center axis and an auxiliary lumen that extends along the center axis free of communication with the guide wire lumen, a second catheter comprising a second catheter body sized and configured for axial advancement over a guide wire from a right atrium, through a septum, and into in the left atrium, the second catheter body having a center axis along which axial advancement occurs and including a distal end, the second catheter body including an inner lumen that extends along the center axis of the second catheter body, a first head carried on the distal end of the first catheter body, the first head having a center axis and comprising a proximal region coupled to the distal end of the first catheter body, a distal region spaced from the distal end of the first catheter body, and a middle region between the proximal and distal regions, the first head including a guide lumen extension that communicates with the guide wire lumen of the first catheter body and extends along the center axis of the first head through the proximal, middle, and distal regions of the first head to a guide lumen exit opening at a distal end of the first head, the first head further having an auxiliary lumen extension that communicates with the auxiliary lumen of the first catheter body and extends along the center axis of the first head through the proximal region of the first head free of communication with the guide lumen extension, the auxiliary lumen extension including a ramped portion formed in the middle region of the first head that bends the auxiliary lumen extension away from the center axis of the first body to an auxiliary lumen exit opening formed in a side of the middle region of the first head, the proximal, middle, and distal regions of the first head each including, respectively, a proximal magnetic zone, a middle magnetic zone, and a distal magnetic zone, each magnetic zone comprising a magnetic or ferromagnetic material possessing poles of opposite polarity oppositely spaced apart along an axis, the axis of the middle magnetic zone extending in an orientation perpendicular to the center axis of the first head with one pole placed adjacent to the auxiliary lumen exit opening and the opposite pole placed on an opposite side of first body, the axis of the proximal magnetic zone extending in an orientation along the center axis of the first body with one pole placed adjacent to the middle magnetic zone and the opposite pole placed adjacent to the distal end of the first catheter body, the axis of the distal magnetic zone extending in an orientation along the center axis of the first body with one pole placed adjacent to the middle magnetic zone and the opposite pole placed adjacent to the guide lumen exit opening, the poles of the proximal magnetic zone and the distal magnetic zone placed adjacent to the middle magnetic zone having the same polarity as the pole of the middle magnetic zone placed adjacent to the auxiliary lumen exit opening to create a magnetic focus on the auxiliary lumen exit opening, a second head carried on the distal end of the second catheter body, the second head having a center axis and comprising a proximal region coupled to the distal end of the second catheter body and a distal region spaced from the distal end of the second catheter body, the second head including a lumen extension that communicates with the inner lumen of the second catheter body and extends along the center axis of the second head to a lumen exit opening at a distal end of the second head, the second head including a magnetic zone comprising a magnetic or ferromagnetic material possessing poles of opposite polarity oppositely spaced apart along an axis, the axis of the magnetic zone of the second head extending in an orientation along the center axis of the second head with one pole placed in the proximal region and the opposite pole placed in the distal region adjacent to the lumen exit opening of the second head, the pole placed adjacent to the lumen exit opening of the second head having a polarity opposite to the pole of the middle magnetic zone placed adjacent to auxiliary lumen exit opening of the first head, whereby the distal region of second head will magnetically couple to the middle region of the first head to place the lumen exit opening at a distal end of the second head in an alignment with the auxiliary lumen exit opening at the middle region of the first head, a first wire sized for passage through the guide wire lumen of the first catheter body, the guide lumen extension of the first head, and the guide lumen exit opening of the first head, to serve as the guide wire for the first catheter body for axially advancement of the first catheter body into a location within the great cardiac vein, a second wire sized for passage through the inner lumen of the second catheter body, the lumen extension of the second head, and the lumen exit opening of the second head, to serve as the guide wire for the second catheter body for axial advancement of the second catheter body into the left atrium to magnetically couple the distal region of the second head to the middle region of the first head, and an operative component sized for passage through the auxiliary lumen of the first catheter body, the auxiliary lumen extension of the first head, and the auxiliary lumen exit opening at the middle region of the first head, the operative component comprising a sharp distal tip to pierce tissue in the great cardiac vein for entry into the second catheter body through the magnetically coupled lumen exit opening at a distal end of the second head, to create between the first and second catheters an access between the left atrium and the great cardiac vein.

2. A system according to claim 1 wherein the lumen exit opening at the distal end of the second head includes an interior surface shaped as a funnel to guide entry of the sharp distal tip from the auxiliary lumen exit opening at the middle region of the first head into the lumen exit opening.

3. A method comprising providing system as defined in claim 1, deploying the first and second catheters, respectively, over the first and second wires, magnetically coupling the distal region of the second head to the middle region of the first head to place the lumen exit opening at a distal end of the second head in an alignment with the auxiliary lumen exit opening at the middle region of the first head, and passing the sharp distal tip of the operative component through the first catheter body to pierce tissue in the great cardiac vein and enter the second catheter body, to create between the first and second catheters an access between the left atrium and the great cardiac vein.

4. A method according to claim 3 further including deploying an implant into the left atrium through the access created between the first and second catheters.

5. A method according to claim 4 wherein deploying the implant reshapes a heart valve annulus.

* * * * *